United States Patent
Gray et al.

(10) Patent No.: US 9,284,578 B2
(45) Date of Patent: Mar. 15, 2016

(54) METHYL BUTENOL SYNTHASE

(71) Applicant: Board of Trustees of Michigan State University, East Lansing, MI (US)

(72) Inventors: Dennis Gray, Bay City, MI (US); Thomas D Sharkey, East Lansing, MI (US)

(73) Assignee: BOARD OF TRUSTEES OF MICHIGAN STATE UNIVERSITY, East Lansing, MI (US)

(*) Notice: Subject to any disclaimer, the term of this patent is extended or adjusted under 35 U.S.C. 154(b) by 0 days.

(21) Appl. No.: 14/174,694

(22) Filed: Feb. 6, 2014

(65) Prior Publication Data

US 2014/0248675 A1    Sep. 4, 2014

Related U.S. Application Data

(62) Division of application No. 13/321,458, filed as application No. PCT/US2010/035820 on May 21, 2010, now Pat. No. 8,679,802.

(60) Provisional application No. 61/180,757, filed on May 22, 2009.

(51) Int. Cl.
| | |
|---|---|
| *C12N 1/20* | (2006.01) |
| *C12N 1/00* | (2006.01) |
| *C12N 1/12* | (2006.01) |
| *C12N 15/00* | (2006.01) |
| *C12P 7/04* | (2006.01) |
| *C07H 21/04* | (2006.01) |
| *C12N 9/88* | (2006.01) |
| *C12P 7/16* | (2006.01) |

(52) U.S. Cl.
CPC ... *C12P 7/04* (2013.01); *C12N 9/88* (2013.01); *C12P 7/16* (2013.01); *Y02E 50/10* (2013.01)

(58) Field of Classification Search
None
See application file for complete search history.

(56) References Cited

U.S. PATENT DOCUMENTS

| | | | |
|---|---|---|---|
| 6,593,299 | B1 | 7/2003 | Bennett et al. |
| 8,679,802 | B2 | 3/2014 | Gray et al. |
| 2008/0038805 | A1 | 2/2008 | Melis |
| 2008/0274523 | A1 | 11/2008 | Renninger et al. |
| 2008/0274525 | A1 | 11/2008 | Bramucci et al. |
| 2008/0318292 | A1 | 12/2008 | Keasling et al. |
| 2009/0269816 | A1 | 10/2009 | Mendez et al. |
| 2012/0156745 | A1 | 6/2012 | Gray et al. |

FOREIGN PATENT DOCUMENTS

| | | |
|---|---|---|
| WO | WO-2010135674 A2 | 11/2010 |
| WO | WO-2010135674 A3 | 11/2010 |

OTHER PUBLICATIONS

00195274, Picea sitchensis (−)-linalool-like synthase mRNA, complete cds. NCBI Nucleotide, Mar. 14, 2006 [online]. [Retrieved on Aug. 11, 2010]., Retrieved from the internet: <URL: http://www.ncbi.nlm.nih.gov/nuccore177454874>.
"U.S. Appl. No. 12/657,748, Response filed Mar. 22, 2014 to Restriction Requirement mailed Feb. 21, 2013", 12 pgs.
"U.S. Appl. No. 13/321,458 , Response filed Sep. 3, 2013 to Non Final Office Action mailed May 31, 2013", 7 pgs.
"U.S. Appl. No. 13/321,458, Non Final Office Action mailed May 31, 2013", 8 pgs.
"U.S. Appl. No. 13/321,458, Notice of Allowance mailed Nov. 5, 2013", 12 pgs.
"U.S. Appl. No. 13/321,458, Restriction Requirement mailed Feb. 21, 2013", 7 pgs.
"International Application Serial No. PCT/US2010/035820, International Preliminary Report of Patentability mailed Dec. 1, 2011", 7 pgs.
"International Application Serial No. PCT/US2010/35820, Invitation to Pay Additional Fee mailed Sep. 20, 2010", 19 pgs.
"International Application Serial No. PCT/US2010/35820, Search Report mailed Mar. 7, 2011", 5 pgs.
"International Application Serial No. PCT/US2010/35820, Written Opinion mailed Mar. 7, 2011", 5 pgs.
Byun-McKay, et al., "Wound-Induced Terpene Synthase Gene Expression in Sitka Spruce That Exhibits Resistance or Susceptibility to Attack by the White Pine Weevil".
Demain, A. L, "The Business of Biotechnology", Indust, Biotechnol.; vol. 3 (3), Especially p. 275, coil, para 4; col. 2, para 1., (2007), 269-283.
Martin, et al., "Functional Characterization of Nine Norway Spruce TPS Genes and Evolution of Gymnosperm Terpene Synthases of the TPS-d Subfamily", Plant Physiology, (2004), 1908-1927.

*Primary Examiner* — Iqbal H Chowdhury
(74) *Attorney, Agent, or Firm* — Schwegman Lundberg & Woessner, P.A.

(57) ABSTRACT

The present invention provides novels genes encoding methyl butenol (MBO) synthase, methy butenol synthases and their use in methyl butenol production.

14 Claims, 20 Drawing Sheets

P._pseudostrobus_estevezii
TCTAGCAAGGTTAAGGTTGTCCGCAGAACGATCTCAACTTCCATCCGCATG
TGTCGGATAACCACTGTATCCGGTGAAGGCGTACAGAGACGCATAGCAAA
TCATCATTCCAACCTCTGGGACGATAATTTCATACAGTCCCTCTCAACCCC
TTATGGGGCAATTTCGTACCATGAAAGTGCTCAGAAACTTATTGGAGAAG
TAAAAGAGATAATCAATTCAATCTCGGTTAAAGATGGAGAATTAATCACC
CCCTCCAATGATCTCCTTATGCGGCTCTCTATAGTCGATAGCATTGAACGT
TTGGGAATTGATAGGCATTTCAAAAGTGAAATAAAATCAGCTCTGGATTA
CGTTTACAGTTATTGGAACGAAAAAGGCATTGGGTGGGGAAGAGATAGTG
TTGTTGCCGATCTCAACTCAACTGCCTTGGGGCTTCGAACTCTACGACTAC
ACGGATACCCGGTGTCTTCAGATGTGTTACAACACTTCAAAGAACAAAAA
GGGCAGTTTGCATGTTCGGCCATTCAAACAGAGGGAGAGATAAGAAGTGT
TCTCAACTTATTTCGGGCTTCCCAAATTGCCTTTCCGGGAGAGAAAGTTAT
GGAAGAGGCAGAAGTCTTCTCTACAATATATTTAAAAGAAGCCATACTAA
AGCTTCCGGTCTGCGGTCTTTCACGAGAGATATCGTACGTTCTGGAATATG
GTTGGCATATAAATTTGCCAAGATTGGAAGCAAGGAACTACATCGACGTA
TTTGGACAGGACCCCATTTATTTGACGCCAAATATGAAGACCAAAAACT
TCTAGAACTTGCAAAGTTGGAGTTCAATATGTTTCACTCTTTACAACAGCA
AGAGCTAAAGCTTCTCTCCAGATGGTGGAAAGATTCGGGTTTCTCTCAAAT
GACCTTCCCTCGGCATCGTCACGTGGAATATTACACTTTGGCATCTTGCAT
TGATAGTGAACCTCAACATTCTTCGTTCAGACTTGGATTTGCCAAAATCTT
TCATCTTGCCACGGTTCTTGACGATATTTACGACACCTTTGGCACGATGGA
TGAGCTAGAACTCTTCACGGCGGCAGTTAAGAGGTGGCATCCGTCTGCGA
CGGAGTGGCTTCCAGAATATATGAAAGGAGTATATATGGTGCTTTACGAA
ACCGTTAACGAAATGGCAGGAGAAGCAGAAAAGTCTCAAGGCCGAGACA
CGCTCAACTATGCCCGAAATGCTTTGGAGGCTTATATTGATGCTTCTATGA
AAGAAGCGAAGTGGATTTTCAGTGGTTTTTTGCCAACATTTGAGGAGTAC
CTGGATAACGGGAAAGTTAGTTTCGGTTATAGCATTGGCACATTGCAACC
CATTCTGACGTTGGGCATTCCCTTTCCTCATCACATCCTACAAGAAATAGA
CTTTCCTTCCAGGCTCAATGATGTGGCATGTTCCATTCTCCGACTAAAAGG
CGACATTCACACTTACCAGGCTGAGAGGAGCCGTGGAGAAAAATCTTCGT
GTATATCATGTTATATGGAAGAGAATCCCGAGTCAACAGAGGAAGATGCA
ATCAATCATGTCAACTCCATGGTCGACAAATTACTCAAGGAACTAAATTG
GGAGTATCTGAGACCTGATAGCAATGTTCCAATCACTTCCAAGAAACATG
CATTTGACATTCTGAGAGCTTTCTACCATCTCTACAAATACCGAGATGGCT
TCAGCGTTGCGAACTATGAAATAAAGAATTTGGTCATGACAACCGTCATT
GAGCCTGTGCCTTTATAA- (SEQ ID NO:1)

P_cooperi_ornelasi_MBO
TCTAGCAAGGTTAAGGTTGTCCGCAGAACGATCTCAACTTCCATCCGCATG
TGTCGGATAACCACTGTATCCGGTGAAGGCGTACAGAGACGCATAGCAAA
TCATCATTCCAACCTCTGGGACGATAATTTCATACAGTCCCTCTCAACGCC
TTATGGGGCAATTTCGTACCATGAAAGTGCTCAGAAACTTATTGGAGAAG
TAAAAGAGATGATCAATTCAATCTCGGTTAAAGATGGAGAATTAATCACC
CCCTCCAATGATCTCCTTATGCGGCTCTCTATAGTCGATAGCATTGAACGT
TTGGGAATCGATAGGCATTTCAAAAGTGAAATAAAATCAGCTCTGGATTA
TGTTTACAGTTATTGGAACGAAAAAGGCATTGGGTGGGGAAGAGATAGTG
TTGTTGCCGATCTCAACTCAACTGCCTTGGGGCTTCGAACTCTACGACTAC

FIG.1A

ACGGATACCCGGTGTCTTCAGATGTGTTACAACACTTCAAAGAACAAAAA
GGGCAGTTTGCATGTTCGGCCATTCAAACAGAGGGAGAGATAAGAAGTGT
TCTCAACTTATTTCGGGCTTCCCAAATTGCCTTTCCGGGAGAGAAAGTTAT
GGAAGAGGCAGAAGTCTTCTCTACAATATATTTAAAAGAAGCCATACTAA
AGCTTCCGGTCTGCGGTCTTTCACGAGAGATATCGTACGTTCTGGAATATG
GTTGGCATATAAATTTGCCAAGATTGGAAGCAAGGAACTACATCGACGTA
TTTGGACAGGACCCCATTTATTTGACGCCAAATATGAAGACCCAAAAACT
TCTAGAACTTGCAAAGTTGGAGTTCAATATGTTTCACTCTTTACAACAGCA
AGAGCTAAAGCTTCTCTCCAGATGGTGGAAAGATTCGGGTTTCTCTCAAAT
GACCTTCCCTCGGCATCGTCACGTGGAATATTACACTTTGGCATCTTGCAT
TGATAGTGAACCTCAACATTCTTCGTTCAGACTTGGATTTGCCAAAATCTT
TCATCTTGCCACGGTTCTTGACGATATTTACGACACCTTTGGCACGATGGA
TGAGCTAGAACTCTTCACGGCGGCAGTTAAGAGGTGGCATCCGTCTGCGA
CGGAGTGGCTTCCAGAATATATGAAAGGAGTATATATGGTGCTTTACGAA
ACCGTTAACGAAATGGCAGGAGAAGCAGAAAAGTCTCAAGGCCGAGACA
CGCTCAACTATGCCCGAAATGCTTTGGAGGCTTATATTGATGCTTCTATGA
AAGAAGCGAAGTGGATTTTCAGTGGTTTTTGCCAACATTTGAGGAGTAC
CTGGATAACGGGAAAGTTAGTTTCGGTTATAGCATTGGCACATTGCAACC
CATTCTGACGTTGGGCATTCCCTTTCCTCATCACATCCTACAAGAAATAGA
CTTTCCTTCCAGGCTCAATGATGTGGCATGTTCCATTCTCCGACTAAAAGG
CGACATTCACACTTACCAGGCTGAGAGGAGCCGTGGAGAAAAATCTTCGT
GTATATCATGTTATATGGAAGAGAATCCCGAGTCAACAGAGGAAGATGCA
ATCAATCATATCAACTCCATGGTCGACAAATTACTCAAGGAACTAAATTG
GGAGTATCTGAGACCTGATAGCAATGTTCCAATCACTTCCAAGAAACATG
CATTTGACATTCTGACAGCTTTCTACCATCTCTACAAATACCGAGATGGCT
TCAGCGTTGCGAACTATGAAATAAAGAATTTGGTCATGACAACCGTCATT
GAGCCTGTGCCTTTATAA-(SEQ ID NO:2)

P._hartwegii_MBO
TCTAGCAAGGTTAAGGTTGTCCGCAGAACGATCTCAACTTCCATCCGCATG
TGTCGGATAACCACTGTATCCGGTGAAGGCGTACAGAGACGCATAGCAAA
TCATCATTCCAACCTCTGGGACGATAATTTCATACAGTCCCTCTCAACGCC
TTATGGGGCAATTTCGTACCATGAAAGTGCTCAGAAACTTATTGGAGAAG
TAAAAGAGATGATCAATTCAATCTCGGTTAAAGATGGAGAATTAATCACC
CCCTCCAATGATCTCCTTATGCGGCTCTCTATAGTCGATAGCATTGAACGT
TTGGGAATCGATAGGCATTTCAAAAGTGAAATAAAATCAGCTCTGGATTA
TGTTTACAGTTATTGGAACGAAAAAGGCATTGGTGGGGAAGAGATAGTG
TTGTTGCCGATCTCAACTCAACTGCCTTGGGGCTTCGAACTCTACGACTAC
ACGGATACCCGGTGTCTTCAGATGTGTTACAACACTTCAAAGAACAAAAA
GGGCAGTTTGCATGTTCGGCCATTCAAACAGAGGGAGAGATAAGAAGTGT
TCTCAACTTATTTCGGGCTTCCCAAATTGCCTTTCCGGGAGAGAAAGTTAT
GGAAGAGGCAGAAGTCTTCTCTACAATATATTTAAAAGAAGCCATACTAA
AGCTTCCGGTCTGCGGTCTTTCACGAGAGATATCGTACGTTCTGGAATATG
GTTGGCATATAAATTTGCCAAGATTGGAAGCAAGGAACTACATCGACGTA
TTTGGACAGGACCCCATTTATTTGACGCCAAATATGAAGACCCAAAAACT
TCTAGAACTTGCAAAGTTGGAGTTCAATATGTTTCACTCTTTACAACAGCA
AGAGCTAAAGCTTCTCTCCAGATGGTGGAAAGATTCGGGTTTCTCTCAAAT
GACCTTCCCTCGGCATCGTCACGTGGAATATTACACTTTGGCATCTTGCAT
TGATAGTGAACCTCAATATTCTTCGTTCAGACTTGGATTTGCCAAAATCTT
TCATCTTGCCACGGTTCTTGACGATATTTACGACACCTTTGGCACGATGGA

FIG.1B

TGAGCTAGAACTCTTCACGGCGGCAGTTAAGAGGTGGCATCCGTCTGCGA
CGGAGTGGCTTCCAGAATATATGAAAGGAGTATATATGGTGCTTTACGAA
ACCGTTAACGAAATGGCAGGAGAAGCAGAAAAGTCTCAAGGCCGAGACA
CGCTCAACTATGCCCGAAATGCTTTGGAGGCTTATATTGATGCTTCTATGA
AAGAAGCGAAGTGGATTTTCAGTGGTTTTTTGCCAACATTTGAGGAGTAC
CTGGATAACGGGAAAGTTAGTTTCGGTTATAGCATTGGCACATTGCAACC
CATTCTGACGTTGGGCATTCCCTTTCCTCATCACATCCTACAAGAAATAGA
CTTTCCTTCCAGGCTCAATGATGTGGCATGTTCCATTCTCCGACTAAAAGG
CGACATTCACACTTACCAGGCTGAGAGGAGCCGTGGAGAAAAATCTTCGT
GTATATCATGTTATATGGAAGAGAATCCCGAGTCAACAGAGGAAGATGCA
ATCAATCATATCAACTCCATGGTCGACAAATTACTCAAGGAACTAAATTG
GGAGTATCTGAGACCTGATAGCAATGTTCCAATCACTTCCAAGAAACATG
CATTTGACATTCTGAGAGCTTTCTACCATCTCTACAAATACCGAGATGGCT
TCAGCGTTGCGAACTATGAAATAAAGAATTTGGTCATGACAACCGTCATT
GAGCCTGTGCCTTTATAA-(SEQ ID NO:3)

P._ponderosa_MBO1
TCTAGCAAGGTTAAGGTTGTCCGCAGAACGATCTCAACTTCCATCCGCATG
TGTCGGATAACCACTGAATCCGGTGAAGGCGTACAGAGACGCATAGCAAA
TCATCATTCCAACCTCTGGGACGATAATTTCATACAGTCCCTCTCAACGCC
TTATGGGGCAATTTCGTACCATGAAAGTGCTCAGAAACTTATTGGAGAAG
TAAAAGAGATGATCAATTCAATCTCGCTTAAAGATGGAGAATTAATCACC
CCCTCCAATGATCTCCTTATGCGGCTCTCTATAGTTGATAGCATTGAACGT
TTGGGAATCGATAGGCATTTCAAAAGTGAAATAAAATCAGCTCTGGATTA
TGTTTACAGTTATTGGAACGAAAAGGCATTGGGTGGGAAGAGATAGTG
TTGTTGCCGATCTCAACTCAACTGCCTTGGGGCTTCGAACTCTACGACTAC
ACGGATACCCGGTGTCTTCAGATGTGTTACAACACTTCAAAGAACAAAAA
GGGCAGTTTGCATGTTCGGCCATTCAAACAGAGGGAGAGATAAGAAGTGT
TCTCAACTTATTTCGGGCTTCCCAAATTGCCTTTCCGGGAGAGAAAGTTAT
GGAAGAGGCAGAAGTCTTCTCTACAATATATTTAAAAGAAGCCATACTAA
AGCTTCCGGTCTGCGGTCTTTCACGAGAGATATCGTACGTTCTGGAATATG
GTTGGCATATAAATTTGCCAAGATTGGAAGCAAGGAACTACATCGACGTA
TTTGGACAGGACCCCATTTATTTGACGCCAAATATGAAGACCCAAAAACT
TCTAGAACTTGCAAAGTTGGAGTTCAATATGTTTCACTCTTTACAACAGCA
AGAGCTAAAGCTTCTCTCCAGATGGTGGAAAGATTCGGGTTTCTCTCAAAT
GACCTTCCCTCGGCATCGTCACGTGGAATATTACACTTTGGCATCTTGCAT
TGATAGTGAACCTCAACATTCTTCGTTCAGACTTGGATTTGCCAAAATCTT
TCATCTTGCCACGGTTCTTGACGATATTTACGACACCTTTGGCACGATGGA
TGAGCTAGAACTCTTCACGGCGGCAGTTAAGAGGTGGCATCCGTCTGCGA
CGGAGTGGCTTCCAGAATATATGAAAGGAGTATATATGGTGCTTTACGAA
ACCGTTAACGAAATGGCGAGAGAAGCAGAAAAGTCTCAAGGCCGAGACA
CGCTCAACTATGCCCGAAATGCTTTGGAGGCTTATATTGATGCTTCTATGA
AAGAAGCGAAGTGGATTTTCAGTGGTTTTTTGCCAACATTTGAGGAGTAC
CTGGATAACGGGAAAGTTAGTTTCGGTTATAGCATTGGCACATTGCAACC
CATTCTGACGTTGGGCATTCCCTTTCCTCATCACATCCTACAAGAAATAGA
CTTTCCTTCCAGGCTCAATGATGTGGCATGTTCCATTCTCCGACTAAAAGG
CGACATTCACACTTACCAGGCTGAGAGGAGCCGTGGAGAAAAATCTTCGT
GTATATCATGTTATATGGAAGAGAATCCCGAGTCAACAGAGGAAGATGCA
ATCAATCATATCAACTCCATGGTCGACAAATTACTCAAGGAACTAAATTG
GGAGTATCTGAGACCTGATAGCAATGTTCCAATCACTTCCAAGAAACATG

FIG.1C

CATTTGACATTCTGAGAACTTTCTACCATCTCTACAAATACCGAGATGGCT
TCAGCGTTGCGAACTATGAAATAAAGAATTTGGTCATGACAACCGTCATT
GAGCCTGTGCCTTTATAA-(SEQ ID NO:4)

P._ponderosa_MBO2
TCTAGCAAGGTTAAGGTTGTCCGCAGAACGATCTCAACTTCCATCCGCATG
TGTCGGATAACCACTGAATCCGGTGAAGGCGTACAGAGACGCATAGCAAA
TCATCATTCCAACCTCTGGGACGATAATTTCATACAGTCCCTCTCAACGCC
TTATGGGGCAATTTCGTACCATGAAAGTGCTCAGAAACTTATTGGAGAAG
TAAAAGAGATGATCAATTCAATCTCGCTTAAAGATGGAGAATTAATCACC
CCCTCCAATGATCTCCTTATGCGGCTCTCTATAGTTGATAGCATTGAACGT
TTGGGAATCGATAGGCATTTCAAAAGTGAAATAAAATCAGCTCTGGATTA
TGTTTACAGTTATTGGAACGAAAAAGGCATTGGGTGGGAAGAGATAGTG
TTGTTGCCGATCTCAACTCAACTGCCTTGGGGCTTCGAACTCTACGACTAC
ACGGATACCCGGTGTCTTCAGATGTGTTACAACACTTCAAAGAACAAAAA
GGGCAGTTTGCATGTTCGGCCATTCAAACAGAGGGAGAGATAAGAAGTGT
TCTCAACTTATTTCGGGCTTCCCAAATTGCCTTTCCGGGAGAGAAAGTTAT
GGAAGAGGCAGAAGTCTTCTCTACAATATATTTAAAAGAAGCCATACTAA
AGCTTCCGGTCTGCGGTCTTTCACGAGAGATATCGTACGTTCTGGAATATG
GTTGGCATATAAATTTGCCAAGATTGGAAGCAAGGAACTACATCGACGTA
TTTGGACAGGACCCCATTTATTTGACGCCAAATATGAAGACCCAAAAATT
TCTAGAACTTGCAAAGTTGGAGTTCAATATGTTTCACTCTTTACAACAGCA
AGAGCTAAAGCTTCTCTCCAGATGGTGGAAAGATTCGGGTTTCTCTCAAAT
GACCTTCCCTCGGCATCGTCACGTGGAATATTACACTTTGGCATCTTGCAT
TGATAGTGAACCTCAACATTCTTCGTTCAGACTTGGATTTGCCAAAATCTT
TCATCTTGCCACGGTTCTTGACGATATTTACGACACCTTTGGCACGATGGA
TGAGCTAGAACTCTTCACGGCGGCAGTTAAGAGGTGGCATCCGTCTGCGA
CGGAGTGGCTTCCAGAATATATGAAAGGAGTATATATGGTGCTTTACGAA
ACCGTTAACGAAATGGCGAGAGAAGCAGAAAAGTCTCAAGGCCGAGACA
CGCTCAACTATGCCCGAAATGCTTTGGAGGCTTATATTGATGCTTCTATGA
AAGAAGCGAAGTGGATTTTCAGTGGTTTTTGCCAACATTTGAGGAGTAC
CTGTATAACGGGAAAGTTAGTTTCGGTTATAGCATTGGCACATTGCAACCC
ATTCTGACGTTGGGCATTCCCTTTCCTCATCACATCCTACAAGAAATAGAC
TTTCCTTCCAGGCTCAATGATGTGGCATGTTCCATTCTCCGACTAAAAGGC
GACATTCACACTTACCAGGCTGAGAGGAGCCGTGGAGAAAAATCTTCGTG
TATATCATGTTATATGGAAGAGAATCCCGAGTCAACAGAGGAAGATGCAA
TCAATCATATCAACTCCATGGTCGACAAATTACTCAAGGAACTAAATTGG
GAGTATCTGAGACCTGATAGCAATGTTCCAATCACTTCCAAGAAACATGC
ATTTGACATTCTGAGAACTTTCTACCATCTCTACAAATACCGAGATGGCTT
CAGCGTTGCGAACTATGAAATAAAGAATTTGGTCATGACAACCGTCATTG
AGCCTGTGCCTTTATAA-(SEQ ID NO:5)

P._jeffreyi_MBO
TCTAGCAAGGTTAAGGTTGTCCGCAGAACGATCTCAACTTCCATCCGCATG
TGTCGGATAACCACTGAATCCGGTGAAGGCGTACAGAGACGCATAGCAAA
TCATCATTCCAACCTCTGGGACGATAATTTCATACAGTCCCTCTCAACGCC
TTATGGGGCAATTTCGTACCATGAAAGTGCTCAGAAACTTATTGGAGAAG
TAAAAGAGATGATCAATTCAATCTCGCTTAAAGATGGAGAATTAATCACC
CCCTCCAATGATCTCCTTATGCGGCTCTCTATAGTTGATAGCATTGAACGT
TTGGGAATCGATAGGCATTTCAAAAGTGAAATAAAATCAGCTCTGGATTA

FIG.1D

TGTTTACAGTTATTGGAACGAAAAAGGCATTGGGTGGGAAGAGATAGTG
TTGTTGCCGATCTCAACTCAACTGCCTTGGGGCTTCGAACTCTACGACTAC
ACGGATACCCGGTGTCTTCAGATGTGTTACAACACTTCAAAGAACAAAAA
GGGCAGTTTGCATGTTCGGCCATTCAAACAGAGGGAGAGATAAGAAGTGT
TCTCAACTTATTCGGGCTTCCCAAATTGCCTTTCCGGGAGAGAAAGTTAT
GGAAGAGGCAGAAGTCTTCTCTACAATATATTTAAAAGAAGCCATACTAA
AGCTTCCGGTCTGCGGTCTTTCACGAGAGATATCGTACGTTCTGGAATATG
GTTGGCATATAAATTTGCCAAGATTGGAAGCAAGGAACTACATCGACGTA
TTTGGACAGGACCCCATTTATTTGACGCCAAATATGAAGACCCAAAAACT
TCTAGAACTTGCAAAGTTGGAGTTCAATATGTTTCACTCTTTACAACAGCA
AGAGCTAAAGCTTCTCTCCAGATGGTGGAAAGATTCGGGTTTCTCTCAAAT
GACCTTCCCTCGGCATCGTCACGTGGAATATTACACTTTGGCATCTTGCAT
TGATAGTGAACCTCAACATTCTTCGTTCAGACTTGGATTTGCCAAAATCTT
TCATCTTGCCACGGTTCTTGACGATATTTACGACACCTTTGGCACGATGGA
TGAGCTAGAACTCTTCACGGCGGCAGTTAAGAGGTGGCATCCGTCTGCGA
CGGAGTGGCTTCCAGAATATATGAAAGGAGTATATATGGTGCTTTACGAA
ACCGTTAACGAAATGGCAGGAGAAGCAGAAAAGTCTCAAGGCCGAGACA
CGCTCAACTATGCCCGAAATGCTTCGGAGGCTTATATTGATGCTTCTATGA
AAGAAGCGAAGTGGATTTTCAGTGGTTTTTTGCCAACATTTGAGGAGTAC
CTGGATAACGGGAAGTTAGTTTCGGTTATAGCATTGGCACATTGCAACC
CATTCTGACGTTGGGCATTCCCTTTCCTCATCACATCCTACAAGAAATAGA
CTTTCCTTCCAGGCTCAATGATGTGGCATGTTCCATTCTCCGACTAAAAGG
CGACATTCACACTTACCAGGCTGAGAGGAGCCGTGGAGAAAAATCTTCGT
GTATATCATGTTATATGGAAGAGAATCCCGAGTCAACAGAGGAAGATGCA
ATCAATCATATCAACTCCATGGTCGACAAATTACTCAAGGAACTAAATTG
GGAGTATCTGAGACCTGATAGCAATGTTCCAATCACTTCCAAGAAACATG
CATTTGACATTCTGAGAGCTTTCTACCATCTCTACAAATACCGAGATGGCT
TCAGCGTTGCGAACTATGAAATAAAGAATTTGGTCATGACAACCGTCATT
GAGCCTGTGCCTTTATAA-(SEQ ID NO:6)

P._sabiniana_MBO1
TCTAGCAAGGTTAAGGTTGTCCGCAGAACGATCTCAACTTCCATCCGCATG
TGTCGGATAACCACTGAATCCGGTGAAGGCGTACAGAGACGCATAGCAAA
TCATCATTCCAACCTCTGGGACGATAATTTCATACAGTCCCTCTCAACGCC
TTATGGGGCAATTTCGTACCATGAAAGTGCTCAGAAACTTATTGGAGAAG
TAAAAGAGATGATCAATTCAATCTCGGTTAAAGATGGAGAATTAATCACC
CCCTCCAATGATCTCCTTATGCGGCTCTCTATAGTTGATAGCATTGAACGT
TTAGGAATCGATAGGCATTTCAAAAGTGAAATAAAATCAGCTCTGGATTA
TGTTTACAGTTATTGGAACGAAAAAGGCATTGGGTGGGAAGAGATAGTG
TTGTTGCCGATCTCAACTCAACTGCCTTGGGGCTTCGAACTCTACGACTAC
ACGGATACCCGGTGTCTTCAGATGTGTTACAACACTTCAAAGAACAAAAA
GGGCAGTTTGCATGTTCGGCCATTCAAACAGAGGGAGAGATAAGAAGTGT
TCTCAACTTATTCGGGCTTCCCAAATTGCCTTTCCGGGAGAGAAAGTTAT
GGAAGAGGCAGAAGTCTTCTCTACAATATATTTAAAAGAAGCCATACTAA
AGCTTCCGGTCTGCGGTCTTTCACGAGAGATATCGTACGTTCTGGAATATG
GTTGGCATATAAATTTGCCAAGATTGGAAGCAAGGAACTACATCGACGTA
TTTGGAGAGGACCCCATTTATTTGACGCCAAATATGAAGACCCAAAAACT
TCTAGAACTTGCAAAGTTGGAGTTCAATATGTTTCACTCTTTACAACAGCA
AGAGCTAAAGCTTCTCTCCAGATGGTGGAAAGATTCGGGTTTCTCTCAAAT
GACCTTCCCTCGGCATCGTCACGTGGAATATTACACTTTGGCATCTTGCAT

FIG.1E

TGATAGTGAACCTCAACATTCTTCGTTCAGACTTGGATTTGCCAAAATCTT
TCATCTTGCCACGGTTCTTGACGATATTTACGACACCTTTGGCACGATGGA
TGAGCTAGAACTCTTCACGGCGGCAGTTAAGAGGTGGCATCCGTCTGCGA
CGGAGTGGCTTCCAGAATATATGAAAGGAGTATATATGGTGCTTTACGAA
ACCGTTAACGAAATGGCAGGAGAAGCAGAAAAGTCTCAAGGCCGAGACA
CGCTCAACTATGGCCGAAATGCTTTGGAGGCTTATATTGATGCTTCTATGG
AAGAAGCGAAGTGGATTTTCAGTGGTTTTTGCCAACATTTGAGGAGTAC
CTGGATAACGGGAAAGTTAGTTTCGGTTATGGCATTGGCACATTGCAACC
CATTCTGACGTTGGGCATTCCCTTTCCTCATCACATCCTACAAGAAATAGA
CTTTCCTTCCAGGCTCAATGATGTGGCATCTTCCATTCTCCGACTAAAAGG
CGACATTCACACTTACCAGGCTGAGAGGAGCCGTGGAGAAAAATCTTCGT
GTATATCATGTTATATGGAAGAGAATCCCGAGTCAACAGAGGAAGATGCA
ATCAATCATATCAACTCCATGGTCGACAAATTACTCAAGGAACTAAATTG
GGAGTATCTGAGACCTGATAGCAATGTTCCAATCACTTCCAAGAAACATG
CATTTGACATTCTGAGAGCTTTCTACCATCTCTACAAATACCGAGATGGCT
TCAGCGTTGCGAACTATGAAATAAAGAATTTGGTCATGACAACCGTCATT
GAGCCTG------------(SEQ ID NO:7)

P._sabiniana_MBO2
TCTAGCAAGGTTAAGGTTGTCCGCAGAACGATCTCAACTTCCATCCGCATG
TGTCGGATAACCACTGAATCCGGTGAAGGCGTACAGAGACGCATAGCAAA
TCATCATTCCAACCTCTGGGACGATAATTTCATACAGTCCCTCTCAACGCC
TTATGGGGCAATTTCGTACCATGAAAGTGCTCAGAACTTATTGGAGAAG
TAAAAGAGATGATCAATTCAATCTCGCTTAAAGATGGAGAATTAATCACC
CCCTCCAATGATCTCCTTATGCGGCTCTCTATAGTCGATAGCATTGAACGT
TTGGGAATCGATAGGCATTTCAAAAGTGAAATAAAATCAGCTCTGGATTA
TGTTTACAGTTATTGGAACGAAAAAGGCATTGGGTGGGAAGAGATAGTG
TTGTTGCCGATCTCAACTCAACTGCCTTGGGGCTTCGAACTCTACGACTAC
ACGGATACCCGGTGTCTTCAGATGTGTTACAACACTTCAAAGAACAAAAA
GGGCAGTTTGCATGTTCGGCCATTCAAACAGAGGGAGAGATAAGAAGTGT
TCTCAACTTATTTCGGGCTTCCCAAATTGCCTTTCCGGGAGAGAAAGTTAT
GGAAGAGGCAGAAGTCTTCTCTACAATATATTTAAAAGAAGCCATACTAA
AGCTTCCGGTCTGCGGTCTTTCACGAGAGATATCGTACGTTCTGGAATATG
GTTGGCATATAAATTTGCCAAGATTGGAAGCAAGGAACTACATCGACGTA
TTTGGAGAGGACCCCATTTATTTGACGCCAAATATGAAGACCCAAAAACT
TCTAGAACTTGCAAAGTTGGAGTTCAATATGTTTCACTCTTTACAACAGCA
AGAGCTAAAGCTTCTCTCCAGATGGTGGAAAGATTCGGGTTTCTCTCAAAT
GACCTTCCCTCGGCATCGTCACGTGGAATATTACACTTTGGCATCTTGCAT
TGATAGTGAACCTCAACATTCTTCGTTCAGACTTGGATTTGCCAAAATCTT
TCATCTTGCCACGGTTCTTGACGATATTTACGACACCTTTGGCACGATGGA
TGAGCTAGAACTCTTCACGGCGGCAGTTAAGAGGTGGCATCCGTCTGCGA
CGGAGTGGCTTCCAGAATATATGAAAGGAGTATATATGGTGCTTTACGAA
ACCGTTAACGAAATGGCAGGAGAAGCAGAAAAGTCTCAAGGCCGAGACA
CGCTCAACTATGGCCGAAATGCTTTGGAGGCTTATATTGATGCTTCTATGG
AAGAAGCGAAGTGGATTTTCAGTGGTTTTTGCCAACATTTGAGGAGTAC
CTGGATAACGGGAAAGTTAGTTTCGGTTATGGCATTGGCACATTGCAACC
CATTCTGACGTTGGGCATTCCCTTTCCTCATCACATCCTACAAGAAATAGA
CTTTCCTTCCAGGCTCAATGATGTGGCATCTTCCATTCTCCGACTAAAAGG
CGACATTCACACTTACCAGGCTGAGAGGAGCCGTGGAGAAAAATCTTCGT
GTATATCATGTTATATGGAAGAGAATCCCGAGTCAACAGAGGAAGATGCA

FIG.1F

ATCAATCATATCAACTCCATGGTCGACAAATTACTCAAGGAACTAAATTG
GGAGTATCTGAGACCTGATAGCAATGTTCCAATCACTTCCAAGAAACATG
CATTTGACATTCTGAGAGCTTTCTACCATCTCTACAAATACCGAGATGGCT
TCAGCGTTGCGAACTATGAAATAAAGAATTTGGTCATGACAACCGTCATT
GAGCCTGTGCCTTTATAAA (SEQ ID NO:8)

P._patula_MBO
TCTAGCAAGGTTAAGGTTGTCCGCAGAACGATCTCAACTTCCATCCGCATG
TGTCGGATAACTACTGTATCCGGTGAAGGCGTACAGAGACGCATAGCAAA
TCATCATTCCAACCTCTGGGACGATAATTTCATACAGTCCCTCTCAACGCC
TTATGGGGCAATTTCGTACCATGAAAGTGCTCAGAAACTTATTGGAGAAG
TAAAAGAGATGATCAATTCAATCTCGGTTAAAGATGGAGAATTAATCACC
CCCTCCAATGATCTCCTTATGCGGCTCTCTATAGTCGATAGCATTGAACGT
TTGGGAATCGATAGGCATTTCAAAAGTGAAATAAAATCAGCTCTGGATTA
TGTTTACAGTTATTGGAACGAAAAAGGCATTGGGTGGGAAGAGATAGTG
TTGTTGCCGATCTCAACTCAACTGCCTTGGGGCTTCGAACTCTACGACTAC
ACGGATACCCGGTGTCTTCAGATGTGTTACAACACTTCAAAGAACAAAAA
GGGCAGTTTGCATGTTCGGCCATTCAAACAGAGGGAGAGATAAGAAGTGT
TCTCAACTTATTTCGGGCTTCCCAAATTGCCTTTCCGGGAGAGAAAGTTAT
GGAAGAGGCAGAAGTCTTCTCTACAATATATTTAAAAGAAGCCATACTAA
AGCTTCCGGTCTGCGGTCTTTCACGAGAGATATCGTACGTTCTGGAATATG
GTTGGCATATAAATTTGCCAAGATTGGAAGCAAGGAACTACATCGACGTA
TTTGGACAGGACCCCATTTATTTGACGCCAAATATGAAGACCCAAAAACT
TCTAGAACTTGCAAAGTTGGAGTTCAATATGTTTCACTCTTTACAACAGCA
AGAGCTAAAGCTTCTCTCCAGATGGTGGAAAGATTCGGGTTTCTCTCAAAT
GACCTTCCCTCGGCATCGTCACGTGGAATATTACACTTTGGCATCTTGCAT
TGATAGTGAACCTCAACATTCTTCGTTCAGACTTGGATTTGCCAAAATATT
TCATCTTGCCACGGTTCTTGACGATATTTACGACACCTTTGGCACGATGGA
TGAGCTAGAACTCTTCACAGCGGCAGTTGAGAGGTGGCATCCGTCTGCGA
CGGAGTGGCTTCCAGAATATATGAAAGGAGTATATATGGTGCTTTACGAA
ACCGTTAACGAAATGGCAGGAGAAGCAGAAAAGTCTCAAGGCCGAGACA
CGCTCAACTATGCCCGAAATGCTTTGGAGGCTTATATTGATGCTTCTATGA
AAGAAGCGAAGTGGATTTTCAGTGGTTTTTGCCAACATTTGAGGAGTAC
CTGGATAACGGGAAAGTTAGTTTCGGTTATAGCATTGGCACATTGCAACC
CATTCTGACGTTGGGCATTCCCTTTCCTCATCACATCCTACAAGAAATAGA
CTTTCCTTCCAGGCTCAATGATGTGGCATGTTCCATTCTCCGACTAAAAGG
CGACATTCACACTTACCAGGCTGAGAGGAGCCGTGGAGAAAAATCTTCGT
GTATATCATGTTATATGGAAGAGAATCCCGAGTCAACAGAGGAAGATGCA
ATCGATCATATCAACTCCATGGTCGACAAATTACTCAAGGAACTAAATCG
GGAGTATCTGAGACCTGATAGCAATGTTCCAATCACTTCCAAGAAACATG
CATTTGACATTCTGAGAGCTTTCTACCATCTCTACAAATACCGAGATGGCT
TCAGCGTTGCGAACTATGAAATAAAGAATTTGGTCATGACAACCGTCATT
GAGCCTGTGCCTTTATAA-(SEQ ID NO:9)

P._montezumae_MBO
TCTAGCAAGGTTAAGGTTGTCCGCAGAACGATCTCAACTTCCATCCGCATG
TGTCGGATAACCACTGTATCCGGTG CCCTCCAATGATCTCCTTATGCGGCTCTCTATAGTCGATAGCATTGAACGT
TTGGGAATCGATAGGCATTTCAAAAGTGAAATAAAATCAGCTCTGGATTA
TGTTTACAGTTATTGGAACGAAAAAGGCATTGGGTGGGGAAGAGATAGTG
TTGTTGCCGATCTCAACTCAACTGCCTTGGGGCTTCGAACTCTACGACTAC
ACGGATACCCGGTGTCTTCAGATGTGTTACAGCACTTCAAAGAACAAAAA
GGGCAGTTTGCATGTTCGGCCATTCAAACAGAGGGAGAGATAAGAAGTGT
TCTCAACTTATTTCGGGCTTCCCAAATTGCCTTTCCGGGAGAGAAAGTTAT
GGAAGAGGCAGAAGTCTTCTCTACAATATATTTAAAAGAAGCCATACTAA
AGCTTCCGGTCTGCGGTCTTTCACGAGAGATATCGTACGTTCTGGAATATG
GTTGGCATATAAATTTGCCAAGATTGGAAGCAAGGAACTACATCGACGTA
TTTGGACAGGACCCCATTTATTTGACGCCAAATATGAAGACCCAAAAACT
TCTAGAACTTGCAAAGTTGGAGTTCAATATGTTTCACTCTTTACAACAGCA
AGAGCTAAAGCTTCTCTCCAGATGGTGGAAAGATTCGGGTTTCTCTCAAAT
GACCTTCCCTCGGCATCGTCACGTGGAATATTACACTTTGGCATCTTGCAT
TGATAGTGAACCTCAACATTCTTCGTTCAGACTTGGATTTGCCAAAATGTT
TCATCTTGCCACGGTTCTTGACGATATTTACGACACCTTTGGCACGATGGA
TGAGCTAGAACTCTTCACGGCGGCAGTTAAGAGGTGGCATCCGTCTGCGA
CGGAGTGGCTTCCAGAATATATGAAGGAGTATATATGGTGCTTTACGAA
ACCGTTAACGAAATGGCAGGAGAAGCAGAAAAGTCTCAAGGCCGAGACA
CGCTCAACTATGCCCGAAATGCTTTGGAGGCTTATATTGATGCTTCTATGA
AAGAAGCGAAGTGGATTTTCAGTGGTTTTTGCCAACATTTGAGGAGTAC
CTGGATAACGGGAAAGTTAGTTTCGGTTATAGCATTGGCACATTGCAACC
CATTCTGACGTTGGGCATTCCCTTTCCTCATCACATCCTACAAGAAATAGA
CTTTCCTTCCAGGCTCAATGATGTGGCATGTTCCATTCTCCGACTAAAAGG
CGACATTCACACTTACGAGGCTGAGAGGAGCCGTGGAGAAAAATCTTCGT
GTATATCATGTTATATGGAAGAGAATCCCGAGTCAACAGAGGAAGATGCA
ATCAATCATATCAACTCCATGGTCGACAAATTACTCAAGGAACTAAATTG
GGAGTATCTGAGACCTGATAGCAATGTTCCAATCACTTCCAAGAAACATG
CATTTGACATTCTGAGAGCTTTCTACCATCTCTACAAATACCGAGATGGCT
TCAGCGTTGCGAACTATGAAATAAAGAATTTGGTCATGACAACCGTCATT
GAGCCTGTGCCTTTATAA-(SEQ ID NO:10)

P._pseudostrobus_MBO--------------------------------------------------------------
AGACGCAKAGSTGRTYWYCATTCCAACCTYTGGGACGATAATTTCATACA
GTCCCTCTCAACGCCTTATGGGGCAATTTCGTACCATGAAAGTGCTCAGAA
ACTTATTGGAGAAGTAAAAGAGATGATCAATTCAATCTCGGTTAAAGATG
GAGAATTAATCACCCCCTCCAATGATCTCCTTATGCGGCTCTCTATAGTCG
ATAGCATTGAACGTTTGGGAATCGATAGGCATTTCAAAAGTGAAATAAAA
TCAGCTCTGGATTATGTTTACAGTTATTGGAACGAAAAAGGCATTGGGTG
GGGAAGAGATAGTGTTGTTGCCGATCTCAACTCAACTGCCTTGGGGCTTC
GAACTCTACGACTACACGGATACCCGGTGTCTTCAGATGTGTTACAGCACT
TCAAAGAACAAAAGGGCAGTTTGCATGTTCGGCCATTCAAACAGAGGGA
GAGATAAGAAGTGTTCTCAACTTATTTCGGGCTTCCCAAATTGCCTTTCCG
GGAGAGAAAGTTATGGAAGAGGCAGAAGTCTTCTCTACAATATATTTAAA
AGAAGCCATACTAAAGCTTCCGGTCTGCGGTCTTTCACGAGAGATATCGT
ACGTTCTGGAATATGGTTGGCATATAAATTTGCCAAGATTGGAAGCAAGG
AACTACATCGACGTATTTGGACAGGACCCCATTTATTTGACGCCAAATATG
AAGACCCAAAAACTTCTAGAACTTGCAAAGTTGGAGTTCAATATGTTTCA
CTCTTTACAACAGCAAGAGCTAAAGCTTCTCTCCAGATGGTGGAAAGATT
CGGGTTTCTCTCAAATGACCTTCCCTCGGCATCGTCACGTGGAATATTACA

FIG.1H

CTTTGGCATCTTGCATTGATAGTGAACCTCAACATTCTTCGTTCAGACTTG
GATTTGCCAAAATGTTTCATCTTGCCACGGTTCTTGACGATATTTACGACA
CCTTTGGCACGATGGATGAGCTAGAACTCTTCACGGCGGCAGTTAAGAGG
TGGCATCCGTCTGCGACGGAGTGGCTTCCAGAATATATGAAAGGAGTATA
TATGGTGCTTTACGAAACCGTTAACGAAATGGCAGGAGAAGCAGAAAAGT
CTCAAGGCCGAGACACGCTCAACTATGCCCGAAATGCTTTGGAGGCTTAT
ATTGATGCTTCTATGAAAGAAGCGAAGTGGATTTTCAGTGGTTTTTTGCCA
ACATTTGAGGAGTACCTGGATAACGGGAAAGTTAGTTTCGGTTATAGCAT
TGGCACATTGCAACCCATTCTGACGTTGGGCATTCCCTTTCCTCATCACAT
CCTACAAGAAATAGACTTTCCTTCCAGGCTCAATGATGTGGCATGTTCCAT
TCTCCGACTAAAAGGCGACATTCACACTTACGAGGCTGAGAGGAGCCGTG
GAGAAAAATCTTCGTGTATATCATGTTATATGGAAGAGAATCCCGAGTCA
ACAGAGGAAGATGCAATCAATCATATCAACTCCATGGTCGACAAATTACT
CAAGGAACTAAATTGGGAGTATCTGAGACCTGATAGCAATGTTCCAATCA
CTTCCAAGAAACATGCATTTGACATTCTGAGAGCTTTCTACCATCTCTACA
AATACCGAGATGGCTTCAGCGTTGCGAACTATGAAATAAAGAATTTGGTC
ATGACAACCGTCATTGAGCCTGTGCCTTTATAA- (SEQ ID NO:11)

P._coulteri_MBO------------------------------------------------------------------------------
AGACGCATAGCTGGTCATCATTCCAACCTYTGGGACGATRATTTSATACAG
TCCCTYTCAACGCCTTATGGGGCAATTTCGTACCATGAAAGTGCTCAGAA
ACTTATTGGAGAAGTAAAAGAGATGATCAATTCAATCTCGGTTAAAGATG
GAGAATTAATCACCCCCTCCAATGATCTCCTTATGCGGCTCTCTATAGTTG
ATAGCATTGAACGTTTGGGAATCGATAGGCATTTCAAAAGTGAAATAAAA
TCAGCTCTGGATTATGTTTACAGTTATTGGAACGAAAAAGGCATTGGGTG
GGGAAGAGATAGTGTTGTTGCCGATCTCAACTCAACTGCCTTGGGGCTTC
GAACTCTACGACTACACGGATACCCGGTGTCTTCAGATGTGTTACAACACT
TCAAAGAACAAAAAGGGCAGTTTGCATGTTCGGCCATTCAAACAGAGGGA
GAGATAAGAAGTGTTCTCAACTTATTTCGGGCTTCCCAAATTGCCTTTCCG
GGAGAGAAAGTTATGGAAGAGGCAGAAGTCTTCTCTACAATATATTTAAA
AGAAGCCATACTAAAGCTTCCGGTCTGCGGTCTTTCACGAGAGATATCGT
ACGTTCTGGAATATGGTTGGCATATAAATTTGCCAAGATTGGAAGCAAGG
AACTACATCGACGTATTTGGAGAGGACCCCATTTATTTGACGCCAAATAT
GAAGACCCAAAAACTTCTAGAACTTGCAAAGTTGGAGTTCAATATGTTTC
ACTCTTTACAACAGCAAGAGCTAAAGCTTCTCTCCAGATGGTGGAAAGAT
TCGGGTTTCTCTCAAATGACCTTCCCTCGGCATCGTCACGTGGAATATTAC
ACTTTGGCATCTTGCATTGATAGTGAACCTCAACATTCTTCGTTCAGACTT
GGATTTGCCAAAATCTTTCATCTTGCCACGGTTCTTGACGATATTTACGAC
ACCTTTGGCACGATGGATGAGCTAGAACTCTTCACGGCGGCAGTTAAGAG
GTGGCATCCGTCTGCGACGGAGTGGCTTCCAGAATATATGAAAGGAGTAT
ATATGGTGCTTTACGAAACCGTTAACGAAATGGCAGGAGAAGCAGAAAA
GTCTCAAGGCCGAGACACGCTCAACTATGGCCGAAATGCTTTGGAGGCTT
ATATTGATGCTTCTATGGAAGAAGCGAAGTGGATTTTCAGTGGTTTTTTGC
CAACATTTGAGGAGTACCTGGATAACGGGAAAGTTAGTTTCGGTTATGGC
ATTGGCACATTGCAACCCATTCTGACGTTGGGCATTCCCTTTCCTCATCAC
ATCCTACAAGAAATAGACTTTCCTTCCAGGCTCAATGATGTGGCATCTTCC
ATTCTCCGACTAAAAGGCGACATTCACACTTACCAGGCTGAGAGGAGCCG
TGGAGAAAAATCTTCGTGTATATCATGTTATATGGAAGAGAATCCCGAGT
CAACAGAGGAAGATGCAATCAATCATATCAACTCCATGGTCGACAAATTA
CTCAAGGAACTAAATTGGGAGTATCTGAGACCTGATAGCAATGTTCCAAT

FIG.1I

CACTTCCAAGAAACATGCATTTGACATTCTGAGAGCTTTCTACCATCTCTA
CAAATACCGAGATGGCTTCAGCGTTGCGAACTATGAAATAAAGAATTTGG
TCATGACAACCGTCATTGAGCCTGTGCCTTTATAA- (SEQ ID NO:12)

P._torreyana_MBO----------------------------------------------------------------------------
AACCTCTGGGACGATGATTTGATACAGTCCCTTTCAACGCCTTATGGGGCA
ATTTCGTACCATGAAAGTGCTCAGAAACTTATTGGAGAAGTAAAAGAGAT
GATCAATTCAATCTCGGTTAAAGATGGAGAATTAATCACCCCCTCCAATG
ATCTCCTTATGCGGCTCTCTATAGTTGATAGCATTGAACGTTTGGGAATCG
ATAGGCATTTCAAAAGTGAAATAAAATCAGCTCTGGATTATGTTTACAGTT
ATTGGAACGAAAAAGGCATTGGGTGGGGAAGAGATAGTGTTGTTGCCGAT
CTCAACTCAACTGCCTTGGGGCTTCGAACTCTACGACTACACGGATACCCG
GTGTCTTCAGATGTGTTACAACACTTCAAAGAACAAAAGGGCAGTTTGC
ATGTTCGGCCATTCAAACAGAGGGAGAGATAAGAAGTGTTCTCAACTTAT
TTCGGGCTTCCCAAATTGCCTTTCCGGGAGAGAAAGTTATGGAAGAGGCA
GAAGTCTTCTCTACAATGTATTTAAAAGAAGCCATACTAAAGCTTCCGGTC
TGCGGTCTTTCACGAGAGATATCGTACGTTCTGGAATATGGTTGGCATATA
AATTTGCCAAGATTGGAAGCAAGGAACTACATCGACGTATTTGGACAGGA
CCCCATTTATTTGACGCCAAATATGAAGACCCAAAAACTTCTAGAACTTGC
AAAGTTGGAGTTCAATATGTTTCACTCTTTACAACAGCAAGAGCTAAAGC
TTCTCTCCAGATGGTGGAAAGATTCGGGTTTCTCTCAAATGACCTTCCCTC
GGCATCGTCACGTGGAATATTACACTTTGGCATCTTGCATTGATAGTGAAC
CTCAACATTCTTCGTTCAGACTTGGATTTGCCAAAATCTTTCATCTTGCCAC
GGTTCTTGACGATATTTACGACACCTTTGGCACGATGGATGAGCTAGAACT
CTTCACGGCGGCAGTTAAGAGGTGGCATCCGTCTGCGACGGAGTGGCTTC
CAGAATATATGAAAGGAGTATATATGGTGCTTTACGAAACCGTTAACGAA
ATGGCAGGAGAAGCAGAAAAGTCTCAAGGCCGAGACACGCTCAACTATG
CCCGAAATGCTTTGGAGGCTTATATTGATGCTTCTATGGAAGAAGCGAAG
TGGATTTTCAGTGGTTTTTTGCCAACATTTGAGGAGTACCTGGATAACGGG
AAAGTTAGTTTCGGTTATGGCATTGGCACATTGCAACCCATTCTGACGTTG
GGCATTCCCTTTCCTCATCACATCCTACAAGAAATAGACTTTCCTTCCAGG
CTCAATGATGTGGCATCTTCCATTCTCCGACTAAAAGGCGACATTCACACT
TACCAGGCTGAGAGGAGCCGTGGAGAAAAATCTTCGTGTATATCATGTTA
TATGGAAGAGAATCCCGAGTCAACAGAGGAAGATGCAATCAATCATATCA
ACTCCATGGTCGACAAATTACTCAAGGAACTAAATTGGGAGTATCTGAGA
CCTGATAGCAATGTTCCAATCACTTCCAAGAAACATGCATTTGACATTCTG
AGAGCTTTCTACCATCTCTACAAATACCGAGATGGCTTCAGCGTTGCGAAC
TATGAAATAAAGAATTTGGTCATGACAACCGTCATTGAGCCTGTGCCTTTA
TAA- (SEQ ID NO:13)

P._attenuata_MBO----------------------------------------------------------------------------
AGACGCAGAGGTGATTTCCATTCCAACCTCTGGGACGATAATTTCATACA
GTCCCTCTCAACGCCTTATGGGGCAATTTCGTACCATGAAAGTGCTCAGAA
ACTTATTGGAGAAGTAAAAGAGATGATCAATTCAATCTCGGATAAAGATG
GAGAATTAATCACCCCCTCCAATGATCTCCTTATGCTGCTCTCTATAGTCG
ATAGCATTGAACGTTTGGGAATCGATAGGCATTTCAAAAGTGAAATAAAA
TCAGCTCTGGATTATGTTTACAGTTATTGGAACGAAAAAGGCATTGGGTG
GGGAAGAGATAGTGTTGTTGCCGATCTCAACTCAACTGCCTTGGGGCTTC
GAACTCTACGACTACACGGATACCCGGTGTCTTCAGACGTGTTACAACAC
TTCAAAGAACAAAATGGGCAGTTTGCATGTTCGGCCATTCAAACAGAGGG

FIG.1J

AGAGATAAGAAGTGTTCTCAACTTATTTCGGGCTTCCCAAATTGCCTTTCC
GGGAGAGAAAGTTATGGAAGAGGCAGAAGTCTTCTCTACAAAATATTTAA
AAGAAGCCATACTAAAGCTTCCGGTCTGCGGTCTTTCACGAGAGATATCG
TACGTTCTGGAATATGGTTGGCATATGAATTTGCCAAGATTGGAAGCAAG
GAACTACATCGACGTATTTGGACAGGACCCCATTTATTTGACGCCAAATAT
GAAGACCCAAAAACTTCTAGAACTTGCAAAGTTGGAGTTCAATATGTTTC
ACTCTTTACAACAGCAAGAGCTAAAGCTTCTCTCCAGATGGTGGAAAGAT
TCGGGTTTCTCTCAAATGACCTTCCCTCGGCATCGTCACGTGGAATATTAC
ACTTTGGCATCTTGCATTGATAGTGAACCTCAACATTCTTCGTTCAGACTT
GGATTTGCCAAAATATTTCATCTTGCCACGGTTCTTGACGATATTTACGAC
ACCTTTGGCACGATGGATGAGCTAGAACTCTTCACAGCGGCAGTTAAGAG
GTGGCATCCGTCTGCGACGGAGTGGCTTCCAGAATATATGAAAGGAGTAT
ATATGGTGCTTTACGAAACCGTTAACGAAATGGCAGGAGAAGCAGAAAA
GTCTCAAGGCCGAGACACGCTCAACTATGCCCGAAATGCTTTGGAGGCTT
ATATTGATGCTTCTATGGAAGAAGCGAAGTGGATTTTCAGTGGTTTTTGC
CAACATTTGAGGAGTACCTGGATAACGGGAAAGTTAGTTTCGGTTATACC
ATTGGCACATTGCAACCCATTCTGACGTTGGGCATTCCCTTTCCTCATCAC
ATCCTACAAGAAATAGACTTTCCTTCCAGGCTCAATGATGTGGCATGTTCC
ATTCTCCGACTAAAAGGCGACGTTCACACTTACCAGCCTGAGAGGAGCCG
TGGAGAAGAATCTTCGTGTATATCATGTTATATTGAAGAGAATCCCGAGT
CAACAGAGGAAGATGCAATCAATCATATCAACTCCATGGTCGACAAATTA
CTCAAGGAACTAAATTGGGAGTATCTGAGACCTGATAGCAATGTTCCAAT
CACTTCCAAGAAACATGCATTTGACATTCTGAGAGCTTTGTACCATCTCTA
CAAATACCGAGATGGCTACAGCGTTGCGAACTATGAAATAAAGAATTTGG
TCATGACAACCGTCATTGAGCCTGTGCCTTTATAA- (SEQ ID NO:14)

P._radiata_MBO------------------------------------------------------------------------------
AACCTCTGGGACGATGATTTGATACAGTCCCTTTCAACGCCTTATGGGGCA
ATTTCGTACCATGAAAGTGCTCAGAAACTTATTGGAGAAGTAAAAGAGAT
GATCAATTCAATCTCGGATAAAAATGGAGAATTAATCACCCCCTCCAATG
ATCTCCTTATGCGGCTCTCTATAGTCGATAGCATTGAACGTTTGGGAATCG
ATAGGCATTTCAAAAGTGAAATAAAATCAGCTCTGGATTATGTTTACAGTT
ATTGGAACGAAAAAGGCATTGGGTGGGGAAGAGATAGTGTTGTTGCCGAT
CTCAACTCAACTGCCTTGGGGCTTCGAACTCTACGACTACACGGATACCCG
GTGTCTTCAGACGTGTTACAACACTTCAAAGAACAAAATGGGCAGTTTGC
ATGTTCGGCCATTCAAACAGAGGGAGAGATAAGAAGTGTTCTCAACTTAT
TTCGGGCTTCCCAAATTGCCTTTCCGGGAGAGAAAGTTATGGAAGAGGCA
GAAGTCTTCTCTACAAAATATTAAAAGAAGCCATACTAAAGCTTCCGGT
CTGCGGTCTTTCACGAGAGATATCGTACGTTCTGGAATATGGTTGGCATAT
GAATTTGCCAAGATTGGAAGCAAGGAACTACATCGACGTATTTGGACAGG
ACCCCATTTATTTGACGCCAAATATGAAGACCCAAAAACTTCTAGAACTT
GCAAAGTTGGAGTTCAATATGTTTCACTCTTTACAACAGCAAGAGCTAAA
GCTTCTCTCCAGATGGTGGAAAGATTCGGGTTTCTCTCAAATGACCTTCCC
TCGGCATCGTCACGTGGAATATTACACTTTGGCATCTTGCATTGATAGTGA
ACCTCAACATTCTTCGTTCAGACTTGGATTTGCCAAAATATTTCATCTTGC
CACGGTTCTTGACGATATTTACGACACCTTTGGCACGATGGATGAGCTAG
AACTCTTCACAGCGGCAGTTAAGAGGTGGCATCCGTCTGCGACGGAGTGG
CTTCCAGAATATATGAAGGAGTATATATGGTGCTTTACGAAACCGTTAA
CGAAATGGCAGGAGAAGCAGAAAAGTCTCAAGGCCGAGACACGCTCAAC
TATGCCCGAAATGCTTTGGAGGCTTATATTGATGCTTCTATGGAAGAAGCG

FIG.1K

AAGTGGATTTTCAGTGGTTTTTGCCAACATTTGAGGAGTACCTGGATAAC
GGGAAAGTTAGTTTCGGTTATACCATTGGCACATTGCAACCCATTCTGACG
TTGGGCATTCCCTTTCCTCATCACATCCTACAAGAAATAGACTTTCCTTCC
AGGCTCAATGATGTGGCATGTTCCATTCTCCGACTAAAAGGCGACGTTCA
CACTTACCAGCCTGAGAGGAGCCGTGGAGAAGAATCTTCGTGTATATCAT
GTTATATGGAAGAGAATCCCGAGTCAACAGAGGAAGATGCAATCAATCAT
ATCAACTCCATGGTCGACAAATTACTCAAGGAACTAAATTGGGAGTATCT
GAGACCTGATAGCAATGTTCCAATCACTTCCAAGAAACATGCATTTGACA
TTCTGAGAGCTTTGTACCATCTCTACAAATACCGAGATGGCTACAGCGTTG
CGAACTATGAAATAAAGAATTTGGTCATGACAACTGTCATTGAGCCTGTG
CCTTTATAA- (SEQ ID NO:15)

P._contorta_MBO1
TCTAGCAAGGTTAAGGTTGTCCGCAGAACGATGTCAACTTCCATCCGCAT
GTGTCAGATAACCACTGTATCCGGTGAAGGCGTACAGAGACGCATAGCAA
ATCATCATTCCAACCTCTGGGACGATAATTTCATACAGTCCCTCTCAACGC
CTTATGGGGCAATTTCGTACCATGAAAGTGCTCAGAAACTTATTGGAGAA
GTAAAAGAGATGATCAATTCAATCTCGGTTAAAGATGGAGAATTAATCAC
CCCCTCCAATGATCTCCTTATGCGGCTCTCTATAGTCGATAGCATTGAACG
TTTGGGAATCGATAGGCATTTCAAAAGTGAAATAAAATCAGCTCTGGATT
ATGTTTACAGTTATTGGAACGAAAAAGGCATTGGGTGGGAAGAGATAGT
GTTGTTGCCGATCTCAACTCAACTGCCTTGGGGCTTCGAACTCTACGACTA
CACGGATACCCGGTGTCTTCAGACGTGTTACAACACTTCAAAGAACAAAA
AGGGCAGTTTGCATGTTCGGCCATTCAAACAGAGGGAGAGATAAGAAGTG
TTCTCAACTTATTTCGGGCTTCCCAAATTGCCTTTCCGGGAGAGAAAGTTA
TGGAAGAGGCAGAAGTCTTCTCTACAAAATATTTAAAAGAAGCCATACTA
AAGCTTCCGGTCTGCGGTCTTTCACGAGAGATATCGTACGTTCTGGAATAT
GGTTGGCATATGAATTTGCCAAGATTGGAAGCAAGGAACTACATCGACGT
ATTTGGACAGGACCCCATTTATTTGACGCCAAATATGAAGACCCAAAAAC
TTCTAGAACTTGCTAAGTTGGAGTTCAATATGTTTCACTCTTTACAACAGC
AAGAGCTAAAGCTTCTCTCCAGATGGTGGAAAGATTCGGGTTTCTCTCAA
ATGACCTTCCCTCGGCATCGTCACGTGGAATATTACACTTTGGCATCTTGC
ATTGATAGTGAACCTCAACATTCTTCGTTCAGACTTGGATTTGCCAAAATA
TTTCATCTTGCCACGGTTCTTGACGATATTACGACACCTTTGGCACGATG
GATGAGCTAGAACTCTTCACAGCGGCAGTTAAGAGGTGGCATCCGTCTGC
GACGGAGTGGCTTCCAGAATATATGAAGGAGTATATATGGTGCTTTACG
AAACCGTTAACGAAATGGCAGGAGAAGCAGAAAGTCTCAAGGCCGAGA
CACGCTCAACTATGCCCGAAATGCTTTGGAGGCTTATATTGATGCTTCTAT
GGAAGAAGCGAAGTGGATTTTCAGTGGTTTTTGCCAACATTTGAGGAGT
ACCTGGATAACGGGAAAGTTAGTTTCGGTTATACCATTGGCACATTGCAA
CCCATTCTGACGTTGGGCATTCCCTTTCCTCATCACATCCTACAAGAAATA
GACTTTCCTTCCAGGCTCAATGATGTGGCATGTTCCATTCTCCGACTAAAA
GGCGACATTCACACTTACCAGCCTGAGAGGAGCCGTGGAGAAGAATCTTC
GTGTATATCATGTTATATGGAAGATAATCCCGAGTCAACAGAGGAAGATG
CAATCAATCATATCAACTCCATGGTCGACAAATTACTCAAGGAACTAAAT
TGGGAGTATCTGAGACCTGATAGCAATGTTCCAATCACTTCCAAGAAACA
TGCATTTGACATTCTGAGAGCTTTCTACCATCTCTACAAATACCGAGATGG
CTACAGCGTTGCGAACTATGAAATAAAGAATTTGGTCATGACAACTGTCA
TTGAGCCTGTGCCTTTATAA- (SEQ ID NO:16)

FIG.1L

P._contorta_MB02
TCTAGCAAGGTTAAGGTTGTCCGCAGAACGATGTCAACTTCCATCCGCAT
GTGTCAGATAACCACTGTATCCGGTGAAGGCGTACAGAGACGCATAGCAA
ATCATCATTCCAACCTCTGGGACGATAATTTCATACAGTCCCTCTCAACGC
CTTATGGGGCAATTTCGTACCATGAAAGTGCTCAGAAACTTATTGGAGAA
GTAAAAGAGATGATCAATTCAATCTCGGTTAAAGATGGAGAATTAATCAC
CCCGTCCAATGATCTCCTTATGCGGCTCTCTATAGTCGATAGCATTGAACG
TTTGGGAATCGATAGGCATTTCAAAAGTGAAATAAAATCAGCTCTGGATT
ATGTTTACAGTTATTGGAACGAAAAAGGCATTGGGTGGGGAAGAGATAGT
GTTGTTGCCGATCTCAACTCAACTGCCTTGGGGCTTCGAACTCTACGACTA
CACGGATACCCGGTGTCTTCAGACGTGTTACAACACTTCAAAGAACAAAA
AGGGCAGTTTGCATGTTCGGCCATTCAAACAGAGGGAGAGATAAGAAGTG
TTCTCAACTTATTTCGGGCTTCCCAAATTGCCTTTCCGGGAGAGAAAGTTA
TGGAAGAGGCAGAAGTCTTCTCTACAAAATATTTAAAAGAAGCCATACTA
AAGCTTCCGGTCTGCGGTCTTTCACGAGAGATATCGTACGTTCTGGAATAT
GGTTGGCATATAAATTTGCCAAGATTGGAAGCAAGGAACTACATCGACGT
ATTTGGACAGGACCCCATTTATTTGACGCCAAATATGAAGACCCAAAAAC
TTCTAGAACTTGCAAAGTTGGAGTTCAATATGTTTCACTCTTTACAACAGC
AAGAGCTAAAGCTTCTCTCCAGATGGTGGAAAGATTCGGGTTTCTCTCAA
ATGACCTTCCCTCGGCATCGTCACGTGGAATATTACACTTTGGCATCTTGC
ATTGATAGTGAACCTCAACATTCTTCGTTCAGACTTGGATTTGCCAAAATA
TTTCATCTTGCCACGGTTCTTGACGATATTTACGACACCTTTGGCACGATG
GATGAGCTAGAACTCTTCACAGCGGCAGTTAAGAGGTGGCATCCGTCTGC
GACGGAGTGGCTTCCAGAATATATGAAAGGAGTATATATGGTGCTTTACG
AAACCGTTAACGAAATGGCAGGAGAAGCAGAAAAGTCTCAAGGCCGAGA
CACGCTCAACTATGCCCGAAATGCTTTGGAGGCTTATATTGATGCTTCTAT
GGAAGAAGCGAAGTGGATTTTCAGTGGTTTTTTGCCAACATTTGAGGAGT
ACCTGGATAACGGGAAAGTTAGTTTCGGTTATACCATTGGCACATTGCAA
CCCATTCTGACGTTGGGCATTCCCTTTCCTCATCACATCCTACAAGAAATA
GACTTTCCTTCCAGGCTCAATGATGTGGCATGTTCCATTCTCCGACTAAAA
GGCGACGTTCACACTTACCAGGCTGAGAGGAGCCGTGGAGAAGAATCTTC
GTGTATATCATGTTATATGGAAGATAATCCCGAGTCAACAGAGGAAGATG
CAATCAATCATATCAACTCCATGGTCGACAAATTACTCAAGGAACTAAAT
TGGGAGTATCTGAGACCTGATAGCAATGTTCCAATCACTTCCAAGAAACA
TGCATTTGACATTCTGAGAGCTTTCTACCATCTCTACAAATACCGAGATGG
CTACAGCGTTGCGAACTATGAAATAAAGAATTTGGTCATGACAACTGTCA
TTGAGCCTGTGCCTTTATAA-(SEQ ID NO:17)

FIG. 1M

P._patula_MBO_translation_frame_+1
SSKVKVVRRTISTSIRMCRITTVSGEGVQRRIANHHSNLWDDNFQSLSTPYGA
ISYHESAQKLIGEVKEMINSISVKDGELITPSNDLLMRLSIVDSIERLGIDRHFKS
EIKSALDYVYSYWNEKGIGWGRDSVVADLNSTALGLRTLRLHGYPVSSDVL
QHFKEQKGQFACSAIQTEGEIRSVLNLFRASQIAFPGEKVMEEAEVFSTIYLKE
AILKLPVCGLSREISYVLEYGWHINLPRLEARNYIDVFGQDPIYLTPNMKTQKL
LELAKLEFNMFHSLQQQELKLLSRWWKDSGFSQMTFPRHRHVEYYTLASCID
SEPQHSSFRLGFAKIFHLATVLDDIYDTFGTMDELELFTAAVERWHPSATEWL
PEYMKGVYMVLYETVNEMAGEAEKSQGRDTLNYARNALEAYIDASMKEAK
WIFSGFLPTFEEYLDNGKVSFGYSIGTLQPILTLGIPFPHHILQEIDFPSRLNDVA
CSILRLKGDIHTYQAERSRGEKSSCISCYMEENPESTEEDAIDHINSMVDKLLK
ELNREYLRPDSNVPITSKKHAFDILRAFYHLYKYRDGFSVANYEIKNLVMTTV
IEPVPL(SEQ ID NO:18)

P._pseudostrobus_estevezii_translation_frame_+1
SSKVKVVRRTISTSIRMCRITTVSGEGVQRRIANHHSNLWDDNFQSLSTPYGA
ISYHESAQKLIGEVKEIINSISVKDGELITPSNDLLMRLSIVDSIERLGIDRHFKSE
IKSALDYVYSYWNEKGIGWGRDSVVADLNSTALGLRTLRLHGYPVSSDVLQ
HFKEQKGQFACSAIQTEGEIRSVLNLFRASQIAFPGEKVMEEAEVFSTIYLKEA
ILKLPVCGLSREISYVLEYGWHINLPRLEARNYIDVFGQDPIYLTPNMKTQKLL
ELAKLEFNMFHSLQQQELKLLSRWWKDSGFSQMTFPRHRHVEYYTLASCIDS
EPQHSSFRLGFAKIFHLATVLDDIYDTFGTMDELELFTAAVKRWHPSATEWLP
EYMKGVYMVLYETVNEMAGEAEKSQGRDTLNYARNALEAYIDASMKEAK
WIFSGFLPTFEEYLDNGKVSFGYSIGTLQPILTLGIPFPHHILQEIDFPSRLNDVA
CSILRLKGDIHTYQAERSRGEKSSCISCYMEENPESTEEDAINHVNSMVDKLL
KELNWEYLRPDSNVPITSKKHAFDILRAFYHLYKYRDGFSVANYEIKNLVMT
TVIEPVPL (SEQ ID NO:19)

P_cooperi_ornelasi_MBO_translation_frame_+1
SSKVKVVRRTISTSIRMCRITTVSGEGVQRRIANHHSNLWDDNFQSLSTPYGA
ISYHESAQKLIGEVKEMINSISVKDGELITPSNDLLMRLSIVDSIERLGIDRHFKS
EIKSALDYVYSYWNEKGIGWGRDSVVADLNSTALGLRTLRLHGYPVSSDVL
QHFKEQKGQFACSAIQTEGEIRSVLNLFRASQIAFPGEKVMEEAEVFSTIYLKE
AILKLPVCGLSREISYVLEYGWHINLPRLEARNYIDVFGQDPIYLTPNMKTQKL
LELAKLEFNMFHSLQQQELKLLSRWWKDSGFSQMTFPRHRHVEYYTLASCID
SEPQHSSFRLGFAKIFHLATVLDDIYDTFGTMDELELFTAAVKRWHPSATEWL
PEYMKGVYMVLYETVNEMAGEAEKSQGRDTLNYARNALEAYIDASMKEAK
WIFSGFLPTFEEYLDNGKVSFGYSIGTLQPILTLGIPFPHHILQEIDFPSRLNDVA
CSILRLKGDIHTYQAERSRGEKSSCISCYMEENPESTEEDAINHINSMVDKLLK
ELNWEYLRPDSNVPITSKKHAFDILTAFYHLYKYRDGFSVANYEIKNLVMTT
VIEPVPL (SEQ ID NO:20)

P._hartwegii_MBO_translation_frame_+1
SSKVKVVRRTISTSIRMCRITTVSGEGVQRRIANHHSNLWDDNFQSLSTPYGA
ISYHESAQKLIGEVKEMINSISVKDGELITPSNDLLMRLSIVDSIERLGIDRHFKS
EIKSALDYVYSYWNEKGIGWGRDSVVADLNSTALGLRTLRLHGYPVSSDVL
QHFKEQKGQFACSAIQTEGEIRSVLNLFRASQIAFPGEKVMEEAEVFSTIYLKE

FIG.2A

AILKLPVCGLSREISYVLEYGWHINLPRLEARNYIDVFGQDPIYLTPNMKTQKL
LELAKLEFNMFHSLQQQELKLLSRWWKDSGFSQMTFPRHRHVEYYTLASCID
SEPQYSSFRLGFAKIFHLATVLDDIYDTFGTMDELELFTAAVKRWHPSATEWL
PEYMKGVYMVLYETVNEMAGEAEKSQGRDTLNYARNALEAYIDASMKEAK
WIFSGFLPTFEEYLDNGKVSFGYSIGTLQPILTLGIPFPHHILQEIDFPSRLNDVA
CSILRLKGDIHTYQAERSRGEKSSCISCYMEENPESTEEDAINIINSMVDKLLK
ELNWEYLRPDSNVPITSKKHAFDILRAFYHLYKYRDGFSVANYEIKNLVMTT
VIEPVPL (SEQ ID NO:21)

P._ponderosa_MBO1_translation_frame_+1
SSKVKVVRRTISTSIRMCRITTESGEGVQRRIANHHSNLWDDNFIQSLSTPYGA
ISYHESAQKLIGEVKEMINSISLKDGELITPSNDLLMRLSIVDSIERLGIDRHFKS
EIKSALDYVYSYWNEKGIGWGRDSVVADLNSTALGLRTLRLHGYPVSSDVL
QHFKEQKGQFACSAIQTEGEIRSVLNLFRASQIAFPGEKVMEEAEVFSTIYLKE
AILKLPVCGLSREISYVLEYGWHINLPRLEARNYIDVFGQDPIYLTPNMKTQKL
LELAKLEFNMFHSLQQQELKLLSRWWKDSGFSQMTFPRHRHVEYYTLASCID
SEPQHSSFRLGFAKIFHLATVLDDIYDTFGTMDELELFTAAVKRWHPSATEWL
PEYMKGVYMVLYETVNEMAREAEKSQGRDTLNYARNALEAYIDASMKEAK
WIFSGFLPTFEEYLDNGKVSFGYSIGTLQPILTLGIPFPHHILQEIDFPSRLNDVA
CSILRLKGDIHTYQAERSRGEKSSCISCYMEENPESTEEDAINHINSMVDKLLK
ELNWEYLRPDSNVPITSKKHAFDILRTFYHLYKYRDGFSVANYEIKNLVMTT
VIEPVPL (SEQ ID NO:22)

P._ponderosa_MBO2_translation_frame_+1
SSKVKVVRRTISTSIRMCRITTESGEGVQRRIANHHSNLWDDNFIQSLSTPYGA
ISYHESAQKLIGEVKEMINSISLKDGELITPSNDLLMRLSIVDSIERLGIDRHFKS
EIKSALDYVYSYWNEKGIGWGRDSVVADLNSTALGLRTLRLHGYPVSSDVL
QHFKEQKGQFACSAIQTEGEIRSVLNLFRASQIAFPGEKVMEEAEVFSTIYLKE
AILKLPVCGLSREISYVLEYGWHINLPRLEARNYIDVFGQDPIYLTPNMKTQKF
LELAKLEFNMFHSLQQQELKLLSRWWKDSGFSQMTFPRHRHVEYYTLASCID
SEPQHSSFRLGFAKIFHLATVLDDIYDTFGTMDELELFTAAVKRWHPSATEWL
PEYMKGVYMVLYETVNEMAREAEKSQGRDTLNYARNALEAYIDASMKEAK
WIFSGFLPTFEEYLYNGKVSFGYSIGTLQPILTLGIPFPHHILQEIDFPSRLNDVA
CSILRLKGDIHTYQAERSRGEKSSCISCYMEENPESTEEDAINHINSMVDKLLK
ELNWEYLRPDSNVPITSKKHAFDILRTFYHLYKYRDGFSVANYEIKNLVMTT
VIEPVPL (SEQ ID NO:23)

P._jeffreyi_MBO_translation_frame_+1
SSKVKVVRRTISTSIRMCRITTESGEGVQRRIANHHSNLWDDNFIQSLSTPYGA
ISYHESAQKLIGEVKEMINSISLKDGELITPSNDLLMRLSIVDSIERLGIDRHFKS
EIKSALDYVYSYWNEKGIGWGRDSVVADLNSTALGLRTLRLHGYPVSSDVL
QHFKEQKGQFACSAIQTEGEIRSVLNLFRASQIAFPGEKVMEEAEVFSTIYLKE
AILKLPVCGLSREISYVLEYGWHINLPRLEARNYIDVFGQDPIYLTPNMKTQKL
LELAKLEFNMFHSLQQQELKLLSRWWKDSGFSQMTFPRHRHVEYYTLASCID
SEPQHSSFRLGFAKIFHLATVLDDIYDTFGTMDELELFTAAVKRWHPSATEWL
PEYMKGVYMVLYETVNEMAGEAEKSQGRDTLNYARNASEAYIDASMKEAK
WIFSGFLPTFEEYLDNGKVSFGYSIGTLQPILTLGIPFPHHILQEIDFPSRLNDVA
CSILRLKGDIHTYQAERSRGEKSSCISCYMEENPESTEEDAINHINSMVDKLLK
ELNWEYLRPDSNVPITSKKHAFDILRAFYHLYKYRDGFSVANYEIKNLVMTT
VIEPVPL (SEQ ID NO:24)

FIG. 2B

P._montezumae_MBO_translation_frame_+1
SSKVKVVRRTISTSIRMCRITTVSGEGVQRRIANHHSNLWDDNFIQSLSTPYGA
ISYHESAQKLIGEVKEMINSISVKDGELITPSNDLLMRLSIVDSIERLGIDRHFKS
EIKSALDYVYSYWNEKGIGWGRDSVVADLNSTALGLRTLRLHGYPVSSDVL
QHFKEQKGQFACSAIQTEGEIRSVLNLFRASQIAFPGEKVMEEAEVFSTIYLKE
AILKLPVCGLSREISYVLEYGWHINLPRLEARNYIDVFGQDPIYLTPNMKTQKL
LELAKLEFNMFHSLQQQELKLLSRWWKDSGFSQMTFPRHRHVEYYTLASCID
SEPQHSSFRLGFAKMFHLATVLDDIYDTFGTMDELELFTAAVKRWHPSATEW
LPEYMKGVYMVLYETVNEMAGEAEKSQGRDTLNYARNALEAYIDASMKEA
KWIFSGFLPTFEEYLDNGKVSFGYSIGTLQPILTLGIPFPHHILQEIDFPSRLNDV
ACSILRLKGDIHTYEAERSRGEKSSCISCYMEENPESTEEDAINHINSMVDKLL
KELNWEYLRPDSNVPITSKKHAFDILRAFYHLYKYRDGFSVANYEIKNLVMT
TVIEPVPL (SEQ ID NO:25)

P._pseudostrobus_MBO_translation_frame_+1    ------------------------------
RRXXXXHSNLWDDNFIQSLSTPYGAISYHESAQKLIGEVKEMINSISVKDGELI
TPSNDLLMRLSIVDSIERLGIDRHFKSEIKSALDYVYSYWNEKGIGWGRDSVV
ADLNSTALGLRTLRLHGYPVSSDVLQHFKEQKGQFACSAIQTEGEIRSVLNLF
RASQIAFPGEKVMEEAEVFSTIYLKEAILKLPVCGLSREISYVLEYGWHINLPR
LEARNYIDVFGQDPIYLTPNMKTQKLLELAKLEFNMFHSLQQQELKLLSRWW
KDSGFSQMTFPRHRHVEYYTLASCIDSEPQHSSFRLGFAKMFHLATVLDDIYD
TFGTMDELELFTAAVKRWHPSATEWLPEYMKGVYMVLYETVNEMAGEAEK
SQGRDTLNYARNALEAYIDASMKEAKWIFSGFLPTFEEYLDNGKVSFGYSIGT
LQPILTLGIPFPHHILQEIDFPSRLNDVACSILRLKGDIHTYEAERSRGEKSSCISC
YMEENPESTEEDAINHINSMVDKLLKELNWEYLRPDSNVPITSKKHAFDILRA
FYHLYKYRDGFSVANYEIKNLVMTTVIEPVPL (SEQ ID NO:26)

P._sabiniana_MBO1_translation_frame_+1
SSKVKVVRRTISTSIRMCRITTESGEGVQRRIANHHSNLWDDNFIQSLSTPYGA
ISYHESAQKLIGEVKEMINSISVKDGELITPSNDLLMRLSIVDSIERLGIDRHFKS
EIKSALDYVYSYWNEKGIGWGRDSVVADLNSTALGLRTLRLHGYPVSSDVL
QHFKEQKGQFACSAIQTEGEIRSVLNLFRASQIAFPGEKVMEEAEVFSTIYLKE
AILKLPVCGLSREISYVLEYGWHINLPRLEARNYIDVFGEDPIYLTPNMKTQKL
LELAKLEFNMFHSLQQQELKLLSRWWKDSGFSQMTFPRHRHVEYYTLASCID
SEPQHSSFRLGFAKIFHLATVLDDIYDTFGTMDELELFTAAVKRWHPSATEWL
PEYMKGVYMVLYETVNEMAGEAEKSQGRDTLNYGRNALEAYIDASMEEAK
WIFSGFLPTFEEYLDNGKVSFGYGIGTLQPILTLGIPFPHHILQEIDFPSRLNDVA
SSILRLKGDIHTYQAERSRGEKSSCISCYMEENPESTEEDAINHINSMVDKLLK
ELNWEYLRPDSNVPITSKKHAFDILRAFYHLYKYRDGFSVANYEIKNLVMTT
VIEP--- (SEQ ID NO:27)

P._sabiniana_MBO2_translation_frame_+1
SSKVKVVRRTISTSIRMCRITTESGEGVQRRIANHHSNLWDDNFIQSLSTPYGA
ISYHESAQKLIGEVKEMINSISLKDGELITPSNDLLMRLSIVDSIERLGIDRHFKS
EIKSALDYVYSYWNEKGIGWGRDSVVADLNSTALGLRTLRLHGYPVSSDVL
QHFKEQKGQFACSAIQTEGEIRSVLNLFRASQIAFPGEKVMEEAEVFSTIYLKE
AILKLPVCGLSREISYVLEYGWHINLPRLEARNYIDVFGEDPIYLTPNMKTQKL
LELAKLEFNMFHSLQQQELKLLSRWWKDSGFSQMTFPRHRHVEYYTLASCID
SEPQHSSFRLGFAKIFHLATVLDDIYDTFGTMDELELFTAAVKRWHPSATEWL

FIG.2C

PEYMKGVYMVLYETVNEMAGEAEKSQGRDTLNYGRNALEAYIDASMEEAK
WIFSGFLPTFEEYLDNGKVSFGYGIGTLQPILTLGIPFPHHILQEIDFPSRLNDVA
SSILRLKGDIHTYQAERSRGEKSSCISCYMEENPESTEEDAINHINSMVDKLLK
ELNWEYLRPDSNVPITSKKHAFDILRAFYHLYKYRDGFSVANYEIKNLVMTT
VIEPVPL (SEQ ID NO:28)

P._coulteri_MBO_translation_frame_+1    -----------------------------
RRIAGHHSNLWDDBXIQSLSTPYGAISYHESAQKLIGEVKEMINSISVKDGELI
TPSNDLLMRLSIVDSIERLGIDRHFKSEIKSALDYVYSYWNEKGIGWGRDSVV
ADLNSTALGLRTLRLHGYPVSSDVLQHFKEQKGQFACSAIQTEGEIRSVLNLF
RASQIAFPGEKVMEEAEVFSTIYLKEAILKLPVCGLSREISYVLEYGWHINLPR
LEARNYIDVFGEDPIYLTPNMKTQKLLELAKLEFNMFHSLQQQELKLLSRWW
KDSGFSQMTFPRHRHVEYYTLASCIDSEPQHSSFRLGFAKIFHLATVLDDIYDT
FGTMDELELFTAAVKRWHPSATEWLPEYMKGVYMVLYETVNEMAGEAEKS
QGRDTLNYGRNALEAYIDASMEEAKWIFSGFLPTFEEYLDNGKVSFGYGIGTL
QPILTLGIPFPHHILQEIDFPSRLNDVASSILRLKGDIHTYQAERSRGEKSSCISC
YMEENPESTEEDAINHINSMVDKLLKELNWEYLRPDSNVPITSKKHAFDILRA
FYHLYKYRDGFSVANYEIKNLVMTTVIEPVPL (SEQ ID NO:29)

P._torreyana_MBO_translation_frame_+1    --------------------------------------
NLWDDDLIQSLSTPYGAISYHESAQKLIGEVKEMINSISVKDGELITPSNDLLM
RLSIVDSIERLGIDRHFKSEIKSALDYVYSYWNEKGIGWGRDSVVADLNSTAL
GLRTLRLHGYPVSSDVLQHFKEQKGQFACSAIQTEGEIRSVLNLFRASQIAFPG
EKVMEEAEVFSTMYLKEAILKLPVCGLSREISYVLEYGWHINLPRLEARNYID
VFGQDPIYLTPNMKTQKLLELAKLEFNMFHSLQQQELKLLSRWWKDSGFSQ
MTFPRHRHVEYYTLASCIDSEPQHSSFRLGFAKIFHLATVLDDIYDTFGTMDE
LELFTAAVKRWHPSATEWLPEYMKGVYMVLYETVNEMAGEAEKSQGRDTL
NYARNALEAYIDASMEEAKWIFSGFLPTFEEYLDNGKVSFGYGIGTLQPILTL
GIPFPHHILQEIDFPSRLNDVASSILRLKGDIHTYQAERSRGEKSSCISCYMEEN
PESTEEDAINHINSMVDKLLKELNWEYLRPDSNVPITSKKHAFDILRAFYHLY
KYRDGFSVANYEIKNLVMTTVIEPVPL (SEQ ID NO:30)

P._attenuata_MBO_translation_frame_+1    -----------------------------
RRRGDFHSNLWDDNFIQSLSTPYGAISYHESAQKLIGEVKEMINSISDKDGELI
TPSNDLLMLLSIVDSIERLGIDRHFKSEIKSALDYVYSYWNEKGIGWGRDSVV
ADLNSTALGLRTLRLHGYPVSSDVLQHFKEQNGQFACSAIQTEGEIRSVLNLF
RASQIAFPGEKVMEEAEVFSTKYLKEAILKLPVCGLSREISYVLEYGWIMNLP
RLEARNYIDVFGQDPIYLTPNMKTQKLLELAKLEFNMFHSLQQQELKLLSRW
WKDSGFSQMTFPRHRHVEYYTLASCIDSEPQHSSFRLGFAKIFHLATVLDDIY
DTFGTMDELELFTAAVKRWHPSATEWLPEYMKGVYMVLYETVNEMAGEAE
KSQGRDTLNYARNALEAYIDASMEEAKWIFSGFLPTFEEYLDNGKVSFGYTIG
TLQPILTLGIPFPHHILQEIDFPSRLNDVACSILRLKGDVHTYQPERSRGEESSCI
SCYIEENPESTEEDAINHINSMVDKLLKELNWEYLRPDSNVPITSKKHAFDILR
ALYHLYKYRDGYSVANYEIKNLVMTTVIEPVPL (SEQ ID NO:31)

P._radiata_MBO_translation_frame_+1    --------------------------------------
NLWDDDLIQSLSTPYGAISYHESAQKLIGEVKEMINSISDKNGELITPSNDLLM
RLSIVDSIERLGIDRHFKSEIKSALDYVYSYWNEKGIGWGRDSVVADLNSTAL
GLRTLRLHGYPVSSDVLQHFKEQNGQFACSAIQTEGEIRSVLNLFRASQIAFPG
EKVMEEAEVFSTKYLKEAILKLPVCGLSREISYVLEYGWHMNLPRLEARNYI

FIG. 2D

DVFGQDPIYLTPNMKTQKLLELAKLEFNMFHSLQQQELKLLSRWWKDSGFS
QMTFPRHRHVEYYTLASCIDSEPQHSSFRLGFAKIFHLATVLDDIYDTFGTMD
ELELFTAAVKRWHPSATEWLPEYMKGVYMVLYETVNEMAGEAEKSQGRDT
LNYARNALEAYIDASMEEAKWIFSGFLPTFEEYLDNGKVSFGYTIGTLQPILTL
GIPFPHHILQEIDFPSRLNDVACSILRLKGDVHTYQPERSRGEESSCISCYMEEN
PESTEEDAINHINSMVDKLLKELNWEYLRPDSNVPITSKKHAFDILRALYHLY
KYRDGYSVANYEIKNLVMTTVIEPVPL (SEQ ID NO:32)

P._contorta_MBO1_translation_frame_+1
SSKVKVVRRTMSTSIRMCQITTVSGEGVQRRIANHHSNLWDDNFIQSLSTPYG
AISYHESAQKLIGEVKEMINSISVKDGELITPSNDLLMRLSIVDSIERLGIDRHF
KSEIKSALDYVYSYWNEKGIGWGRDSVVADLNSTALGLRTLRLHGYPVSSDV
LQHFKEQKGQFACSAIQTEGEIRSVLNLFRASQIAFPGEKVMEEAEVFSTKYL
KEAILKLPVCGLSREISYVLEYGWHMNLPRLEARNYIDVFGQDPIYLTPNMKT
QKLLELAKLEFNMFHSLQQQELKLLSRWWKDSGFSQMTFPRHRHVEYYTLA
SCIDSEPQHSSFRLGFAKIFHLATVLDDIYDTFGTMDELELFTAAVKRWHPSAT
EWLPEYMKGVYMVLYETVNEMAGEAEKSQGRDTLNYARNALEAYIDASME
EAKWIFSGFLPTFEEYLDNGKVSFGYTIGTLQPILTLGIPFPHHILQEIDFPSRLN
DVACSILRLKGDHITYQPERSRGEESSCISCYMEDNPESTEEDAINIINSMVDK
LLKELNWEYLRPDSNVPITSKKHAFDILRAFYHLYKYRDGYSVANYEIKNLV
MTTVIEPVPL (SEQ ID NO:33)

P._contorta_MBO2_translation_frame_+1
SSKVKVVRRTMSTSIRMCQITTVSGEGVQRRIANHHSNLWDDNFIQSLSTPYG
AISYHESAQKLIGEVKEMINSISVKDGELITPSNDLLMRLSIVDSIERLGIDRHF
KSEIKSALDYVYSYWNEKGIGWGRDSVVADLNSTALGLRTLRLHGYPVSSDV
LQHFKEQKGQFACSAIQTEGEIRSVLNLFRASQIAFPGEKVMEEAEVFSTKYL
KEAILKLPVCGLSREISYVLEYGWHINLPRLEARNYIDVFGQDPIYLTPNMKTQ
KLLELAKLEFNMFHSLQQQELKLLSRWWKDSGFSQMTFPRHRHVEYYTLAS
CIDSEPQHSSFRLGFAKIFHLATVLDDIYDTFGTMDELELFTAAVKRWHPSAT
EWLPEYMKGVYMVLYETVNEMAGEAEKSQGRDTLNYARNALEAYIDASME
EAKWIFSGFLPTFEEYLDNGKVSFGYTIGTLQPILTLGIPFPHHILQEIDFPSRLN
DVACSILRLKGDVHTYQAERSRGEESSCISCYMEDNPESTEEDAINHINSMVD
KLLKELNWEYLRPDSNVPITSKKHAFDILRAFYHLYKYRDGYSVANYEIKNL
VMTTVIEPVPL (SEQ ID NO:34)

FIG.2E

SEQUENCE LISTING

```
<160> NUMBER OF SEQ ID NOS: 34

<210> SEQ ID NO 1
<211> LENGTH: 1782
<212> TYPE: DNA
<213> ORGANISM: P. pseudostrobus estevezii

<400> SEQUENCE: 1
tctagcaagg ttaaggttgt ccgcagaacg atctcaactt ccatccgcat gtgtcggata      60
accactgtat ccggtgaagg cgtacagaga cgcatagcaa atcatcattc caacctctgg     120
gacgataatt tcatacagtc cctctcaacc ccttatgggg caatttcgta ccatgaaagt     180
gctcagaaac ttattggaga agtaaaagag ataatcaatt caatctcggt taaagatgga     240
gaattaatca cccccctccaa tgatctcctt atgcggctct ctatagtcga tagcattgaa     300
cgtttgggaa ttgataggca tttcaaaagt gaaataaaat cagctctgga ttacgtttac     360
agttattgga acgaaaaagg cattgggtgg ggaagagata gtgttgttgc cgatctcaac     420
tcaactgcct tggggcttcg aactctacga ctacacggat acccggtgtc ttcagatgtg     480
ttacaacact tcaaagaaca aaaagggcag tttgcatgtt cggccattca aacagaggga     540
gagataagaa gtgttctcaa cttatttcgg gcttcccaaa ttgcctttcc gggagagaaa     600
gttatggaag aggcagaagt cttctctaca atatatttaa aagaagccat actaaagctt     660
ccggtctgcg gtctttcacg agagatatcg tacgttctgg aatatggttg gcatataaat     720
ttgccaagat tggaagcaag gaactacatc gacgtatttg gacaggaccc catttatttg     780
acgccaaata tgaagaccca aaaacttcta gaacttgcaa agttggagtt caatatgttt     840
cactctttac aacagcaaga gctaaagctt ctctccagat ggtggaaaga ttcgggtttc     900
tctcaaatga ccttccctcg gcatcgtcac gtggaatatt acactttggc atcttgcatt     960
gatagtgaac ctcaacattc ttcgttcaga cttggatttg ccaaaatctt tcatcttgcc    1020
acggttcttg acgatattta cgacaccttt ggcacgatgg atgagctaga actcttcacg    1080
gcggcagtta agaggtggca tccgtctgcg acggagtggc ttccagaata tatgaaagga    1140
gtatatatgg tgctttacga aaccgttaac gaaatggcag gagaagcaga aaagtctcaa    1200
ggccgagaca cgctcaacta tgcccgaaat gctttggagg cttatattga tgcttctatg    1260
aaagaagcga agtggatttt cagtggtttt ttgccaacat ttgaggagta cctggataac    1320
gggaaagtta gtttcggtta tagcattggc acattgcaac ccattctgac gttgggcatt    1380
ccctttcctc atcacatcct acaagaaata gactttcctt ccaggctcaa tgatgtggca    1440
tgttccattc tccgactaaa aggcgacatt cacacttacc aggctgagag gagccgtgga    1500
gaaaaatctt cgtgtatatc atgttatatg gaagagaatc ccgagtcaac agaggaagat    1560
gcaatcaatc atgtcaactc catggtcgac aaattactca aggaactaaa ttgggagtat    1620
ctgagacctg atagcaatgt tccaatcact tccaagaaac atgcatttga cattctgaga    1680
gctttctacc atctctacaa ataccgagat ggcttcagcg ttgcgaacta tgaaataaag    1740
aatttggtca tgacaaccgt cattgagcct gtgcctttat aa                        1782
```

<210> SEQ ID NO 2
<211> LENGTH: 1782
<212> TYPE: DNA
<213> ORGANISM: P cooperi ornelasi

<400> SEQUENCE: 2

| | | | | | | |
|---|---|---|---|---|---|---|
| tctagcaagg | ttaaggttgt | ccgcagaacg | atctcaactt | ccatccgcat | gtgtcggata | 60 |
| accactgtat | ccggtgaagg | cgtacagaga | cgcatagcaa | atcatcattc | caacctctgg | 120 |
| gacgataatt | tcatacagtc | cctctcaacg | ccttatgggg | caatttcgta | ccatgaaagt | 180 |
| gctcagaaac | ttattggaga | agtaaaagag | atgatcaatt | caatctcggt | taaagatgga | 240 |
| gaattaatca | ccccctccaa | tgatctcctt | atgcggctct | ctatagtcga | tagcattgaa | 300 |
| cgtttgggaa | tcgataggca | tttcaaaagt | gaaataaaat | cagctctgga | ttatgtttac | 360 |
| agttattgga | acgaaaaagg | cattgggtgg | ggaagagata | gtgttgttgc | cgatctcaac | 420 |
| tcaactgcct | ggggcttcg | aactctacga | ctacacggat | acccggtgtc | ttcagatgtg | 480 |
| ttacaacact | tcaaagaaca | aaagggcag | tttgcatgtt | cggccattca | aacagaggga | 540 |
| gagataagaa | gtgttctcaa | cttatttcgg | gcttcccaaa | ttgcctttcc | gggagagaaa | 600 |
| gttatggaag | aggcagaagt | cttctctaca | atatatttaa | agaagccat | actaaagctt | 660 |
| ccggtctgcg | gtctttcacg | agagatatcg | tacgttctgg | aatatggttg | gcatataaat | 720 |
| ttgccaagat | tggaagcaag | gaactacatc | gacgtatttg | gacaggaccc | catttatttg | 780 |
| acgccaaata | tgaagaccca | aaaacttcta | gaacttgcaa | agttggagtt | caatatgttt | 840 |
| cactctttac | aacagcaaga | gctaaagctt | ctctccagat | ggtggaaaga | ttcgggtttc | 900 |
| tctcaaatga | ccttccctcg | gcatcgtcac | gtggaatatt | acactttggc | atcttgcatt | 960 |
| gatagtgaac | ctcaacattc | ttcgttcaga | cttggatttg | ccaaaatctt | tcatcttgcc | 1020 |
| acggttcttg | acgatattta | cgacaccttt | ggcacgatgg | atgagctaga | actcttcacg | 1080 |
| gcggcagtta | agaggtggca | tccgtctgcg | acggagtggc | ttccagaata | tatgaaagga | 1140 |
| gtatatatgg | tgctttacga | aaccgttaac | gaaatggcag | gagaagcaga | aaagtctcaa | 1200 |
| ggccgagaca | cgctcaacta | tgcccgaaat | gctttggagg | cttatattga | tgcttctatg | 1260 |
| aaagaagcga | agtggatttt | cagtggtttt | ttgccaacat | ttgaggagta | cctggataac | 1320 |
| gggaaagtta | gtttcggtta | tagcattggc | acattgcaac | ccattctgac | gttgggcatt | 1380 |
| ccctttcctc | atcacatcct | acaagaaata | gactttcctt | ccaggctcaa | tgatgtggca | 1440 |
| tgttccattc | tccgactaaa | aggcgacatt | cacacttacc | aggctgagag | gagccgtgga | 1500 |
| gaaaaatctt | cgtgtatatc | atgttatatg | gaagagaatc | ccgagtcaac | agaggaagat | 1560 |
| gcaatcaatc | atatcaactc | catggtcgac | aaattactca | aggaactaaa | ttgggagtat | 1620 |
| ctgagacctg | atagcaatgt | tccaatcact | tccaagaaac | atgcatttga | cattctgaca | 1680 |
| gctttctacc | atctctacaa | ataccgagat | ggcttcagcg | ttgcgaacta | tgaaataaag | 1740 |
| aatttggtca | tgacaaccgt | cattgagcct | gtgcctttat | aa | | 1782 |

<210> SEQ ID NO 3
<211> LENGTH: 1782
<212> TYPE: DNA
<213> ORGANISM: P. hartwegii

<400> SEQUENCE: 3

| | | | | | | |
|---|---|---|---|---|---|---|
| tctagcaagg | ttaaggttgt | ccgcagaacg | atctcaactt | ccatccgcat | gtgtcggata | 60 |

```
accactgtat ccggtgaagg cgtacagaga cgcatagcaa atcatcattc caacctctgg    120
gacgataatt tcatacagtc cctctcaacg ccttatgggg caatttcgta ccatgaaagt    180
gctcagaaac ttattggaga agtaaaagag atgatcaatt caatctcggt taaagatgga    240
gaattaatca ccccctccaa tgatctcctt atgcggctct ctatagtcga tagcattgaa    300
cgtttgggaa tcgataggca tttcaaaagt gaaataaaat cagctctgga ttatgtttac    360
agttattgga acgaaaaagg cattgggtgg ggaagagata gtgttgttgc cgatctcaac    420
tcaactgcct tggggcttcg aactctacga ctacacggat acccggtgtc ttcagatgtg    480
ttacaacact tcaaagaaca aaaagggcag tttgcatgtt cggccattca aacagaggga    540
gagataagaa gtgttctcaa cttatttcgg gcttcccaaa ttgcctttcc gggagagaaa    600
gttatggaag aggcagaagt cttctctaca atatatttaa aagaagccat actaaagctt    660
ccggtctgcg gtctttcacg agagatatcg tacgttctgg aatatggttg gcatataaat    720
ttgccaagat tggaagcaag gaactacatc gacgtatttg gacaggaccc catttatttg    780
acgccaaata tgaagaccca aaaacttcta gaacttgcaa agttggagtt caatatgttt    840
cactctttac aacagcaaga gctaaagctt ctctccagat ggtggaaaga ttcgggtttc    900
tctcaaatga ccttccctcg gcatcgtcac gtggaatatt acactttggc atcttgcatt    960
gatagtgaac ctcaatattc ttcgttcaga cttggatttg ccaaaatctt tcatcttgcc   1020
acggttcttg acgatattta cgacacctt ggcacgatgg atgagctaga actcttcacg   1080
gcggcagtta agaggtggca tccgtctgcg acggagtggc ttccagaata tatgaaagga   1140
gtatatatgg tgctttacga aaccgttaac gaaatggcag agaagcaga aaagtctcaa    1200
ggccgagaca cgctcaacta tgcccgaaat gctttggagg cttatattga tgcttctatg   1260
aaagaagcga agtggatttt cagtggtttt ttgccaacat tgaggagta cctggataac   1320
gggaaagtta gtttcggtta tagcattggc acattgcaac ccattctgac gttgggcatt   1380
ccctttcctc atcacatcct acaagaaata gactttcctt ccaggctcaa tgatgtggca   1440
tgttccattc tccgactaaa aggcgacatt cacacttacc aggctgagag gagccgtgga   1500
gaaaaatctt cgtgtatatc atgttatatg gaagagaatc ccgagtcaac agaggaagat   1560
gcaatcaatc atatcaactc catggtcgac aaattactca aggaactaaa ttgggagtat   1620
ctgagacctg atagcaatgt tccaatcact tccaagaaac atgcatttga cattctgaga   1680
gctttctacc atctctacaa ataccgagat ggcttcagcg ttgcgaacta tgaaataaag   1740
aatttggtca tgacaaccgt cattgagcct gtgccttat aa                       1782
```

<210> SEQ ID NO 4
<211> LENGTH: 1782
<212> TYPE: DNA
<213> ORGANISM: P. ponderosa

<400> SEQUENCE: 4

```
tctagcaagg ttaaggttgt ccgcagaacg atctcaactt ccatccgcat gtgtcggata     60
accactgaat ccggtgaagg cgtacagaga cgcatagcaa atcatcattc caacctctgg    120
gacgataatt tcatacagtc cctctcaacg ccttatgggg caatttcgta ccatgaaagt    180
gctcagaaac ttattggaga agtaaaagag atgatcaatt caatctcgct taaagatgga    240
gaattaatca ccccctccaa tgatctcctt atgcggctct ctagttga tagcattgaa    300
cgtttgggaa tcgataggca tttcaaaagt gaaataaaat cagctctgga ttatgtttac    360
agttattgga acgaaaaagg cattgggtgg ggaagagata gtgttgttgc cgatctcaac    420
```

```
tcaactgcct tggggcttcg aactctacga ctacacggat acccggtgtc ttcagatgtg      480
ttacaacact tcaaagaaca aaaagggcag tttgcatgtt cggccattca aacagaggga      540
gagataagaa gtgttctcaa cttatttcgg gcttcccaaa ttgcctttcc gggagagaaa      600
gttatggaag aggcagaagt cttctctaca atatatttaa aagaagccat actaaagctt      660
ccggtctgcg gtctttcacg agagatatcg tacgttctgg aatatggttg gcatataaat      720
ttgccaagat tggaagcaag gaactacatc gacgtatttg gacaggaccc catttatttg      780
acgccaaata tgaagaccca aaaacttcta gaacttgcaa agttggagtt caatatgttt      840
cactctttac aacagcaaga gctaaagctt ctctccagat ggtggaaaga ttcgggtttc      900
tctcaaatga ccttccctcg gcatcgtcac gtggaatatt acactttggc atcttgcatt      960
gatagtgaac ctcaacattc ttcgttcaga cttggatttg ccaaaatctt tcatcttgcc     1020
acggttcttg acgatattta cgacaccttt ggcacgatgg atgagctaga actcttcacg     1080
gcggcagtta agaggtggca tccgtctgcg acggagtggc ttccagaata tatgaaagga     1140
gtatatatgg tgctttacga aaccgttaac gaaatggcga gagaagcaga aaagtctcaa     1200
ggccgagaca cgctcaacta tgcccgaaat gctttggagg cttatattga tgcttctatg     1260
aaagaagcga agtggatttt cagtggtttt ttgccaacat ttgaggagta cctggataac     1320
gggaaagtta gtttccggtta tagcattggc acattgcaac ccattctgac gttgggcatt     1380 cccttttcctc atcacatcct acaagaaata gactttcctt ccaggctcaa tgatgtggca     1440
tgttccattc tccgactaaa aggcgacatt cacacttacc aggctgagag agccgtggaa     1500
gaaaaatctt cgtgtatatc atgttatatg gaagagaatc ccgagtcaac agaggaagat     1560
gcaatcaatc atatcaactc catggtcgac aaattactca aggaactaaa ttgggagtat     1620
ctgagacctg atagcaatgt tccaatcact tccaagaaac atgcatttga cattctgaga     1680
actttctacc atctctacaa ataccgagat ggcttcagcg ttgcgaacta tgaaataaag     1740
aatttggtca tgacaaccgt cattgagcct gtgcctttat aa                        1782
```

<210> SEQ ID NO 5
<211> LENGTH: 1782
<212> TYPE: DNA
<213> ORGANISM: P. ponderosa

<400> SEQUENCE: 5

```
tctagcaagg ttaaggttgt ccgcagaacg atctcaactt ccatccgcat gtgtcggata       60
accactgaat ccggtgaagg cgtacagaga cgcatagcaa atcatcattc caacctctgg      120
gacgataatt tcatacagtc cctctcaacg ccttatgggg caatttcgta ccatgaaagt      180
gctcagaaac ttattggaga agtaaaagag atgatcaatt caatctcgct taaagatgga      240
gaattaatca ccccctccaa tgatctcctt atgcggctct ctatagttga tagcattgaa      300
cgtttgggaa tcgataggca tttcaaaagt gaaataaaat cagctctgga ttatgtttac      360
agttattgga acgaaaaagg cattgggtgg ggaagagata gtgttgttgc cgatctcaac      420
tcaactgcct tggggcttcg aactctacga ctacacggat acccggtgtc ttcagatgtg      480
ttacaacact tcaaagaaca aaaagggcag tttgcatgtt cggccattca aacagaggga      540
gagataagaa gtgttctcaa cttatttcgg gcttcccaaa ttgcctttcc gggagagaaa      600
gttatggaag aggcagaagt cttctctaca atatatttaa aagaagccat actaaagctt      660
ccggtctgcg gtctttcacg agagatatcg tacgttctgg aatatggttg gcatataaat      720
```

```
ttgccaagat tggaagcaag gaactacatc gacgtatttg gacaggaccc catttatttg    780
acgccaaata tgaagaccca aaaattctca gaacttgcaa agttggagtt caatatgttt    840
cactctttac aacagcaaga gctaaagctt ctctccagat ggtggaaaga ttcgggtttc    900
tctcaaatga ccttccctcg gcatcgtcac gtggaatatt acactttggc atcttgcatt    960
gatagtgaac ctcaacattc ttcgttcaga cttggatttg ccaaaatctt tcatcttgcc   1020
acggttcttg acgatattta cgacaccttt ggcacgatgg atgagctaga actcttcacg   1080
gcggcagtta agaggtggca tccgtctgcg acggagtggc ttccagaata tatgaaagga   1140
gtatatatgg tgctttacga aaccgttaac gaaatggcga gagaagcaga aaagtctcaa   1200
ggccgagaca cgctcaacta tgcccgaaat gctttggagg cttatattga tgcttctatg   1260
aaagaagcga agtggatttt cagtggtttt ttgccaacat tgaggagta  cctgtataac   1320
gggaaagtta gtttcggtta tagcattggc acattgcaac ccattctgac gttgggcatt   1380
cccttttcctc atcacatcct acaagaaata gactttcctt ccaggctcaa tgatgtggca   1440
tgttccattc tccgactaaa aggcgacatt cacacttacc aggctgagag gagccgtgga   1500
gaaaaatctt cgtgtatatc atgttatatg gaagagaatc ccgagtcaac agaggaagat   1560
gcaatcaatc atatcaactc catggtcgac aaattactca aggaactaaa ttgggagtat   1620
ctgagacctg atagcaatgt tccaatcact tccaagaaac atgcatttga cattctgaga   1680
actttctacc atctctacaa ataccgagat ggcttcagcg ttgcgaacta tgaaataaag   1740
aatttggtca tgacaaccgt cattgagcct gtgcctttat aa                      1782

<210> SEQ ID NO 6
<211> LENGTH: 1782
<212> TYPE: DNA
<213> ORGANISM: P. jeffreyi

<400> SEQUENCE: 6
tctagcaagg ttaaggttgt ccgcagaacg atctcaactt ccatccgcat gtgtcggata     60
accactgaat ccggtgaagg cgtacagaga cgcatagcaa atcatcattc caacctctgg    120
gacgataatt tcatacagtc cctctcaacg ccttatgggg caatttcgta ccatgaaagt    180
gctcagaaac ttattggaga agtaaaagag atgatcaatt caatctcgct taaagatgga    240
gaattaatca ccccctccaa tgatctcctt atgcggctct ctatagttga tagcattgaa    300
cgtttgggaa tcgataggca tttcaaaagt gaaataaaat cagctctgga ttatgtttac    360
agttattgga acgaaaaagg cattgggtgg ggaagagata gtgttgttgc cgatctcaac    420
tcaactgcct tggggcttcg aactctacga ctacacggat acccggtgtc ttcagatgtg    480
ttacaacact tcaaagaaca aaaagggcag tttgcatgtt cggccattca aacagaggga    540
gagataagaa gtgttctcaa cttatttcgg gcttcccaaa ttgcctttcc gggagagaaa    600
gttatggaag aggcagaagt cttctctaca atatatttaa aagaagccat actaaagctt    660
ccggtctgcg gtctttcacg agagatatcg tacgttctgg aatatggttg gcatataaat    720
ttgccaagat tggaagcaag gaactacatc gacgtatttg gacaggaccc catttatttg    780
acgccaaata tgaagaccca aaaacttcta gaacttgcaa agttggagtt caatatgttt    840
cactctttac aacagcaaga gctaaagctt ctctccagat ggtggaaaga ttcgggtttc    900
tctcaaatga ccttccctcg gcatcgtcac gtggaatatt acactttggc atcttgcatt    960
gatagtgaac ctcaacattc ttcgttcaga cttggatttg ccaaaatctt tcatcttgcc   1020
acggttcttg acgatattta cgacaccttt ggcacgatgg atgagctaga actcttcacg   1080
```

```
gcggcagtta agaggtggca tccgtctgcg acggagtggc ttccagaata tatgaaagga    1140
gtatatatgg tgctttacga aaccgttaac gaaatggcag gagaagcaga aaagtctcaa    1200
ggccgagaca cgctcaacta tgcccgaaat gcttcggagg cttatattga tgcttctatg    1260
aaagaagcga agtggatttt cagtggtttt ttgccaacat ttgaggagta cctggataac    1320
gggaaagtta gtttcggtta tagcattggc acattgcaac ccattctgac gttgggcatt    1380 cccttcctc atcacatcct acaagaaata gactttcctt ccaggctcaa tgatgtggca    1440
tgttccattc tccgactaaa aggcgacatt cacacttacc aggctgagag gagccgtgga    1500
gaaaaatctt cgtgtatatc atgttatatg aagagaatc ccgagtcaac agaggaagat    1560
gcaatcaatc atatcaactc catggtcgac aaattactca aggaactaaa ttgggagtat    1620
ctgagacctg atagcaatgt tccaatcact tccaagaaac atgcatttga cattctgaga    1680
gctttctacc atctctacaa ataccgagat ggcttcagcg ttgcgaacta tgaaataaag    1740
aatttggtca tgacaaccgt cattgagcct gtgcctttat aa                      1782
```

```
<210> SEQ ID NO 7
<211> LENGTH: 1771
<212> TYPE: DNA
<213> ORGANISM: P. sabiniana

<400> SEQUENCE: 7
```

```
tctagcaagg ttaaggttgt ccgcagaacg atctcaactt ccatccgcat gtgtcggata     60
accactgaat ccggtgaagg cgtacagaga cgcatagcaa atcatcattc caacctctgg    120
gacgataatt tcatacagtc cctctcaacg ccttatgggg caatttcgta ccatgaaagt    180
gctcagaaac ttattggaga agtaaaagag atgatcaatt caatctcggt taaagatgga    240
gaattaatca ccccctccaa tgatctcctt atgcggctct ctatagttga tagcattgaa    300
cgtttaggaa tcgataggca tttcaaaagt gaaataaaat cagctctgga ttatgtttac    360
agttattgga acgaaaaagg cattgggtgg ggaagagata gtgttgttgc cgatctcaac    420
tcaactgcct tgggcttcg aactctacga ctacacggat acccggtgtc ttcagatgtg    480
ttacaacact tcaaagaaca aaaagggcag tttgcatgtt cggccattca aacagaggga    540
gagataagaa gtgttctcaa cttatttcgg gcttcccaaa ttgcctttcc gggagagaaa    600
gttatggaag aggcagaagt cttctctaca atatatttaa aagaagccat actaaagctt    660
ccggtctgcg gtctttcacg agagatatcg tacgttctgg aatatggttg gcatataaat    720
ttgccaagat tggaagcaag gaactacatc gacgtatttg gagaggaccc catttatttg    780
acgccaaata tgaagaccca aaaacttcta gaacttgcaa agttggagtt caatatgttt    840
cactctttac aacagcaaga gctaaagctt ctctccagat ggtggaaaga ttcgggtttc    900
tctcaaatga ccttccctcg gcatcgtcac gtggaatatt acactttggc atcttgcatt    960
gatagtgaac ctcaacattc ttcgttcaga cttggatttg ccaaaatctt tcatcttgcc   1020
acggttcttg acgatattta cgacacctttt ggcacgatgg atgagctaga actcttcacg   1080
gcggcagtta agaggtggca tccgtctgcg acggagtggc ttccagaata tatgaaagga   1140
gtatatatgg tgctttacga aaccgttaac gaaatggcag gagaagcaga aaagtctcaa   1200
ggccgagaca cgctcaacta tggccgaaat gctttggagg cttatattga tgcttctatg   1260
gaagaagcga agtggatttt cagtggtttt ttgccaacat ttgaggagta cctggataac   1320
gggaaagtta gtttcggtta taggcattggc acattgcaac ccattctgac gttgggcatt   1380
```

| cccttttcctc atcacatcct acaagaaata gactttcctt ccaggctcaa tgatgtggca | 1440 |
| tcttccattc tccgactaaa aggcgacatt cacacttacc aggctgagag gagccgtgga | 1500 |
| gaaaaatctt cgtgtatatc atgttatatg aagagaatc ccgagtcaac agaggaagat | 1560 |
| gcaatcaatc atatcaactc catggtcgac aaattactca aggaactaaa ttgggagtat | 1620 |
| ctgagacctg atagcaatgt tccaatcact tccaagaaac atgcatttga cattctgaga | 1680 |
| gctttctacc atctctacaa ataccgagat ggcttcagcg ttgcgaacta tgaaataaag | 1740 |
| aatttggtca tgacaaccgt cattgagcct g | 1771 |

<210> SEQ ID NO 8
<211> LENGTH: 1783
<212> TYPE: DNA
<213> ORGANISM: P. sabiniana

<400> SEQUENCE: 8

| tctagcaagg ttaaggttgt ccgcagaacg atctcaactt ccatccgcat gtgtcggata | 60 |
| accactgaat ccggtgaagg cgtacagaga cgcatagcaa atcatcattc caacctctgg | 120 |
| gacgataatt tcatacagtc cctctcaacg ccttatgggg caatttcgta ccatgaaagt | 180 |
| gctcagaaac ttattggaga agtaaaagag atgatcaatt caatctcgct taaagatgga | 240 |
| gaattaatca cccctccaa tgatctcctt atgcggctct ctatagtcga tagcattgaa | 300 |
| cgtttgggaa tcgataggca tttcaaaagt gaaataaaat cagctctgga ttatgtttac | 360 |
| agttattgga acgaaaaagg cattgggtgg ggaagagata tgttgttgc cgatctcaac | 420 |
| tcaactgcct tggggcttcg aactctacga ctacacggta acccggtgtc ttcagatgtg | 480 |
| ttacaacact tcaaagaaca aaagggcag tttgcatgtt cggccattca acagaggga | 540 |
| gagataagaa gtgttctcaa cttatttcgg gcttcccaaa ttgccttcc gggagagaaa | 600 |
| gttatggaag aggcagaagt cttctctaca atatatttaa agaagccat actaaagctt | 660 |
| ccggtctgcg gtctttcacg agagatatcg tacgttctgg aatatggttg gcatataaat | 720 |
| ttgccaagat tggaagcaag gaactacatc gacgtatttg gagaggaccc catttatttg | 780 |
| acgccaaata tgaagaccca aaaacttcta gaacttgcaa agttggagtt caatatgttt | 840 |
| cactctttac aacagcaaga gctaaagctt ctctccagat ggtggaaaga ttcgggtttc | 900 |
| tctcaaatga ccttccctcg gcatcgtcac gtggaatatt acactttggc atcttgcatt | 960 |
| gatagtgaac ctcaacattc ttcgttcaga cttggatttg ccaaaatctt tcatcttgcc | 1020 |
| acggttcttg acgatattta cgacacctttt ggcacgatgg atgagctaga actcttcacg | 1080 |
| gcggcagtta agaggtggca tccgtctgcg acggagtggc ttccagaata tatgaaagga | 1140 |
| gtatatatgg tgctttacga aaccgttaac gaaatggcag agaagcaga aagtctcaa | 1200 |
| ggccgagaca cgctcaacta tggccgaaat gctttggagg cttatattga tgcttctatg | 1260 |
| gaagaagcga agtggatttt cagtggtttt ttgccaacat tgaggagta cctggataac | 1320 |
| gggaaagtta gtttcggtta tggcattggc acattgcaac ccattctgac gttgggcatt | 1380 |
| cccttttcctc atcacatcct acaagaaata gactttcctt ccaggctcaa tgatgtggca | 1440 |
| tcttccattc tccgactaaa aggcgacatt cacacttacc aggctgagag gagccgtgga | 1500 |
| gaaaaatctt cgtgtatatc atgttatatg aagagaatc ccgagtcaac agaggaagat | 1560 |
| gcaatcaatc atatcaactc catggtcgac aaattactca aggaactaaa ttgggagtat | 1620 |
| ctgagacctg atagcaatgt tccaatcact tccaagaaac atgcatttga cattctgaga | 1680 |
| gctttctacc atctctacaa ataccgagat ggcttcagcg ttgcgaacta tgaaataaag | 1740 | aatttggtca tgacaaccgt cattgagcct gtgcctttat aaa                         1783

<210> SEQ ID NO 9
<211> LENGTH: 1782
<212> TYPE: DNA
<213> ORGANISM: P. patula

<400> SEQUENCE: 9
tctagcaagg ttaaggttgt ccgcagaacg atctcaactt ccatccgcat gtgtcggata         60
actactgtat ccggtgaagg cgtacagaga cgcatagcaa atcatcattc caacctctgg        120
gacgataatt tcatacagtc cctctcaacg ccttatgggg caatttcgta ccatgaaagt        180
gctcagaaac ttattggaga agtaaaagag atgatcaatt caatctcggt taaagatgga        240
gaattaatca cccctccaa tgatctcctt atgcggctct ctatagtcga tagcattgaa         300
cgtttgggaa tcgataggca tttcaaaagt gaaataaaat cagctctgga ttatgtttac        360
agttattgga acgaaaaagg cattgggtgg ggaagagata gtgttgttgc cgatctcaac        420
tcaactgcct tggggcttcg aactctacga ctacacggat acccggtgtc ttcagatgtg        480
ttacaacact tcaaagaaca aaaagggcag tttgcatgtt cggccattca aacagaggga        540
gagataagaa gtgttctcaa cttatttcgg gcttcccaaa ttgcctttcc gggagagaaa        600
gttatggaag aggcagaagt cttctctaca atatatttaa aagaagccat actaaagctt        660
ccggtctgcg gtcttcacg agagatatcg tacgttctgg aatatggttg gcatataaat         720
ttgccaagat tggaagcaag gaactacatc gacgtatttg gacaggaccc catttatttg        780
acgccaaata tgaagaccca aaaacttcta gaacttgcaa agttggagtt caatatgttt        840
cactctttac aacagcaaga gctaaagctt ctctccagat ggtggaaaga ttcgggtttc        900
tctcaaatga ccttccctcg gcatcgtcac gtggaatatt acactttggc atcttgcatt        960
gatagtgaac ctcaacattc ttcgttcaga cttggatttg ccaaaatatt tcatcttgcc       1020
acggttcttg acgatattta cgacaccttt ggcacgatgg atgagctaga actcttcaca       1080
gcggcagttg agaggtggca tccgtctgcg acggagtggc ttccagaata tatgaaagga       1140
gtatatatgg tgctttacga aaccgttaac gaaatggcag gagaagcaga aaagtctcaa       1200
ggccgagaca cgctcaacta tgcccgaaat gctttggagg cttatattga tgcttctatg       1260
aaagaagcga agtggatttt cagtggtttt ttgccaacat tgaggagta cctggataac        1320 gggaaagtta gtttcggtta tagcattggc acattgcaac ccattctgac gttgggcatt       1380
ccctttcctc atcacatcct acaagaaata gactttcctt ccaggctcaa tgatgtggca       1440
tgttccattc tccgactaaa aggcgacatt cacacttacc aggctgagag gagccgtgga       1500
gaaaaatctt cgtgtatatc atgttatatg gaagagaatc ccgagtcaac agaggaagat       1560
gcaatcgatc atatcaactc catggtcgac aaattactca aggaactaaa tcgggagtat       1620
ctgagacctg atagcaatgt tccaatcact tccaagaaac atgcatttga cattctgaga       1680
gctttctacc atctctacaa ataccgagat ggcttcagcg ttgcgaacta tgaaataaag       1740
aatttggtca tgacaaccgt cattgagcct gtgcctttat aa                          1782

<210> SEQ ID NO 10
<211> LENGTH: 1782
<212> TYPE: DNA
<213> ORGANISM: P. montezumae

<400> SEQUENCE: 10

```
tctagcaagg ttaaggttgt ccgcagaacg atctcaactt ccatccgcat gtgtcggata      60
accactgtat ccggtgaagg cgtacagaga cgcatagcaa atcatcattc caacctctgg     120
gacgataatt tcatacagtc cctctcaacg ccttatgggg caatttcgta ccatgaaagt     180
gctcagaaac ttattggaga agtaaaagag atgatcaatt caatctcggt taaagatgga     240
gaattaatca ccccctccaa tgatctcctt atgcggctct ctatagtcga tagcattgaa     300
cgtttgggaa tcgataggca tttcaaaagt gaaataaaat cagctctgga ttatgtttac     360
agttattgga acgaaaaagg cattgggtgg ggaagagata gtgttgttgc cgatctcaac     420
tcaactgcct tggggcttcg aactctacga ctacacggat acccggtgtc ttcagatgtg     480
ttacagcact tcaaagaaca aaaagggcag tttgcatgtt cggccattca aacagaggga     540
gagataagaa gtgttctcaa cttatttcgg gcttcccaaa ttgccttttcc gggagagaaa    600 gttatggaag aggcagaagt cttctctaca atatatttaa aagaagccat actaaagctt     660
ccggtctgcg gtctttcacg agagatatcg tacgttctgg aatatggttg gcatataaat     720
ttgccaagat tggaagcaag gaactacatc gacgtatttg gacaggaccc catttatttg     780
acgccaaata tgaagaccca aaaacttcta gaacttgcaa agttggagtt caatatgttt     840
cactctttac aacagcaaga gctaaagctt ctctccagat ggtggaaaga ttcgggtttc     900
tctcaaatga ccttccctcg gcatcgtcac gtggaatatt cactttggc atcttgcatt      960 gatagtgaac ctcaacattc ttcgttcaga cttggatttg ccaaaatgtt tcatcttgcc    1020
acggttcttg acgatattta cgacaccttt ggcacgatgg atgagctaga actcttcacg    1080
gcggcagtta agaggtggca tccgtctgcg acggagtggc ttccagaata tatgaaagga    1140
gtatatatgg tgctttacga aaccgttaac gaaatggcag gagaagcaga aaagtctcaa    1200
ggccgagaca cgctcaacta tgcccgaaat gctttggagg cttatattga tgcttctatg    1260
aaagaagcga agtggatttt cagtggtttt ttgccaacat ttgaggagta cctggataac    1320
gggaaagtta gtttcggtta tagcattggc acattgcaac ccattctgac gttgggcatt    1380 cccttttcctc atcacatcct acaagaaata gactttcctt ccaggctcaa tgatgtggca    1440
tgttccattc tccgactaaa aggcgacatt cacacttacg aggctgagag gagccgtgga    1500
gaaaaatctt cgtgtatatc atgttatatg gaagagaatc ccgagtcaac agaggaagat    1560
gcaatcaatc atatcaactc catggtcgac aaattactca aggaactaaa ttgggagtat    1620
ctgagacctg atagcaatgt tccaatcact tccaagaaac atgcatttga cattctgaga    1680
gctttctacc atctctacaa ataccgagat ggcttcagcg ttgcgaacta tgaaataaag    1740
aatttggtca tgacaaccgt cattgagcct gtgcctttat aa                       1782
```

<210> SEQ ID NO 11
<211> LENGTH: 1695
<212> TYPE: DNA
<213> ORGANISM: P. pseudostrobus

<400> SEQUENCE: 11

```
agacgcakag stgrtywyca ttccaaccty tgggacgata atttcataca gtccctctca      60
acgccttatg gggcaatttc gtaccatgaa agtgctcaga acttattgg agaagtaaaa      120 gagatgatca attcaatctc ggttaaagat ggagaattaa tcaccccctc caatgatctc    180
cttatgcggc tctctatagt cgatagcatt gaacgtttgg gaatcgatag gcatttcaaa    240
agtgaaataa aatcagctct ggattatgtt tacagttatt ggaacgaaaa aggcattggg    300
tggggaagag atagtgttgt tgccgatctc aactcaactg ccttggggct tcgaactcta    360
```

```
cgactacacg gataccoggt gtcttcagat gtgttacagc acttcaaaga acaaaaaggg      420
cagtttgcat gttcggccat tcaaacagag ggagagataa gaagtgttct caacttattt      480
cgggcttccc aaattgcctt tccgggagag aaagttatgg aagaggcaga agtcttctct      540
acaatatatt taaaagaagc catactaaag cttccggtct gcggtctttc acgagagata      600
tcgtacgttc tggaatatgg ttggcatata aatttgccaa gattggaagc aaggaactac      660
atcgacgtat ttggacagga ccccatttat ttgacgccaa atatgaagac ccaaaaactt      720
ctagaacttg caaagttgga gttcaatatg tttcactctt tacaacagca agagctaaag      780
cttctctcca gatggtggaa agattcgggt ttctctcaaa tgaccttccc tcggcatcgt      840
cacgtggaat attcacttt ggcatcttgc attgatagtg aacctcaaca ttcttcgttc      900
agacttggat ttgccaaaat gtttcatctt gccacggttc ttgacgatat ttacgacacc      960
tttggcacga tggatgagct agaactcttc acggcggcag ttaagaggtg gcatccgtct     1020
gcgacggagt ggcttccaga atatatgaaa ggagtatata tggtgcttta cgaaaccgtt     1080
aacgaaatgg caggagaagc agaaaagtct caaggccgag acacgctcaa ctatgcccga     1140
aatgctttgg aggcttatat tgatgcttct atgaaagaag cgaagtggat tttcagtggt     1200
tttttgccaa catttgagga gtacctggat aacgggaaag ttagtttcgg ttatagcatt     1260
ggcacattgc aacccattct gacgttgggc attcccttt ctcatcacat cctacaagaa     1320
atagactttc cttccaggct caatgatgtg gcatgttcca ttctccgact aaaaggcgac     1380
attcacactt acgaggctga gaggagccgt ggagaaaaat cttcgtgtat atcatgttat     1440
atggaagaga atcccgagtc aacagaggaa gatgcaatca atcatatcaa ctccatggtc     1500
gacaaattac tcaaggaact aaaattgggag tatctgagac ctgatagcaa tgttccaatc     1560
acttccaaga aacatgcatt tgacattctg agagctttct accatctcta caaataccga     1620
gatggcttca gcgttgcgaa ctatgaaata aagaatttgg tcatgacaac cgtcattgag     1680
cctgtgcctt tataa                                                     1695

<210> SEQ ID NO 12
<211> LENGTH: 1695
<212> TYPE: DNA
<213> ORGANISM: P. coulteri

<400> SEQUENCE: 12
agacgcatag ctggtcatca ttccaaccty tgggacgatr atttsataca gtccctytca       60
acgccttatg gggcaatttc gtaccatgaa agtgctcaga aacttattgg agaagtaaaa      120
gagatgatca attcaatctc ggttaaagat ggagaattaa tcaccccctc caatgatctc      180
cttatgcggc tctctatagt tgatagcatt gaacgtttgg gaatcgatag gcatttcaaa      240
agtgaaataa aatcagctct ggattatgtt tacagttatt ggaacgaaaa aggcattggg      300
tggggaagag atagtgttgt tgccgatctc aactcaactg ccttggggct tcgaactcta      360
cgactacacg gataccoggt gtcttcagat gtgttacaac acttcaaaga acaaaaaggg      420
cagtttgcat gttcggccat tcaaacagag ggagagataa gaagtgttct caacttattt      480
cgggcttccc aaattgcctt tccgggagag aaagttatgg aagaggcaga agtcttctct      540
acaatatatt taaaagaagc catactaaag cttccggtct gcggtctttc acgagagata      600
tcgtacgttc tggaatatgg ttggcatata aatttgccaa gattggaagc aaggaactac      660
atcgacgtat ttggagagga ccccatttat ttgacgccaa atatgaagac ccaaaaactt      720
```

| | |
|---|---:|
| ctagaacttg caaagttgga gttcaatatg tttcactctt tacaacagca agagctaaag | 780 |
| cttctctcca gatggtggaa agattcgggt ttctctcaaa tgaccttccc tcggcatcgt | 840 |
| cacgtggaat attacacttt ggcatcttgc attgatagtg aacctcaaca ttcttcgttc | 900 |
| agacttggat ttgccaaaat ctttcatctt gccacggttc ttgacgatat ttacgacacc | 960 |
| tttggcacga tggatgagct agaactcttc acggcggcag ttaagaggtg gcatccgtct | 1020 |
| gcgacggagt ggcttccaga atatatgaaa ggagtatata tggtgcttta cgaaaccgtt | 1080 |
| aacgaaatgg caggagaagc agaaaagtct caaggccgag acacgctcaa ctatggccga | 1140 |
| aatgctttgg aggcttatat tgatgcttct atggaagaag cgaagtggat tttcagtggt | 1200 |
| tttttgccaa catttgagga gtacctggat aacgggaaag ttagtttcgg ttatggcatt | 1260 |
| ggcacattgc aacccattct gacgttgggc attcccttc tcatcacat cctacaagaa | 1320 |
| atagactttc cttccaggct caatgatgtg gcatcttcca ttctccgact aaaaggcgac | 1380 |
| attcacactt accaggctga gaggagccgt ggagaaaaat cttcgtgtat atcatgttat | 1440 |
| atggaagaga atcccgagtc aacagaggaa gatgcaatca atcatatcaa ctccatggtc | 1500 |
| gacaaattac tcaaggaact aaattgggag tatctgagac ctgatagcaa tgttccaatc | 1560 |
| acttccaaga aacatgcatt tgacattctg agagctttct accatctcta caaataccga | 1620 |
| gatggcttca gcgttgcgaa ctatgaaata aagaatttgg tcatgacaac cgtcattgag | 1680 |
| cctgtgcctt tataa | 1695 |

<210> SEQ ID NO 13
<211> LENGTH: 1671
<212> TYPE: DNA
<213> ORGANISM: P. torreyana

<400> SEQUENCE: 13

| | |
|---|---:|
| aacctctggg acgatgattt gatacagtcc ctttcaacgc cttatggggc aatttcgtac | 60 |
| catgaaagtg ctcagaaact tattggagaa gtaaaagaga tgatcaattc aatctcggtt | 120 |
| aaagatggag aattaatcac cccctccaat gatctcctta tgcggctctc tatagttgat | 180 |
| agcattgaac gtttgggaat cgataggcat ttcaaaagtg aaataaaatc agctctggat | 240 |
| tatgttaca gttattggaa cgaaaaaggc attgggtggg aagagatag tgttgttgcc | 300 |
| gatctcaact caactgcctt ggggcttcga actctacgac tacacggata cccggtgtct | 360 |
| tcagatgtgt tacaacactt caaagaacaa aaagggcagt ttgcatgttc ggccattcaa | 420 |
| acagagggag agataagaag tgttctcaac ttatttcggg cttcccaaat tgccttccg | 480 |
| ggagagaaag ttatggaaga ggcagaagtc ttctctacaa tgtatttaaa agaagccata | 540 |
| ctaaagcttc cggtctgcgg tctttcacga gagatatcgt acgttctgga atatggttgg | 600 |
| catataaatt tgccaagatt ggaagcaagg aactacatcg acgtatttgg acaggacccc | 660 |
| atttatttga cgccaaatat gaagacccaa aaacttctag aacttgcaaa gttggagttc | 720 |
| aatatgtttc actcttaca acagcaagag ctaaagcttc tctccagatg gtggaaagat | 780 |
| tcgggtttct ctcaaatgac cttccctcgg catcgtcacg tggaatatta cactttggca | 840 |
| tcttgcattg atagtgaacc tcaacattct tcgttcagac ttggatttgc caaaatcttt | 900 |
| catcttgcca cggttcttga cgatatttac gaccctttg gcacgatgga tgagctagaa | 960 |
| ctcttcacgg cggcagttaa gaggtggcat ccgtctgcga cggagtggct tccagaatat | 1020 |
| atgaaaggag tatatatggt gctttacgaa accgttaacg aaatggcagg agaagcagaa | 1080 |
| aagtctcaag gccgagacac gctcaactat gcccgaaatg ctttggaggc ttatattgat | 1140 |

```
gcttctatgg aagaagcgaa gtggattttc agtggttttt tgccaacatt tgaggagtac    1200
ctggataacg ggaaagttag tttcggttat ggcattggca cattgcaacc cattctgacg    1260
ttgggcattc cctttcctca tcacatccta caagaaatag actttccttc caggctcaat    1320
gatgtggcat cttccattct ccgactaaaa ggcgacattc acacttacca ggctgagagg    1380
agccgtggag aaaaatcttc gtgtatatca tgttatatgg aagagaatcc cgagtcaaca    1440
gaggaagatg caatcaatca tatcaactcc atggtcgaca aattactcaa ggaactaaat    1500
tgggagtatc tgagacctga tagcaatgtt ccaatcactt ccaagaaaca tgcatttgac    1560
attctgagag ctttctacca tctctacaaa taccgagatg gcttcagcgt tgcgaactat    1620
gaaataaaga atttggtcat gacaaccgtc attgagcctg tgcctttata a             1671

<210> SEQ ID NO 14
<211> LENGTH: 1695
<212> TYPE: DNA
<213> ORGANISM: P. attenuata

<400> SEQUENCE: 14
agacgcagag gtgatttcca ttccaacctc tgggacgata atttcataca gtccctctca      60
acgccttatg gggcaatttc gtaccatgaa agtgctcaga aacttattgg agaagtaaaa     120
gagatgatca attcaatctc ggataaagat ggagaattaa tcaccccctc caatgatctc     180
cttatgctgc tctctatagt cgatagcatt gaacgtttgg gaatcgatag gcatttcaaa     240
agtgaaataa aatcagctct ggattatgtt tacagttatt ggaacgaaaa aggcattggg     300
tggggaagag atagtgttgt tgccgatctc aactcaactg ccttggggct tcgaactcta     360
cgactacacg gatacccggt gtcttcagac gtgttacaac acttcaaaga acaaaatggg     420
cagtttgcat gttcggccat tcaaacagag ggagagataa gaagtgttct caacttattt     480
cgggcttccc aaattgcctt tccgggagag aaagttatgg aagaggcaga agtcttctct     540
acaaaatatt taaagaagc catactaaag cttccggtct gcggtctttc acgagagata     600
tcgtacgttc tggaatatgg ttggcatatg aatttgccaa gattggaagc aaggaactac     660
atcgacgtat ttggacagga ccccatttat ttgacgccaa atatgaagac ccaaaaactt     720
ctagaacttg caaagttgga gttcaatatg tttcactctt tacaacagca agagctaaag     780
cttctctcca gatggtggaa agattcgggt ttctctcaaa tgaccttccc tcggcatcgt     840
cacgtggaat attacacttt ggcatcttgc attgatagtg aacctcaaca ttcttcgttc     900
agacttggat ttgccaaaat atttcatctt gccacggttc ttgacgatat ttacgacacc     960
tttggcacga tggatgagct agaactcttc acagcggcag ttaagaggtg catccgtct    1020 gcgacggagt ggcttccaga atatatgaaa ggagtatata tggtgcttta cgaaccgtt    1080 aacgaaatgg caggagaagc agaaaagtct caaggccgag acacgctcaa ctatgcccga    1140
aatgctttgg aggcttatat tgatgcttct atggaagaag cgaagtggat tttcagtggt    1200
tttttgccaa catttgagga gtacctggat aacgggaaag ttagtttcgg ttataccatt    1260
ggcacattgc aacccattct gacgttgggc attcccttc ctcatcacat cctacaagaa    1320
atagactttc cttccaggct caatgatgtg gcatgttcca ttctccgact aaaaggcgac    1380
gttcacactt accagcctga gaggagccgt ggagaagaat cttcgtgtat atcatgttat    1440
attgaagaga atcccgagtc aacagaggaa gatgcaatca atcatatcaa ctccatggtc    1500
gacaaattac tcaaggaact aaatttggag tatctgagac ctgatagcaa tgttccaatc    1560
```

```
acttccaaga acatgcatt tgacattctg agagctttgt accatctcta caaataccga    1620
gatggctaca gcgttgcgaa ctatgaaata agaatttgg tcatgacaac cgtcattgag    1680
cctgtgcctt tataa                                                    1695

<210> SEQ ID NO 15
<211> LENGTH: 1671
<212> TYPE: DNA
<213> ORGANISM: P. radiata

<400> SEQUENCE: 15
aacctctggg acgatgattt gatacagtcc ctttcaacgc cttatggggc aatttcgtac      60
catgaaagtg ctcagaaact tattggagaa gtaaaagaga tgatcaattc aatctcggat     120
aaaaatggag aattaatcac cccctccaat gatctcctta tgcggctctc tatagtcgat     180
agcattgaac gtttgggaat cgataggcat ttcaaaagtg aaataaaatc agctctggat     240
tatgtttaca gttattggaa cgaaaaaggc attgggtggg aagagatag tgttgttgcc      300 gatctcaact caactgcctt ggggcttcga actctacgac tacacggata cccggtgtct     360
tcagacgtgt tacaacactt caaagaacaa aatgggcagt ttgcatgttc ggccattcaa     420
acagagggag agataagaag tgttctcaac ttatttcggg cttcccaaat tgcctttccg     480
ggagagaaag ttatggaaga ggcagaagtc ttctctacaa aatatttaaa agaagccata     540
ctaaagcttc cggtctgcgg tctttcacga gagatatcgt acgttctgga atatggttgg     600
catatgaatt tgccaagatt ggaagcaagg aactacatcg acgtatttgg acaggacccc     660
atttatttga cgccaaatat gaagacccaa aaacttctag aacttgcaaa gttggagttc     720
aatatgtttc actctttaca acagcaagag ctaaagcttc tctccagatg gtggaaagat     780
tcgggtttct ctcaaatgac cttccctcgg catcgtcacg tggaatatta cactttggca     840
tcttgcattg atagtgaacc tcaacattct tcgttcagac ttggatttgc caaaatattt     900
catcttgcca cggttcttga cgatatttac gacacctttg gcacgatgga tgagctagaa     960
ctcttcacag cggcagttaa gaggtggcat ccgtctgcga cggagtggct tccagaatat    1020
atgaaaggag tatatatggt gctttacgaa accgttaacg aaatggcagg agaagcagaa    1080
aagtctcaag gccgagacac gctcaactat gcccgaaatg ctttggaggc ttatattgat    1140
gcttctatgg aagaagcgaa gtggattttc agtggttttt tgccaacatt tgaggagtac    1200
ctggataacg ggaaagttag tttcggttat accattggca cattgcaacc cattctgacg    1260
ttgggcattc ccttttcctca tcacatccta caagaaatag acttccttc caggctcaat    1320 gatgtggcat gttccattct ccgactaaaa ggcgacgttc acacttacca gcctgagagg    1380
agccgtggag aagaatcttc gtgtatatca tgttatatgg aagagaatcc cgagtcaaca    1440
gaggaagatg caatcaatca tatcaactcc atggtcgaca aattactcaa ggaactaaat    1500
tgggagtatc tgagacctga tagcaatgtt ccaatcactt ccaagaaaca tgcatttgac    1560
attctgagag ctttgtacca tctctacaaa taccgagatg ctacagcgt tgcgaactat    1620 gaaataaaga atttggtcat gacaactgtc attgagcctg tgccttata a              1671

<210> SEQ ID NO 16
<211> LENGTH: 1782
<212> TYPE: DNA
<213> ORGANISM: P. contorta

<400> SEQUENCE: 16
tctagcaagg ttaaggttgt ccgcagaacg atgtcaactt ccatccgcat gtgtcagata     60
```

```
accactgtat ccggtgaagg cgtacagaga cgcatagcaa atcatcattc caacctctgg    120
gacgataatt tcatacagtc cctctcaacg ccttatgggg caatttcgta ccatgaaagt    180
gctcagaaac ttattggaga agtaaaagag atgatcaatt caatctcggt taaagatgga    240
gaattaatca ccccctccaa tgatctcctt atgcggctct ctatagtcga tagcattgaa    300
cgtttgggaa tcgataggca tttcaaaagt gaaataaaat cagctctgga ttatgtttac    360
agttattgga acgaaaaagg cattgggtgg ggaagagata gtgttgttgc cgatctcaac    420
tcaactgcct ggggcttcg aactctacga ctacacggat acccggtgtc ttcagacgtg    480
ttacaacact tcaaagaaca aaagggcag tttgcatgtt cggccattca aacagaggga    540
gagataagaa gtgttctcaa cttatttcgg gcttcccaaa ttgcctttcc gggagagaaa    600
gttatggaag aggcagaagt cttctctaca aaatatttaa aagaagccat actaaagctt    660
ccggtctgcg gtcttcacg agagatatcg tacgttctgg aatatggttg gcatatgaat    720
ttgccaagat tggaagcaag gaactacatc gacgtatttg gacaggaccc catttatttg    780
acgccaaata tgaagaccca aaaacttcta gaacttgcta agttggagtt caatatgttt    840 cactcttac aacagcaaga gctaaagctt ctctccagat ggtggaaaga ttcgggtttc    900
tctcaaatga ccttccctcg gcatcgtcac gtggaatatt acactttggc atcttgcatt    960
gatagtgaac ctcaacattc ttcgttcaga cttggatttg ccaaaatatt tcatcttgcc   1020
acggttcttg acgatattta cgacacccttt ggcacgatgg atgagctaga actcttcaca   1080
gcggcagtta agaggtggca tccgtctgcg acggagtggc ttccagaata tatgaaagga   1140
gtatatatgg tgcttacga aaccgttaac gaaatggcag gagaagcaga aaagtctcaa   1200
ggccgagaca cgctcaacta tgcccgaaat gctttggagg cttatattga tgcttctatg   1260
gaagaagcga agtggatttt cagtggtttt ttgccaacat ttgaggagta cctggataac   1320
gggaaagtta gtttcggtta taccattggc acattgcaac ccattctgac gttgggcatt   1380 cccttcctc atcacatcct acaagaaata gactttcctt ccaggctcaa tgatgtggca   1440
tgttccattc tccgactaaa aggcgacatt cacacttacc agcctgagag gagccgtgga   1500
gaagaatctt cgtgtatatc atgttatatg gaagataatc ccgagtcaac agaggaagat   1560
gcaatcaatc atatcaactc catggtcgac aaattactca aggaactaaa ttgggagtat   1620
ctgagacctg atagcaatgt tccaatcact tccaagaaac atgcatttga cattctgaga   1680
gctttctacc atctctacaa ataccgagat ggctacagcg ttgcgaacta tgaaataaag   1740
aatttggtca tgacaactgt cattgagcct gtgcctttat aa                      1782

<210> SEQ ID NO 17
<211> LENGTH: 1782
<212> TYPE: DNA
<213> ORGANISM: P. contorta

<400> SEQUENCE: 17
tctagcaagg ttaaggttgt ccgcagaacg atgtcaactt ccatccgcat gtgtcagata     60
accactgtat ccggtgaagg cgtacagaga cgcatagcaa atcatcattc caacctctgg    120
gacgataatt tcatacagtc cctctcaacg ccttatgggg caatttcgta ccatgaaagt    180
gctcagaaac ttattggaga agtaaaagag atgatcaatt caatctcggt taaagatgga    240
gaattaatca ccccgtccaa tgatctcctt atgcggctct ctatagtcga tagcattgaa    300
cgtttgggaa tcgataggca tttcaaaagt gaaataaaat cagctctgga ttatgtttac    360
```

```
agttattgga acgaaaaagg cattgggtgg ggaagagata gtgttgttgc cgatctcaac    420
tcaactgcct tggggcttcg aactctacga ctacacggat acccggtgtc ttcagacgtg    480
ttacaacact tcaaagaaca aaagggcag tttgcatgtt cggccattca aacagaggga    540
gagataagaa gtgttctcaa cttatttcgg gcttcccaaa ttgcctttcc gggagagaaa    600
gttatggaag aggcagaagt cttctctaca aaatatttaa aagaagccat actaaagctt    660
ccggtctgcg gtcttttcacg agagatatcg tacgttctgg aatatggttg gcatataaat    720
ttgccaagat tggaagcaag gaactacatc gacgtatttg gacaggaccc catttatttg    780
acgccaaata tgaagaccca aaaacttcta gaacttgcaa agttggagtt caatatgttt    840
cactctttac aacagcaaga gctaaagctt ctctccagat ggtggaaaga ttcgggtttc    900
tctcaaatga ccttccctcg gcatcgtcac gtggaatatt acactttggc atcttgcatt    960
gatagtgaac ctcaacattc ttcgttcaga cttggatttg ccaaaatatt tcatcttgcc   1020
acggttcttg acgatattta cgacaccttt ggcacgatgg atgagctaga actcttcaca   1080
gcggcagtta agaggtggca tccgtctgcg acggagtggc ttccagaata tatgaaagga   1140
gtatatatgg tgctttacga aaccgttaac gaaatggcag gagaagcaga aaagtctcaa   1200
ggccgagaca cgctcaacta tgcccgaaat gctttggagg cttatattga tgcttctatg   1260
gaagaagcga gtggattttt cagtggtttt ttgccaacat tgaggagta cctggataac    1320
gggaaagtta gtttcggtta taccattggc acattgcaac ccattctgac gttgggcatt   1380
cccttttcctc atcacatcct acaagaaata gactttcctt ccaggctcaa tgatgtggca   1440
tgttccattc tccgactaaa aggcgacgtt cacacttacc aggctgagag gagccgtgga   1500
gaagaatctt cgtgtatatc atgttatatg aagataatc ccgagtcaac agaggaagat   1560
gcaatcaatc atatcaactc catggtcgac aaattactca aggaactaaa ttgggagtat   1620
ctgagacctg atagcaatgt tccaatcact tccaagaaac atgcatttga cattctgaga   1680
gctttctacc atctctacaa ataccgagat ggctacagcg ttgcgaacta tgaaataaag   1740
aatttggtca tgacaactgt cattgagcct gtgcctttat aa                      1782
```

<210> SEQ ID NO 18
<211> LENGTH: 593
<212> TYPE: PRT
<213> ORGANISM: P. patula

<400> SEQUENCE: 18

```
Ser Ser Lys Val Lys Val Arg Arg Thr Ile Ser Thr Ser Ile Arg
 1               5                  10                  15

Met Cys Arg Ile Thr Thr Val Ser Gly Glu Gly Val Gln Arg Ile
                20                  25                  30

Ala Asn His His Ser Asn Leu Trp Asp Asp Asn Phe Ile Gln Ser Leu
                35                  40                  45

Ser Thr Pro Tyr Gly Ala Ile Ser Tyr His Glu Ser Ala Gln Lys Leu
                50                  55                  60

Ile Gly Glu Val Lys Glu Met Ile Asn Ser Ile Ser Val Lys Asp Gly
65                  70                  75                  80

Glu Leu Ile Thr Pro Ser Asn Asp Leu Leu Met Arg Leu Ser Ile Val
                85                  90                  95

Asp Ser Ile Glu Arg Leu Gly Ile Asp Arg His Phe Lys Ser Glu Ile
               100                 105                 110

Lys Ser Ala Leu Asp Tyr Val Tyr Ser Tyr Trp Asn Glu Lys Gly Ile
               115                 120                 125
```

```
Gly Trp Gly Arg Asp Ser Val Val Ala Asp Leu Asn Ser Thr Ala Leu
130                 135                 140

Gly Leu Arg Thr Leu Arg Leu His Gly Tyr Pro Val Ser Ser Asp Val
145                 150                 155                 160

Leu Gln His Phe Lys Glu Gln Lys Gly Gln Phe Ala Cys Ser Ala Ile
                165                 170                 175

Gln Thr Glu Gly Glu Ile Arg Ser Val Leu Asn Leu Phe Arg Ala Ser
                180                 185                 190

Gln Ile Ala Phe Pro Gly Glu Lys Val Met Glu Glu Ala Glu Val Phe
            195                 200                 205

Ser Thr Ile Tyr Leu Lys Glu Ala Ile Leu Lys Leu Pro Val Cys Gly
210                 215                 220

Leu Ser Arg Glu Ile Ser Tyr Val Leu Glu Tyr Gly Trp His Ile Asn
225                 230                 235                 240

Leu Pro Arg Leu Glu Ala Arg Asn Tyr Ile Asp Val Phe Gly Gln Asp
                245                 250                 255

Pro Ile Tyr Leu Thr Pro Asn Met Lys Thr Gln Lys Leu Leu Glu Leu
                260                 265                 270

Ala Lys Leu Glu Phe Asn Met Phe His Ser Leu Gln Gln Gln Glu Leu
                275                 280                 285

Lys Leu Leu Ser Arg Trp Trp Lys Asp Ser Gly Phe Ser Gln Met Thr
290                 295                 300

Phe Pro Arg His Arg His Val Glu Tyr Tyr Thr Leu Ala Ser Cys Ile
305                 310                 315                 320

Asp Ser Glu Pro Gln His Ser Ser Phe Arg Leu Gly Phe Ala Lys Ile
                325                 330                 335

Phe His Leu Ala Thr Val Leu Asp Asp Ile Tyr Asp Thr Phe Gly Thr
                340                 345                 350

Met Asp Glu Leu Glu Leu Phe Thr Ala Ala Val Glu Arg Trp His Pro
            355                 360                 365

Ser Ala Thr Glu Trp Leu Pro Glu Tyr Met Lys Gly Val Tyr Met Val
370                 375                 380

Leu Tyr Glu Thr Val Asn Glu Met Ala Gly Glu Ala Glu Lys Ser Gln
385                 390                 395                 400

Gly Arg Asp Thr Leu Asn Tyr Ala Arg Asn Ala Leu Glu Ala Tyr Ile
                405                 410                 415

Asp Ala Ser Met Lys Glu Ala Lys Trp Ile Phe Ser Gly Phe Leu Pro
                420                 425                 430

Thr Phe Glu Glu Tyr Leu Asp Asn Gly Lys Val Ser Phe Gly Tyr Ser
            435                 440                 445

Ile Gly Thr Leu Gln Pro Ile Leu Thr Leu Gly Ile Pro Phe Pro His
450                 455                 460

His Ile Leu Gln Glu Ile Asp Phe Pro Ser Arg Leu Asn Asp Val Ala
465                 470                 475                 480

Cys Ser Ile Leu Arg Leu Lys Gly Asp Ile His Thr Tyr Gln Ala Glu
                485                 490                 495

Arg Ser Arg Gly Glu Lys Ser Ser Cys Ile Ser Cys Tyr Met Glu Glu
                500                 505                 510

Asn Pro Glu Ser Thr Glu Glu Asp Ala Ile Asp His Ile Asn Ser Met
            515                 520                 525

Val Asp Lys Leu Leu Lys Glu Leu Asn Arg Glu Tyr Leu Arg Pro Asp
530                 535                 540
```

```
Ser Asn Val Pro Ile Thr Ser Lys Lys His Ala Phe Asp Ile Leu Arg
545                 550                 555                 560

Ala Phe Tyr His Leu Tyr Lys Tyr Arg Asp Gly Phe Ser Val Ala Asn
            565                 570                 575

Tyr Glu Ile Lys Asn Leu Val Met Thr Thr Val Ile Glu Pro Val Pro
            580                 585                 590

Leu

<210> SEQ ID NO 19
<211> LENGTH: 593
<212> TYPE: PRT
<213> ORGANISM: P. pseudostrobus estevezii

<400> SEQUENCE: 19

Ser Ser Lys Val Lys Val Val Arg Arg Thr Ile Ser Thr Ser Ile Arg
1               5                   10                  15

Met Cys Arg Ile Thr Thr Val Ser Gly Glu Gly Val Gln Arg Arg Ile
            20                  25                  30

Ala Asn His His Ser Asn Leu Trp Asp Asp Asn Phe Ile Gln Ser Leu
            35                  40                  45

Ser Thr Pro Tyr Gly Ala Ile Ser Tyr His Gly Ser Ala Gln Lys Leu
        50                  55                  60

Ile Gly Glu Val Lys Glu Ile Ile Asn Ser Ile Ser Val Lys Asp Gly
65                  70                  75                  80

Glu Leu Ile Thr Pro Ser Asn Asp Leu Leu Met Arg Leu Ser Ile Val
                85                  90                  95

Asp Ser Ile Glu Arg Leu Gly Ile Asp Arg His Phe Lys Ser Glu Ile
            100                 105                 110

Lys Ser Ala Leu Asp Tyr Val Tyr Ser Tyr Trp Asn Glu Lys Gly Ile
        115                 120                 125

Gly Trp Gly Arg Asp Ser Val Val Ala Asp Leu Asn Ser Thr Ala Leu
130                 135                 140

Gly Leu Arg Thr Leu Arg Leu His Gly Tyr Pro Val Ser Ser Asp Val
145                 150                 155                 160

Leu Gln His Phe Lys Glu Gln Lys Gly Gln Phe Ala Cys Ser Ala Ile
                165                 170                 175

Gln Thr Glu Gly Glu Ile Arg Ser Val Leu Asn Leu Phe Arg Ala Ser
            180                 185                 190

Gln Ile Ala Phe Pro Gly Glu Lys Val Met Glu Glu Ala Glu Val Phe
        195                 200                 205

Ser Thr Ile Tyr Leu Lys Glu Ala Ile Leu Lys Leu Pro Val Cys Gly
    210                 215                 220

Leu Ser Arg Glu Ile Ser Tyr Val Leu Glu Tyr Gly Trp His Ile Asn
225                 230                 235                 240

Leu Pro Arg Leu Glu Ala Arg Asn Tyr Ile Asp Val Phe Gly Gln Asp
                245                 250                 255

Pro Ile Tyr Leu Thr Pro Asn Met Lys Thr Gln Lys Leu Leu Glu Leu
            260                 265                 270

Ala Lys Leu Glu Phe Asn Met Phe His Ser Leu Gln Gln Gln Glu Leu
        275                 280                 285

Lys Leu Leu Ser Arg Trp Trp Lys Asp Ser Gly Phe Ser Gln Met Thr
    290                 295                 300

Phe Pro Arg His Arg His Val Glu Tyr Tyr Thr Leu Ala Ser Cys Ile
305                 310                 315                 320
```

Asp Ser Glu Pro Gln His Ser Phe Arg Leu Gly Phe Ala Lys Ile
                325                 330                 335

Phe His Leu Ala Thr Val Leu Asp Asp Ile Tyr Asp Thr Phe Gly Thr
            340                 345                 350

Met Asp Glu Leu Glu Leu Phe Thr Ala Ala Val Lys Arg Trp His Pro
            355                 360                 365

Ser Ala Thr Glu Trp Leu Pro Glu Tyr Met Lys Gly Val Tyr Met Val
        370                 375                 380

Leu Tyr Glu Thr Val Asn Glu Met Ala Gly Ala Glu Lys Ser Gln
385                 390                 395                 400

Gly Arg Asp Thr Leu Asn Tyr Ala Arg Asn Ala Leu Glu Ala Tyr Ile
                405                 410                 415

Asp Ala Ser Met Lys Glu Ala Lys Trp Ile Phe Ser Gly Phe Leu Pro
            420                 425                 430

Thr Phe Glu Glu Tyr Leu Asp Asn Gly Lys Val Ser Phe Gly Tyr Ser
            435                 440                 445

Ile Gly Thr Leu Gln Pro Ile Leu Thr Leu Gly Ile Pro Phe Pro His
        450                 455                 460

His Ile Leu Gln Glu Ile Asp Phe Pro Ser Arg Leu Asn Asp Val Ala
465                 470                 475                 480

Cys Ser Ile Leu Arg Leu Lys Gly Asp Ile His Thr Tyr Gln Ala Glu
                485                 490                 495

Arg Ser Arg Gly Glu Lys Ser Ser Cys Ile Ser Cys Tyr Met Glu Glu
            500                 505                 510

Asn Pro Glu Ser Thr Glu Glu Asp Ala Ile Asn His Val Asn Ser Met
            515                 520                 525

Val Asp Lys Leu Leu Lys Glu Leu Asn Trp Glu Tyr Leu Arg Pro Asp
        530                 535                 540

Ser Asn Val Pro Ile Thr Ser Lys Lys His Ala Phe Asp Ile Leu Arg
545                 550                 555                 560

Ala Phe Tyr His Leu Tyr Lys Tyr Arg Asp Gly Phe Ser Val Ala Asn
                565                 570                 575

Tyr Glu Ile Lys Asn Leu Val Met Thr Thr Val Ile Glu Pro Val Pro
            580                 585                 590

Leu

<210> SEQ ID NO 20
<211> LENGTH: 593
<212> TYPE: PRT
<213> ORGANISM: P. cooperi ornelasi

<400> SEQUENCE: 20

Ser Ser Lys Val Lys Val Val Arg Arg Thr Ile Ser Thr Ser Ile Arg
1               5                   10                  15

Met Cys Arg Ile Thr Thr Val Ser Gly Glu Gly Val Gln Arg Arg Ile
            20                  25                  30

Ala Asn His His Ser Asn Leu Trp Asp Asp Asn Phe Ile Gln Ser Leu
        35                  40                  45

Ser Thr Pro Tyr Gly Ala Ile Ser Tyr His Glu Ser Ala Gln Lys Leu
    50                  55                  60

Ile Gly Glu Val Lys Glu Met Ile Asn Ser Ile Ser Val Lys Asp Gly
65                  70                  75                  80

Glu Leu Ile Thr Pro Ser Asn Asp Leu Leu Met Arg Leu Ser Ile Val
                85                  90                  95

-continued

```
Asp Ser Ile Glu Arg Leu Gly Ile Asp Arg His Phe Lys Ser Glu Ile
            100                 105                 110
Lys Ser Ala Leu Asp Tyr Val Tyr Ser Tyr Trp Asn Glu Lys Gly Ile
        115                 120                 125
Gly Trp Gly Arg Asp Ser Val Val Ala Asp Leu Asn Ser Thr Ala Leu
    130                 135                 140
Gly Leu Arg Thr Leu Arg Leu His Gly Tyr Pro Val Ser Ser Asp Val
145                 150                 155                 160
Leu Gln His Phe Lys Glu Gln Lys Gly Gln Phe Ala Cys Ser Ala Ile
                165                 170                 175
Gln Thr Glu Gly Glu Ile Arg Ser Val Leu Asn Leu Phe Arg Ala Ser
            180                 185                 190
Gln Ile Ala Phe Pro Gly Glu Lys Val Met Glu Glu Ala Glu Val Phe
        195                 200                 205
Ser Thr Ile Tyr Leu Lys Glu Ala Ile Leu Lys Leu Pro Val Cys Gly
    210                 215                 220
Leu Ser Arg Glu Ile Ser Tyr Val Leu Glu Tyr Gly Trp His Ile Asn
225                 230                 235                 240
Leu Pro Arg Leu Glu Ala Arg Asn Tyr Ile Asp Val Phe Gly Gln Asp
                245                 250                 255
Pro Ile Tyr Leu Thr Pro Asn Met Lys Thr Gln Lys Leu Leu Glu Leu
            260                 265                 270
Ala Lys Leu Glu Phe Asn Met Phe His Ser Leu Gln Gln Gln Glu Leu
        275                 280                 285
Lys Leu Leu Ser Arg Trp Trp Lys Asp Ser Gly Phe Ser Gln Met Thr
    290                 295                 300
Phe Pro Arg His Arg His Val Glu Tyr Tyr Thr Leu Ala Ser Cys Ile
305                 310                 315                 320
Asp Ser Glu Pro Gln His Ser Ser Phe Arg Leu Gly Phe Ala Lys Ile
                325                 330                 335
Phe His Leu Ala Thr Val Leu Asp Asp Ile Tyr Asp Thr Phe Gly Thr
            340                 345                 350
Met Asp Glu Leu Glu Leu Phe Thr Ala Ala Val Lys Arg Trp His Pro
        355                 360                 365
Ser Ala Thr Glu Trp Leu Pro Glu Tyr Met Lys Gly Val Tyr Met Val
    370                 375                 380
Leu Tyr Glu Thr Val Asn Glu Met Ala Gly Glu Ala Glu Lys Ser Gln
385                 390                 395                 400
Gly Arg Asp Thr Leu Asn Tyr Ala Arg Asn Ala Leu Glu Ala Tyr Ile
                405                 410                 415
Asp Ala Ser Met Lys Glu Ala Lys Trp Ile Phe Ser Gly Phe Leu Pro
            420                 425                 430
Thr Phe Glu Glu Tyr Leu Asp Asn Gly Lys Val Ser Phe Gly Tyr Ser
        435                 440                 445
Ile Gly Thr Leu Gln Pro Ile Leu Thr Leu Gly Ile Pro Phe Pro His
    450                 455                 460
His Ile Leu Gln Glu Ile Asp Phe Pro Ser Arg Leu Asn Asp Val Ala
465                 470                 475                 480
Cys Ser Ile Leu Arg Leu Lys Gly Asp Ile His Thr Tyr Gln Ala Glu
                485                 490                 495
Arg Ser Arg Gly Glu Lys Ser Ser Cys Ile Ser Cys Tyr Met Glu Glu
            500                 505                 510
Asn Pro Glu Ser Thr Glu Glu Asp Ala Ile Asn His Ile Asn Ser Met
```

```
                515                 520                 525
Val Asp Lys Leu Leu Lys Glu Leu Asn Trp Glu Tyr Leu Arg Pro Asp
    530                 535                 540

Ser Asn Val Pro Ile Thr Ser Lys Lys His Ala Phe Asp Ile Leu Thr
545                 550                 555                 560

Ala Phe Tyr His Leu Tyr Lys Tyr Arg Asp Gly Phe Ser Val Ala Asn
                565                 570                 575

Tyr Glu Ile Lys Asn Leu Val Met Thr Thr Val Ile Glu Pro Val Pro
            580                 585                 590

Leu

<210> SEQ ID NO 21
<211> LENGTH: 593
<212> TYPE: PRT
<213> ORGANISM: P. hartwegii

<400> SEQUENCE: 21

Ser Ser Lys Val Lys Val Val Arg Arg Thr Ile Ser Thr Ser Ile Arg
1               5                   10                  15

Met Cys Arg Ile Thr Thr Val Ser Gly Glu Gly Val Gln Arg Arg Ile
            20                  25                  30

Ala Asn His His Ser Asn Leu Trp Asp Asp Asn Phe Ile Gln Ser Leu
        35                  40                  45

Ser Thr Pro Tyr Gly Ala Ile Ser Tyr His Glu Ser Ala Gln Lys Leu
    50                  55                  60

Ile Gly Glu Val Lys Glu Met Ile Asn Ser Ile Ser Val Lys Asp Gly
65                  70                  75                  80

Glu Leu Ile Thr Pro Ser Asn Asp Leu Leu Met Arg Leu Ser Ile Val
                85                  90                  95

Asp Ser Ile Glu Arg Leu Gly Ile Asp Arg His Phe Lys Ser Glu Ile
            100                 105                 110

Lys Ser Ala Leu Asp Tyr Val Tyr Ser Tyr Trp Asn Glu Lys Gly Ile
        115                 120                 125

Gly Trp Gly Arg Asp Ser Val Val Ala Asp Leu Asn Ser Thr Ala Leu
    130                 135                 140

Gly Leu Arg Thr Leu Arg Leu His Gly Tyr Pro Val Ser Ser Asp Val
145                 150                 155                 160

Leu Gln His Phe Lys Glu Gln Lys Gly Gln Phe Ala Cys Ser Ala Ile
                165                 170                 175

Gln Thr Glu Gly Glu Ile Arg Ser Val Leu Asn Leu Phe Arg Ala Ser
            180                 185                 190

Gln Ile Ala Phe Pro Gly Glu Lys Val Met Glu Glu Ala Glu Val Phe
        195                 200                 205

Ser Thr Ile Tyr Leu Lys Glu Ala Ile Leu Lys Leu Pro Val Cys Gly
    210                 215                 220

Leu Ser Arg Glu Ile Ser Tyr Val Leu Glu Tyr Gly Trp His Ile Asn
225                 230                 235                 240

Leu Pro Arg Leu Glu Ala Arg Asn Tyr Ile Asp Val Phe Gly Gln Asp
                245                 250                 255

Pro Ile Tyr Leu Thr Pro Asn Met Lys Thr Gln Lys Leu Leu Glu Leu
            260                 265                 270

Ala Lys Leu Glu Phe Asn Met Phe His Ser Leu Gln Gln Gln Glu Leu
        275                 280                 285

Lys Leu Leu Ser Arg Trp Trp Lys Asp Ser Gly Phe Ser Gln Met Thr
```

```
                290                 295                 300
Phe Pro Arg His Arg His Val Glu Tyr Tyr Thr Leu Ala Ser Cys Ile
305                 310                 315                 320

Asp Ser Glu Pro Gln Tyr Ser Ser Phe Arg Leu Gly Phe Ala Lys Ile
                325                 330                 335

Phe His Leu Ala Thr Val Leu Asp Asp Ile Tyr Asp Thr Phe Gly Thr
            340                 345                 350

Met Asp Glu Leu Glu Leu Phe Thr Ala Ala Val Lys Arg Trp His Pro
        355                 360                 365

Ser Ala Thr Glu Trp Leu Pro Glu Tyr Met Lys Gly Val Tyr Met Val
    370                 375                 380

Leu Tyr Glu Thr Val Asn Glu Met Ala Gly Glu Ala Glu Lys Ser Gln
385                 390                 395                 400

Gly Arg Asp Thr Leu Asn Tyr Ala Arg Asn Ala Leu Glu Ala Tyr Ile
                405                 410                 415

Asp Ala Ser Met Lys Glu Ala Lys Trp Ile Phe Ser Gly Phe Leu Pro
            420                 425                 430

Thr Phe Glu Glu Tyr Leu Asp Asn Gly Lys Val Ser Phe Gly Tyr Ser
        435                 440                 445

Ile Gly Thr Leu Gln Pro Ile Leu Thr Leu Gly Ile Pro Phe Pro His
    450                 455                 460

His Ile Leu Gln Glu Ile Asp Phe Pro Ser Arg Leu Asn Asp Val Ala
465                 470                 475                 480

Cys Ser Ile Leu Arg Leu Lys Gly Asp Ile His Thr Tyr Gln Ala Glu
                485                 490                 495

Arg Ser Arg Gly Glu Lys Ser Ser Cys Ile Ser Cys Tyr Met Glu Glu
            500                 505                 510

Asn Pro Glu Ser Thr Glu Asp Ala Ile Asn His Ile Asn Ser Met
        515                 520                 525

Val Asp Lys Leu Leu Lys Glu Leu Asn Trp Glu Tyr Leu Arg Pro Asp
    530                 535                 540

Ser Asn Val Pro Ile Thr Ser Lys Lys His Ala Phe Asp Ile Leu Arg
545                 550                 555                 560

Ala Phe Tyr His Leu Tyr Lys Tyr Arg Asp Gly Phe Ser Val Ala Asn
                565                 570                 575

Tyr Glu Ile Lys Asn Leu Val Met Thr Thr Val Ile Glu Pro Val Pro
            580                 585                 590

Leu

<210> SEQ ID NO 22
<211> LENGTH: 593
<212> TYPE: PRT
<213> ORGANISM: P. ponderosa

<400> SEQUENCE: 22

Ser Ser Lys Val Lys Val Val Arg Arg Thr Ile Ser Thr Ser Ile Arg
1               5                   10                  15

Met Cys Arg Ile Thr Thr Glu Ser Gly Glu Gly Val Gln Arg Arg Ile
            20                  25                  30

Ala Asn His His Ser Asn Leu Trp Asp Asp Asn Phe Ile Gln Ser Leu
        35                  40                  45

Ser Thr Pro Tyr Gly Ala Ile Ser Tyr His Glu Ser Ala Gln Lys Leu
    50                  55                  60

Ile Gly Glu Val Lys Glu Met Ile Asn Ser Ile Ser Leu Lys Asp Gly
```

```
                65                  70                  75                  80
Glu Leu Ile Thr Pro Ser Asn Asp Leu Leu Met Arg Leu Ser Ile Val
                            85                  90                  95
Asp Ser Ile Glu Arg Leu Gly Ile Asp Arg His Phe Lys Ser Glu Ile
                100                 105                 110
Lys Ser Ala Leu Asp Tyr Val Tyr Ser Tyr Trp Asn Glu Lys Gly Ile
                115                 120                 125
Gly Trp Gly Arg Asp Ser Val Val Ala Asp Leu Asn Ser Thr Ala Leu
        130                 135                 140
Gly Leu Arg Thr Leu Arg Leu His Gly Tyr Pro Val Ser Ser Asp Val
145                 150                 155                 160
Leu Gln His Phe Lys Glu Gln Lys Gly Gln Phe Ala Cys Ser Ala Ile
                    165                 170                 175
Gln Thr Glu Gly Glu Ile Arg Ser Val Leu Asn Leu Phe Arg Ala Ser
                180                 185                 190
Gln Ile Ala Phe Pro Gly Glu Lys Val Met Glu Glu Ala Glu Val Phe
            195                 200                 205
Ser Thr Ile Tyr Leu Lys Glu Ala Ile Leu Lys Leu Pro Val Cys Gly
        210                 215                 220
Leu Ser Arg Glu Ile Ser Tyr Val Leu Glu Tyr Gly Trp His Ile Asn
225                 230                 235                 240
Leu Pro Arg Leu Glu Ala Arg Asn Tyr Ile Asp Val Phe Gly Gln Asp
                245                 250                 255
Pro Ile Tyr Leu Thr Pro Asn Met Lys Thr Gln Lys Leu Leu Glu Leu
                260                 265                 270
Ala Lys Leu Glu Phe Asn Met Phe His Ser Leu Gln Gln Gln Glu Leu
            275                 280                 285
Lys Leu Leu Ser Arg Trp Trp Lys Asp Ser Gly Phe Ser Gln Met Thr
        290                 295                 300
Phe Pro Arg His Arg His Val Glu Tyr Tyr Thr Leu Ala Ser Cys Ile
305                 310                 315                 320
Asp Ser Glu Pro Gln His Ser Ser Phe Arg Leu Gly Phe Ala Lys Ile
                325                 330                 335
Phe His Leu Ala Thr Val Leu Asp Asp Ile Tyr Asp Thr Phe Gly Thr
            340                 345                 350
Met Asp Glu Leu Glu Leu Phe Thr Ala Ala Val Lys Arg Trp His Pro
        355                 360                 365
Ser Ala Thr Glu Trp Leu Pro Glu Tyr Met Lys Gly Val Tyr Met Val
370                 375                 380
Leu Tyr Glu Thr Val Asn Glu Met Ala Arg Glu Ala Glu Lys Ser Gln
385                 390                 395                 400
Gly Arg Asp Thr Leu Asn Tyr Ala Arg Asn Ala Leu Glu Ala Tyr Ile
                405                 410                 415
Asp Ala Ser Met Lys Glu Ala Lys Trp Ile Phe Ser Gly Phe Leu Pro
                420                 425                 430
Thr Phe Glu Glu Tyr Leu Asp Asn Gly Lys Val Ser Phe Gly Tyr Ser
            435                 440                 445
Ile Gly Thr Leu Gln Pro Ile Leu Thr Leu Gly Ile Pro Phe Pro His
        450                 455                 460
His Ile Leu Gln Glu Ile Asp Phe Pro Ser Arg Leu Asn Asp Val Ala
465                 470                 475                 480
Cys Ser Ile Leu Arg Leu Lys Gly Asp Ile His Thr Tyr Gln Ala Glu
                485                 490                 495
```

```
Arg Ser Arg Gly Glu Lys Ser Ser Cys Ile Ser Cys Tyr Met Glu Glu
            500                 505                 510

Asn Pro Glu Ser Thr Glu Glu Asp Ala Ile Asn His Ile Asn Ser Met
            515                 520                 525

Val Asp Lys Leu Leu Lys Glu Leu Asn Trp Glu Tyr Leu Arg Pro Asp
530                 535                 540

Ser Asn Val Pro Ile Thr Ser Lys Lys His Ala Phe Asp Ile Leu Arg
545                 550                 555                 560

Thr Phe Tyr His Leu Tyr Lys Tyr Arg Asp Gly Phe Ser Val Ala Asn
                565                 570                 575

Tyr Glu Ile Lys Asn Leu Val Met Thr Thr Val Ile Glu Pro Val Pro
            580                 585                 590

Leu

<210> SEQ ID NO 23
<211> LENGTH: 593
<212> TYPE: PRT
<213> ORGANISM: P. ponderosa

<400> SEQUENCE: 23

Ser Ser Lys Val Lys Val Val Arg Arg Thr Ile Ser Thr Ser Ile Arg
1               5                   10                  15

Met Cys Arg Ile Thr Thr Glu Ser Gly Glu Gly Val Gln Arg Arg Ile
            20                  25                  30

Ala Asn His His Ser Asn Leu Trp Asp Asp Asn Phe Ile Gln Ser Leu
        35                  40                  45

Ser Thr Pro Tyr Gly Ala Ile Ser Tyr His Glu Ser Ala Gln Lys Leu
    50                  55                  60

Ile Gly Glu Val Lys Glu Met Ile Asn Ser Ile Ser Leu Lys Asp Gly
65                  70                  75                  80

Glu Leu Ile Thr Pro Ser Asn Asp Leu Leu Met Arg Leu Ser Ile Val
                85                  90                  95

Asp Ser Ile Glu Arg Leu Gly Ile Asp Arg His Phe Lys Ser Glu Ile
            100                 105                 110

Lys Ser Ala Leu Asp Tyr Val Tyr Ser Tyr Trp Asn Glu Lys Gly Ile
        115                 120                 125

Gly Trp Gly Arg Asp Ser Val Val Ala Asp Leu Asn Ser Thr Ala Leu
    130                 135                 140

Gly Leu Arg Thr Leu Arg Leu His Gly Tyr Pro Val Ser Ser Asp Val
145                 150                 155                 160

Leu Gln His Phe Lys Glu Gln Lys Gly Gln Phe Ala Cys Ser Ala Ile
                165                 170                 175

Gln Thr Glu Gly Glu Ile Arg Ser Val Leu Asn Leu Phe Arg Ala Ser
            180                 185                 190

Gln Ile Ala Phe Pro Gly Glu Lys Val Met Glu Glu Ala Glu Val Phe
        195                 200                 205

Ser Thr Ile Tyr Leu Lys Glu Ala Ile Leu Lys Leu Pro Val Cys Gly
    210                 215                 220

Leu Ser Arg Glu Ile Ser Tyr Val Leu Glu Tyr Gly Trp His Ile Asn
225                 230                 235                 240

Leu Pro Arg Leu Glu Ala Arg Asn Tyr Ile Asp Val Phe Gly Gln Asp
                245                 250                 255

Pro Ile Tyr Leu Thr Pro Asn Met Lys Thr Gln Lys Phe Leu Glu Leu
            260                 265                 270
```

Ala Lys Leu Glu Phe Asn Met Phe His Ser Leu Gln Gln Gln Glu Leu
            275                 280                 285

Lys Leu Leu Ser Arg Trp Trp Lys Asp Ser Gly Phe Ser Gln Met Thr
        290                 295                 300

Phe Pro Arg His Arg His Val Glu Tyr Tyr Thr Leu Ala Ser Cys Ile
305                 310                 315                 320

Asp Ser Glu Pro Gln His Ser Ser Phe Arg Leu Gly Phe Ala Lys Ile
                325                 330                 335

Phe His Leu Ala Thr Val Leu Asp Asp Ile Tyr Asp Thr Phe Gly Thr
            340                 345                 350

Met Asp Glu Leu Glu Leu Phe Thr Ala Ala Val Lys Arg Trp His Pro
        355                 360                 365

Ser Ala Thr Glu Trp Leu Pro Glu Tyr Met Lys Gly Val Tyr Met Val
    370                 375                 380

Leu Tyr Glu Thr Val Asn Glu Met Ala Arg Glu Ala Glu Lys Ser Gln
385                 390                 395                 400

Gly Arg Asp Thr Leu Asn Tyr Ala Arg Asn Ala Leu Glu Ala Tyr Ile
                405                 410                 415

Asp Ala Ser Met Lys Glu Ala Lys Trp Ile Phe Ser Gly Phe Leu Pro
            420                 425                 430

Thr Phe Glu Glu Tyr Leu Tyr Asn Gly Lys Val Ser Phe Gly Tyr Ser
        435                 440                 445

Ile Gly Thr Leu Gln Pro Ile Leu Thr Leu Gly Ile Pro Phe Pro His
    450                 455                 460

His Ile Leu Gln Glu Ile Asp Phe Pro Ser Arg Leu Asn Asp Val Ala
465                 470                 475                 480

Cys Ser Ile Leu Arg Leu Lys Gly Asp Ile His Thr Tyr Gln Ala Glu
                485                 490                 495

Arg Ser Arg Gly Glu Lys Ser Ser Cys Ile Ser Cys Tyr Met Glu Glu
            500                 505                 510

Asn Pro Glu Ser Thr Glu Glu Asp Ala Ile Asn His Ile Asn Ser Met
        515                 520                 525

Val Asp Lys Leu Leu Lys Glu Leu Asn Trp Glu Tyr Leu Arg Pro Asp
    530                 535                 540

Ser Asn Val Pro Ile Thr Ser Lys Lys His Ala Phe Asp Ile Leu Arg
545                 550                 555                 560

Thr Phe Tyr His Leu Tyr Lys Tyr Arg Asp Gly Phe Ser Val Ala Asn
                565                 570                 575

Tyr Glu Ile Lys Asn Leu Val Met Thr Thr Val Ile Glu Pro Val Pro
            580                 585                 590

Leu

<210> SEQ ID NO 24
<211> LENGTH: 593
<212> TYPE: PRT
<213> ORGANISM: P. jeffreyi

<400> SEQUENCE: 24

Ser Ser Lys Val Lys Val Val Arg Arg Thr Ile Ser Thr Ser Ile Arg
1               5                   10                  15

Met Cys Arg Ile Thr Thr Glu Ser Gly Glu Gly Val Gln Arg Arg Ile
            20                  25                  30

Ala Asn His His Ser Asn Leu Trp Asp Asp Asn Phe Ile Gln Ser Leu
        35                  40                  45

```
Ser Thr Pro Tyr Gly Ala Ile Ser Tyr His Glu Ser Ala Gln Lys Leu
    50                  55                  60

Ile Gly Glu Val Lys Glu Met Ile Asn Ser Ile Ser Leu Lys Asp Gly
65                  70                  75                  80

Glu Leu Ile Thr Pro Ser Asn Asp Leu Leu Met Arg Leu Ser Ile Val
                85                  90                  95

Asp Ser Ile Glu Arg Leu Gly Ile Asp Arg His Phe Lys Ser Glu Ile
                100                 105                 110

Lys Ser Ala Leu Asp Tyr Val Tyr Ser Tyr Trp Asn Glu Lys Gly Ile
            115                 120                 125

Gly Trp Gly Arg Asp Ser Val Val Ala Asp Leu Asn Ser Thr Ala Leu
    130                 135                 140

Gly Leu Arg Thr Leu Arg Leu His Gly Tyr Pro Val Ser Ser Asp Val
145                 150                 155                 160

Leu Gln His Phe Lys Glu Gln Lys Gly Gln Phe Ala Cys Ser Ala Ile
                165                 170                 175

Gln Thr Glu Gly Glu Ile Arg Ser Val Leu Asn Leu Phe Arg Ala Ser
                180                 185                 190

Gln Ile Ala Phe Pro Gly Glu Lys Val Met Glu Glu Ala Glu Val Phe
            195                 200                 205

Ser Thr Ile Tyr Leu Lys Glu Ala Ile Leu Lys Leu Pro Val Cys Gly
    210                 215                 220

Leu Ser Arg Glu Ile Ser Tyr Val Leu Glu Tyr Gly Trp His Ile Asn
225                 230                 235                 240

Leu Pro Arg Leu Glu Ala Arg Asn Tyr Ile Asp Val Phe Gly Gln Asp
                245                 250                 255

Pro Ile Tyr Leu Thr Pro Asn Met Lys Thr Gln Lys Leu Leu Glu Leu
                260                 265                 270

Ala Lys Leu Glu Phe Asn Met Phe His Ser Leu Gln Gln Gln Glu Leu
            275                 280                 285

Lys Leu Leu Ser Arg Trp Trp Lys Asp Ser Gly Phe Ser Gln Met Thr
    290                 295                 300

Phe Pro Arg His Arg His Val Glu Tyr Tyr Thr Leu Ala Ser Cys Ile
305                 310                 315                 320

Asp Ser Glu Pro Gln His Ser Ser Phe Arg Leu Gly Phe Ala Lys Ile
                325                 330                 335

Phe His Leu Ala Thr Val Leu Asp Asp Ile Tyr Asp Thr Phe Gly Thr
                340                 345                 350

Met Asp Glu Leu Glu Leu Phe Thr Ala Ala Val Lys Arg Trp His Pro
            355                 360                 365

Ser Ala Thr Glu Trp Leu Pro Glu Tyr Met Lys Gly Val Tyr Met Val
    370                 375                 380

Leu Tyr Glu Thr Val Asn Glu Met Ala Gly Glu Ala Glu Lys Ser Gln
385                 390                 395                 400

Gly Arg Asp Thr Leu Asn Tyr Ala Arg Asn Ala Ser Glu Ala Tyr Ile
                405                 410                 415

Asp Ala Ser Met Lys Glu Ala Lys Trp Ile Phe Ser Gly Phe Leu Pro
                420                 425                 430

Thr Phe Glu Glu Tyr Leu Asp Asn Gly Lys Val Ser Phe Gly Tyr Ser
            435                 440                 445

Ile Gly Thr Leu Gln Pro Ile Leu Thr Leu Gly Ile Pro Phe Pro His
    450                 455                 460
```

His Ile Leu Gln Glu Ile Asp Phe Pro Ser Arg Leu Asn Asp Val Ala
465                 470                 475                 480

Cys Ser Ile Leu Arg Leu Lys Gly Asp Ile His Thr Tyr Gln Ala Glu
            485                 490                 495

Arg Ser Arg Gly Glu Lys Ser Ser Cys Ile Ser Cys Tyr Met Glu Glu
        500                 505                 510

Asn Pro Glu Ser Thr Glu Glu Asp Ala Ile Asn His Ile Asn Ser Met
    515                 520                 525

Val Asp Lys Leu Leu Lys Glu Leu Asn Trp Glu Tyr Leu Arg Pro Asp
530                 535                 540

Ser Asn Val Pro Ile Thr Ser Lys Lys His Ala Phe Asp Ile Leu Arg
545                 550                 555                 560

Ala Phe Tyr His Leu Tyr Lys Tyr Arg Asp Gly Phe Ser Val Ala Asn
            565                 570                 575

Tyr Glu Ile Lys Asn Leu Val Met Thr Thr Val Ile Glu Pro Val Pro
        580                 585                 590

Leu

<210> SEQ ID NO 25
<211> LENGTH: 593
<212> TYPE: PRT
<213> ORGANISM: P. montezumae

<400> SEQUENCE: 25

Ser Ser Lys Val Lys Val Arg Arg Thr Ile Ser Thr Ser Ile Arg
1               5                   10                  15

Met Cys Arg Ile Thr Thr Val Ser Gly Glu Gly Val Gln Arg Arg Ile
            20                  25                  30

Ala Asn His His Ser Asn Leu Trp Asp Asp Asn Phe Ile Gln Ser Leu
        35                  40                  45

Ser Thr Pro Tyr Gly Ala Ile Ser Tyr His Glu Ser Ala Gln Lys Leu
    50                  55                  60

Ile Gly Glu Val Lys Glu Met Ile Asn Ser Ile Ser Val Lys Asp Gly
65                  70                  75                  80

Glu Leu Ile Thr Pro Ser Asn Asp Leu Leu Met Arg Leu Ser Ile Val
                85                  90                  95

Asp Ser Ile Glu Arg Leu Gly Ile Asp Arg His Phe Lys Ser Glu Ile
            100                 105                 110

Lys Ser Ala Leu Asp Tyr Val Tyr Ser Tyr Trp Asn Glu Lys Gly Ile
        115                 120                 125

Gly Trp Gly Arg Asp Ser Val Val Ala Asp Leu Asn Ser Thr Ala Leu
130                 135                 140

Gly Leu Arg Thr Leu Arg Leu His Gly Tyr Pro Val Ser Ser Asp Val
145                 150                 155                 160

Leu Gln His Phe Lys Glu Gln Lys Gly Gln Phe Ala Cys Ser Ala Ile
                165                 170                 175

Gln Thr Glu Gly Glu Ile Arg Ser Val Leu Asn Leu Phe Arg Ala Ser
            180                 185                 190

Gln Ile Ala Phe Pro Gly Glu Lys Val Met Glu Glu Ala Glu Val Phe
        195                 200                 205

Ser Thr Ile Tyr Leu Lys Glu Ala Ile Leu Lys Leu Pro Val Cys Gly
    210                 215                 220

Leu Ser Arg Glu Ile Ser Tyr Val Leu Glu Tyr Gly Trp His Ile Asn
225                 230                 235                 240

```
Leu Pro Arg Leu Glu Ala Arg Asn Tyr Ile Asp Val Phe Gly Gln Asp
                245                 250                 255

Pro Ile Tyr Leu Thr Pro Asn Met Lys Thr Gln Lys Leu Leu Glu Leu
            260                 265                 270

Ala Lys Leu Glu Phe Asn Met Phe His Ser Leu Gln Gln Gln Glu Leu
        275                 280                 285

Lys Leu Leu Ser Arg Trp Trp Lys Asp Ser Gly Phe Ser Gln Met Thr
290                 295                 300

Phe Pro Arg His Arg His Val Glu Tyr Tyr Thr Leu Ala Ser Cys Ile
305                 310                 315                 320

Asp Ser Glu Pro Gln His Ser Ser Phe Arg Leu Gly Phe Ala Lys Met
                325                 330                 335

Phe His Leu Ala Thr Val Leu Asp Asp Ile Tyr Asp Thr Phe Gly Thr
            340                 345                 350

Met Asp Glu Leu Glu Leu Phe Thr Ala Ala Val Lys Arg Trp His Pro
        355                 360                 365

Ser Ala Thr Glu Trp Leu Pro Glu Tyr Met Lys Gly Val Tyr Met Val
370                 375                 380

Leu Tyr Glu Thr Val Asn Glu Met Ala Gly Glu Ala Glu Lys Ser Gln
385                 390                 395                 400

Gly Arg Asp Thr Leu Asn Tyr Ala Arg Asn Ala Leu Glu Ala Tyr Ile
                405                 410                 415

Asp Ala Ser Met Lys Glu Ala Lys Trp Ile Phe Ser Gly Phe Leu Pro
            420                 425                 430

Thr Phe Glu Glu Tyr Leu Asp Asn Gly Lys Val Ser Phe Gly Tyr Ser
        435                 440                 445

Ile Gly Thr Leu Gln Pro Ile Leu Thr Leu Gly Ile Pro Phe Pro His
450                 455                 460

His Ile Leu Gln Glu Ile Asp Phe Pro Ser Arg Leu Asn Asp Val Ala
465                 470                 475                 480

Cys Ser Ile Leu Arg Leu Lys Gly Asp Ile His Thr Tyr Glu Ala Glu
                485                 490                 495

Arg Ser Arg Gly Glu Lys Ser Ser Cys Ile Ser Cys Tyr Met Glu Glu
            500                 505                 510

Asn Pro Glu Ser Thr Glu Glu Asp Ala Ile Asn His Ile Asn Ser Met
        515                 520                 525

Val Asp Lys Leu Leu Lys Glu Leu Asn Trp Glu Tyr Leu Arg Pro Asp
530                 535                 540

Ser Asn Val Pro Ile Thr Ser Lys Lys His Ala Phe Asp Ile Leu Arg
545                 550                 555                 560

Ala Phe Tyr His Leu Tyr Lys Tyr Arg Asp Gly Phe Ser Val Ala Asn
                565                 570                 575

Tyr Glu Ile Lys Asn Leu Val Met Thr Thr Val Ile Glu Pro Val Pro
            580                 585                 590

Leu

<210> SEQ ID NO 26
<211> LENGTH: 564
<212> TYPE: PRT
<213> ORGANISM: P. pseudostrobus
<220> FEATURE:
<221> NAME/KEY: VARIANT
<222> LOCATION: (1)...(564)
<223> OTHER INFORMATION: Xaa = Any Amino Acid

<400> SEQUENCE: 26
```

```
Arg Arg Xaa Xaa Xaa His Ser Asn Leu Trp Asp Asn Phe Ile
  1               5                  10                  15

Gln Ser Leu Ser Thr Pro Tyr Gly Ala Ile Ser Tyr His Glu Ser Ala
             20                  25                  30

Gln Lys Leu Ile Gly Glu Val Lys Glu Met Ile Asn Ser Ile Ser Val
             35                  40                  45

Lys Asp Gly Glu Leu Ile Thr Pro Ser Asn Asp Leu Leu Met Arg Leu
 50                  55                  60

Ser Ile Val Asp Ser Ile Glu Arg Leu Gly Ile Asp Arg His Phe Lys
 65                  70                  75                  80

Ser Glu Ile Lys Ser Ala Leu Asp Tyr Val Tyr Ser Tyr Trp Asn Glu
                 85                  90                  95

Lys Gly Ile Gly Trp Gly Arg Asp Ser Val Val Ala Asp Leu Asn Ser
                100                 105                 110

Thr Ala Leu Gly Leu Arg Thr Leu Arg Leu His Gly Tyr Pro Val Ser
            115                 120                 125

Ser Asp Val Leu Gln His Phe Lys Glu Gln Lys Gly Gln Phe Ala Cys
130                 135                 140

Ser Ala Ile Gln Thr Glu Gly Glu Ile Arg Ser Val Leu Asn Leu Phe
145                 150                 155                 160

Arg Ala Ser Gln Ile Ala Phe Pro Gly Glu Lys Val Met Glu Glu Ala
                165                 170                 175

Glu Val Phe Ser Thr Ile Tyr Leu Lys Glu Ala Ile Leu Lys Leu Pro
                180                 185                 190

Val Cys Gly Leu Ser Arg Glu Ile Ser Tyr Val Leu Glu Tyr Gly Trp
                195                 200                 205

His Ile Asn Leu Pro Arg Leu Glu Ala Arg Asn Tyr Ile Asp Val Phe
210                 215                 220

Gly Gln Asp Pro Ile Tyr Leu Thr Pro Asn Met Lys Thr Gln Lys Leu
225                 230                 235                 240

Leu Glu Leu Ala Lys Leu Glu Phe Asn Met Phe His Ser Leu Gln Gln
                245                 250                 255

Gln Glu Leu Lys Leu Leu Ser Arg Trp Trp Lys Asp Ser Gly Phe Ser
                260                 265                 270

Gln Met Thr Phe Pro Arg His Arg His Val Glu Tyr Tyr Thr Leu Ala
            275                 280                 285

Ser Cys Ile Asp Ser Glu Pro Gln His Ser Ser Phe Arg Leu Gly Phe
290                 295                 300

Ala Lys Met Phe His Leu Ala Thr Val Leu Asp Asp Ile Tyr Asp Thr
305                 310                 315                 320

Phe Gly Thr Met Asp Glu Leu Glu Leu Phe Thr Ala Ala Val Lys Arg
                325                 330                 335

Trp His Pro Ser Ala Thr Glu Trp Leu Pro Glu Tyr Met Lys Gly Val
            340                 345                 350

Tyr Met Val Leu Tyr Glu Thr Val Asn Glu Met Ala Gly Glu Ala Glu
            355                 360                 365

Lys Ser Gln Gly Arg Asp Thr Leu Asn Tyr Ala Arg Asn Ala Leu Glu
370                 375                 380

Ala Tyr Ile Asp Ala Ser Met Lys Glu Ala Lys Trp Ile Phe Ser Gly
385                 390                 395                 400

Phe Leu Pro Thr Phe Glu Glu Tyr Leu Asp Asn Gly Lys Val Ser Phe
                405                 410                 415
```

```
Gly Tyr Ser Ile Gly Thr Leu Gln Pro Ile Leu Thr Leu Gly Ile Pro
            420                 425                 430

Phe Pro His His Ile Leu Gln Glu Ile Asp Phe Pro Ser Arg Leu Asn
        435                 440                 445

Asp Val Ala Cys Ser Ile Leu Arg Leu Lys Gly Asp Ile His Thr Tyr
    450                 455                 460

Glu Ala Glu Arg Ser Arg Gly Glu Lys Ser Ser Cys Ile Ser Cys Tyr
465                 470                 475                 480

Met Glu Glu Asn Pro Glu Ser Thr Glu Glu Asp Ala Ile Asn His Ile
                485                 490                 495

Asn Ser Met Val Asp Lys Leu Leu Lys Glu Leu Asn Trp Glu Tyr Leu
            500                 505                 510

Arg Pro Asp Ser Asn Val Pro Ile Thr Ser Lys Lys His Ala Phe Asp
        515                 520                 525

Ile Leu Arg Ala Phe Tyr His Leu Tyr Lys Tyr Arg Asp Gly Phe Ser
    530                 535                 540

Val Ala Asn Tyr Glu Ile Lys Asn Leu Val Met Thr Thr Val Ile Glu
545                 550                 555                 560

Pro Val Pro Leu

<210> SEQ ID NO 27
<211> LENGTH: 590
<212> TYPE: PRT
<213> ORGANISM: P. sabiniana

<400> SEQUENCE: 27

Ser Ser Lys Val Lys Val Val Arg Arg Thr Ile Ser Thr Ser Ile Arg
1               5                   10                  15

Met Cys Arg Ile Thr Thr Glu Ser Gly Glu Gly Val Gln Arg Arg Ile
            20                  25                  30

Ala Asn His His Ser Asn Leu Trp Asp Asp Asn Phe Ile Gln Ser Leu
        35                  40                  45

Ser Thr Pro Tyr Gly Ala Ile Ser Tyr His Glu Ser Ala Gln Lys Leu
    50                  55                  60

Ile Gly Glu Val Lys Glu Met Ile Asn Ser Ile Ser Val Lys Asp Gly
65                  70                  75                  80

Glu Leu Ile Thr Pro Ser Asn Asp Leu Leu Met Arg Leu Ser Ile Val
                85                  90                  95

Asp Ser Ile Glu Arg Leu Gly Ile Asp Arg His Phe Lys Ser Glu Ile
            100                 105                 110

Lys Ser Ala Leu Asp Tyr Val Tyr Ser Tyr Trp Asn Glu Lys Gly Ile
        115                 120                 125

Gly Trp Gly Arg Asp Ser Val Val Ala Asp Leu Asn Ser Thr Ala Leu
    130                 135                 140

Gly Leu Arg Thr Leu Arg Leu His Gly Tyr Pro Val Ser Ser Asp Val
145                 150                 155                 160

Leu Gln His Phe Lys Glu Gln Lys Gly Gln Phe Ala Cys Ser Ala Ile
                165                 170                 175

Gln Thr Glu Gly Glu Ile Arg Ser Val Leu Asn Leu Phe Arg Ala Ser
            180                 185                 190

Gln Ile Ala Phe Pro Gly Glu Lys Val Met Glu Glu Ala Glu Val Phe
        195                 200                 205

Ser Thr Ile Tyr Leu Lys Glu Ala Ile Leu Lys Leu Pro Val Cys Gly
    210                 215                 220
```

```
Leu Ser Arg Glu Ile Ser Tyr Val Leu Glu Tyr Gly Trp His Ile Asn
225                 230                 235                 240

Leu Pro Arg Leu Glu Ala Arg Asn Tyr Ile Asp Val Phe Gly Glu Asp
                245                 250                 255

Pro Ile Tyr Leu Thr Pro Asn Met Lys Thr Gln Lys Leu Leu Glu Leu
                260                 265                 270

Ala Lys Leu Glu Phe Asn Met Phe His Ser Leu Gln Gln Gln Glu Leu
            275                 280                 285

Lys Leu Leu Ser Arg Trp Trp Lys Asp Ser Gly Phe Ser Gln Met Thr
290                 295                 300

Phe Pro Arg His Arg His Val Glu Tyr Tyr Thr Leu Ala Ser Cys Ile
305                 310                 315                 320

Asp Ser Glu Pro Gln His Ser Ser Phe Arg Leu Gly Phe Ala Lys Ile
                325                 330                 335

Phe His Leu Ala Thr Val Leu Asp Asp Ile Tyr Asp Thr Phe Gly Thr
                340                 345                 350

Met Asp Glu Leu Glu Leu Phe Thr Ala Ala Val Lys Arg Trp His Pro
            355                 360                 365

Ser Ala Thr Glu Trp Leu Pro Glu Tyr Met Lys Gly Val Tyr Met Val
370                 375                 380

Leu Tyr Glu Thr Val Asn Glu Met Ala Gly Glu Ala Glu Lys Ser Gln
385                 390                 395                 400

Gly Arg Asp Thr Leu Asn Tyr Gly Arg Asn Ala Leu Glu Ala Tyr Ile
                405                 410                 415

Asp Ala Ser Met Glu Glu Ala Lys Trp Ile Phe Ser Gly Phe Leu Pro
                420                 425                 430

Thr Phe Glu Glu Tyr Leu Asp Asn Gly Lys Val Ser Phe Gly Tyr Gly
            435                 440                 445

Ile Gly Thr Leu Gln Pro Ile Leu Thr Leu Gly Ile Pro Phe Pro His
450                 455                 460

His Ile Leu Gln Glu Ile Asp Phe Pro Ser Arg Leu Asn Asp Val Ala
465                 470                 475                 480

Ser Ser Ile Leu Arg Leu Lys Gly Asp Ile His Thr Tyr Gln Ala Glu
                485                 490                 495

Arg Ser Arg Gly Glu Lys Ser Ser Cys Ile Ser Cys Tyr Met Glu Glu
                500                 505                 510

Asn Pro Glu Ser Thr Glu Glu Asp Ala Ile Asn His Ile Asn Ser Met
            515                 520                 525

Val Asp Lys Leu Leu Lys Glu Leu Asn Trp Glu Tyr Leu Arg Pro Asp
530                 535                 540

Ser Asn Val Pro Ile Thr Ser Lys Lys His Ala Phe Asp Ile Leu Arg
545                 550                 555                 560

Ala Phe Tyr His Leu Tyr Lys Tyr Arg Asp Gly Phe Ser Val Ala Asn
                565                 570                 575

Tyr Glu Ile Lys Asn Leu Val Met Thr Thr Val Ile Glu Pro
            580                 585                 590

<210> SEQ ID NO 28
<211> LENGTH: 593
<212> TYPE: PRT
<213> ORGANISM: P. sabiniana

<400> SEQUENCE: 28

Ser Ser Lys Val Lys Val Val Arg Thr Ile Ser Thr Ser Ile Arg
1               5                   10                  15
```

-continued

```
Met Cys Arg Ile Thr Thr Glu Ser Gly Glu Gly Val Gln Arg Ile
            20                  25                  30
Ala Asn His His Ser Asn Leu Trp Asp Asp Asn Phe Ile Gln Ser Leu
            35                  40                  45
Ser Thr Pro Tyr Gly Ala Ile Ser Tyr His Glu Ser Ala Gln Lys Leu
 50                  55                  60
Ile Gly Glu Val Lys Glu Met Ile Asn Ser Ile Ser Leu Lys Asp Gly
 65                  70                  75                  80
Glu Leu Ile Thr Pro Ser Asn Asp Leu Leu Met Arg Leu Ser Ile Val
                85                  90                  95
Asp Ser Ile Glu Arg Leu Gly Ile Asp Arg His Phe Lys Ser Glu Ile
                100                 105                 110
Lys Ser Ala Leu Asp Tyr Val Tyr Ser Tyr Trp Asn Glu Lys Gly Ile
                115                 120                 125
Gly Trp Gly Arg Asp Ser Val Val Ala Asp Leu Asn Ser Thr Ala Leu
 130                 135                 140
Gly Leu Arg Thr Leu Arg Leu His Gly Tyr Pro Val Ser Ser Asp Val
 145                 150                 155                 160
Leu Gln His Phe Lys Glu Gln Lys Gly Gln Phe Ala Cys Ser Ala Ile
                165                 170                 175
Gln Thr Glu Gly Glu Ile Arg Ser Val Leu Asn Leu Phe Arg Ala Ser
                180                 185                 190
Gln Ile Ala Phe Pro Gly Glu Lys Val Met Glu Glu Ala Glu Val Phe
                195                 200                 205
Ser Thr Ile Tyr Leu Lys Glu Ala Ile Leu Lys Leu Pro Val Cys Gly
                210                 215                 220
Leu Ser Arg Glu Ile Ser Tyr Val Leu Glu Tyr Gly Trp His Ile Asn
 225                 230                 235                 240
Leu Pro Arg Leu Glu Ala Arg Asn Tyr Ile Asp Val Phe Gly Glu Asp
                245                 250                 255
Pro Ile Tyr Leu Thr Pro Asn Met Lys Thr Gln Lys Leu Leu Glu Leu
                260                 265                 270
Ala Lys Leu Glu Phe Asn Met Phe His Ser Leu Gln Gln Gln Glu Leu
                275                 280                 285
Lys Leu Leu Ser Arg Trp Trp Lys Asp Ser Gly Phe Ser Gln Met Thr
                290                 295                 300
Phe Pro Arg His Arg Val Glu Tyr Tyr Thr Leu Ala Ser Cys Ile
 305                 310                 315                 320
Asp Ser Glu Pro Gln His Ser Ser Phe Arg Leu Gly Phe Ala Lys Ile
                325                 330                 335
Phe His Leu Ala Thr Val Leu Asp Asp Ile Tyr Asp Thr Phe Gly Thr
                340                 345                 350
Met Asp Glu Leu Glu Leu Phe Thr Ala Ala Val Lys Arg Trp His Pro
                355                 360                 365
Ser Ala Thr Glu Trp Leu Pro Glu Tyr Met Lys Gly Val Tyr Met Val
                370                 375                 380
Leu Tyr Glu Thr Val Asn Glu Met Ala Gly Glu Ala Glu Lys Ser Gln
 385                 390                 395                 400
Gly Arg Asp Thr Leu Asn Tyr Gly Arg Asn Ala Leu Glu Ala Tyr Ile
                405                 410                 415
Asp Ala Ser Met Glu Glu Ala Lys Trp Ile Phe Ser Gly Phe Leu Pro
                420                 425                 430
```

```
Thr Phe Glu Glu Tyr Leu Asp Asn Gly Lys Val Ser Phe Gly Tyr Gly
            435                 440                 445

Ile Gly Thr Leu Gln Pro Ile Leu Thr Leu Gly Ile Pro Phe Pro His
450                 455                 460

His Ile Leu Gln Glu Ile Asp Phe Pro Ser Arg Leu Asn Asp Val Ala
465                 470                 475                 480

Ser Ser Ile Leu Arg Leu Lys Gly Asp Ile His Thr Tyr Gln Ala Glu
            485                 490                 495

Arg Ser Arg Gly Glu Lys Ser Ser Cys Ile Ser Cys Tyr Met Glu Glu
            500                 505                 510

Asn Pro Glu Ser Thr Glu Glu Asp Ala Ile Asn His Ile Asn Ser Met
            515                 520                 525

Val Asp Lys Leu Leu Lys Glu Leu Asn Trp Glu Tyr Leu Arg Pro Asp
530                 535                 540

Ser Asn Val Pro Ile Thr Ser Lys Lys His Ala Phe Asp Ile Leu Arg
545                 550                 555                 560

Ala Phe Tyr His Leu Tyr Lys Tyr Arg Asp Gly Phe Ser Val Ala Asn
            565                 570                 575

Tyr Glu Ile Lys Asn Leu Val Met Thr Thr Val Ile Glu Pro Val Pro
            580                 585                 590

Leu

<210> SEQ ID NO 29
<211> LENGTH: 564
<212> TYPE: PRT
<213> ORGANISM: P. coulteri
<220> FEATURE:
<221> NAME/KEY: VARIANT
<222> LOCATION: (1)...(564)
<223> OTHER INFORMATION: Xaa = Any Amino Acid

<400> SEQUENCE: 29

Arg Arg Ile Ala Gly His His Ser Asn Leu Trp Asp Asp Asx Xaa Ile
1               5                   10                  15

Gln Ser Leu Ser Thr Pro Tyr Gly Ala Ile Ser Tyr His Glu Ser Ala
            20                  25                  30

Gln Lys Leu Ile Gly Glu Val Lys Glu Met Ile Asn Ser Ile Ser Val
        35                  40                  45

Lys Asp Gly Glu Leu Ile Thr Pro Ser Asn Asp Leu Leu Met Arg Leu
50                  55                  60

Ser Ile Val Asp Ser Ile Glu Arg Leu Gly Ile Asp Arg His Phe Lys
65                  70                  75                  80

Ser Glu Ile Lys Ser Ala Leu Asp Tyr Val Tyr Ser Tyr Trp Asn Glu
            85                  90                  95

Lys Gly Ile Gly Trp Gly Arg Asp Ser Val Val Ala Asp Leu Asn Ser
            100                 105                 110

Thr Ala Leu Gly Leu Arg Thr Leu Arg Leu His Gly Tyr Pro Val Ser
        115                 120                 125

Ser Asp Val Leu Gln His Phe Lys Glu Gln Lys Gly Gln Phe Ala Cys
130                 135                 140

Ser Ala Ile Gln Thr Glu Gly Glu Ile Arg Ser Val Leu Asn Leu Phe
145                 150                 155                 160

Arg Ala Ser Gln Ile Ala Phe Pro Gly Glu Lys Val Met Glu Glu Ala
            165                 170                 175

Glu Val Phe Ser Thr Ile Tyr Leu Lys Glu Ala Ile Leu Lys Leu Pro
            180                 185                 190
```

```
Val Cys Gly Leu Ser Arg Glu Ile Ser Tyr Val Leu Glu Tyr Gly Trp
        195                 200                 205

His Ile Asn Leu Pro Arg Leu Glu Ala Arg Asn Tyr Ile Asp Val Phe
    210                 215                 220

Gly Glu Asp Pro Ile Tyr Leu Thr Pro Asn Met Lys Thr Gln Lys Leu
225                 230                 235                 240

Leu Glu Leu Ala Lys Leu Glu Phe Asn Met Phe His Ser Leu Gln Gln
                245                 250                 255

Gln Glu Leu Lys Leu Leu Ser Arg Trp Trp Lys Asp Ser Gly Phe Ser
            260                 265                 270

Gln Met Thr Phe Pro Arg His Arg His Val Glu Tyr Tyr Thr Leu Ala
                275                 280                 285

Ser Cys Ile Asp Ser Glu Pro Gln His Ser Ser Phe Arg Leu Gly Phe
        290                 295                 300

Ala Lys Ile Phe His Leu Ala Thr Val Leu Asp Asp Ile Tyr Asp Thr
305                 310                 315                 320

Phe Gly Thr Met Asp Glu Leu Glu Leu Phe Thr Ala Ala Val Lys Arg
                325                 330                 335

Trp His Pro Ser Ala Thr Glu Trp Leu Pro Glu Tyr Met Lys Gly Val
            340                 345                 350

Tyr Met Val Leu Tyr Glu Thr Val Asn Glu Met Ala Gly Glu Ala Glu
                355                 360                 365

Lys Ser Gln Gly Arg Asp Thr Leu Asn Tyr Gly Arg Asn Ala Leu Glu
        370                 375                 380

Ala Tyr Ile Asp Ala Ser Met Glu Glu Ala Lys Trp Ile Phe Ser Gly
385                 390                 395                 400

Phe Leu Pro Thr Phe Glu Glu Tyr Leu Asp Asn Gly Lys Val Ser Phe
                405                 410                 415

Gly Tyr Gly Ile Gly Thr Leu Gln Pro Ile Leu Thr Leu Gly Ile Pro
            420                 425                 430

Phe Pro His His Ile Leu Gln Glu Ile Asp Phe Pro Ser Arg Leu Asn
                435                 440                 445

Asp Val Ala Ser Ser Ile Leu Arg Leu Lys Gly Asp Ile His Thr Tyr
450                 455                 460

Gln Ala Glu Arg Ser Arg Gly Glu Lys Ser Ser Cys Ile Ser Cys Tyr
465                 470                 475                 480

Met Glu Glu Asn Pro Glu Ser Thr Glu Glu Asp Ala Ile Asn His Ile
                485                 490                 495

Asn Ser Met Val Asp Lys Leu Leu Lys Glu Leu Asn Trp Glu Tyr Leu
            500                 505                 510

Arg Pro Asp Ser Asn Val Pro Ile Thr Ser Lys Lys His Ala Phe Asp
                515                 520                 525

Ile Leu Arg Ala Phe Tyr His Leu Tyr Lys Tyr Arg Asp Gly Phe Ser
            530                 535                 540

Val Ala Asn Tyr Glu Ile Lys Asn Leu Val Met Thr Thr Val Ile Glu
545                 550                 555                 560

Pro Val Pro Leu

<210> SEQ ID NO 30
<211> LENGTH: 556
<212> TYPE: PRT
<213> ORGANISM: P. torreyana

<400> SEQUENCE: 30
```

```
Asn Leu Trp Asp Asp Leu Ile Gln Ser Leu Ser Thr Pro Tyr Gly
 1               5                  10                 15

Ala Ile Ser Tyr His Glu Ser Ala Gln Lys Leu Ile Gly Glu Val Lys
                20                  25                  30

Glu Met Ile Asn Ser Ile Ser Val Lys Asp Gly Glu Leu Ile Thr Pro
            35                  40                  45

Ser Asn Asp Leu Leu Met Arg Leu Ser Ile Val Asp Ser Ile Glu Arg
 50                  55                  60

Leu Gly Ile Asp Arg His Phe Lys Ser Glu Ile Lys Ser Ala Leu Asp
 65                  70                  75                  80

Tyr Val Tyr Ser Tyr Trp Asn Glu Lys Gly Ile Gly Trp Gly Arg Asp
                85                  90                  95

Ser Val Val Ala Asp Leu Asn Ser Thr Ala Leu Gly Leu Arg Thr Leu
                100                 105                 110

Arg Leu His Gly Tyr Pro Val Ser Ser Asp Val Leu Gln His Phe Lys
            115                 120                 125

Glu Gln Lys Gly Gln Phe Ala Cys Ser Ala Ile Gln Thr Glu Gly Glu
            130                 135                 140

Ile Arg Ser Val Leu Asn Leu Phe Arg Ala Ser Gln Ile Ala Phe Pro
145                 150                 155                 160

Gly Glu Lys Val Met Glu Glu Ala Glu Val Phe Ser Thr Met Tyr Leu
                165                 170                 175

Lys Glu Ala Ile Leu Lys Leu Pro Val Cys Gly Leu Ser Arg Glu Ile
            180                 185                 190

Ser Tyr Val Leu Glu Tyr Gly Trp His Ile Asn Leu Pro Arg Leu Glu
            195                 200                 205

Ala Arg Asn Tyr Ile Asp Val Phe Gly Gln Asp Pro Ile Tyr Leu Thr
210                 215                 220

Pro Asn Met Lys Thr Gln Lys Leu Leu Glu Leu Ala Lys Leu Glu Phe
225                 230                 235                 240

Asn Met Phe His Ser Leu Gln Gln Gln Glu Leu Lys Leu Leu Ser Arg
                245                 250                 255

Trp Trp Lys Asp Ser Gly Phe Ser Gln Met Thr Phe Pro Arg His Arg
            260                 265                 270

His Val Glu Tyr Tyr Thr Leu Ala Ser Cys Ile Asp Ser Glu Pro Gln
            275                 280                 285

His Ser Ser Phe Arg Leu Gly Phe Ala Lys Ile Phe His Leu Ala Thr
            290                 295                 300

Val Leu Asp Asp Ile Tyr Asp Thr Phe Gly Thr Met Asp Glu Leu Glu
305                 310                 315                 320

Leu Phe Thr Ala Ala Val Lys Arg Trp His Pro Ser Ala Thr Glu Trp
                325                 330                 335

Leu Pro Glu Tyr Met Lys Gly Val Tyr Met Val Leu Tyr Glu Thr Val
            340                 345                 350

Asn Glu Met Ala Gly Glu Ala Glu Lys Ser Gln Gly Arg Asp Thr Leu
            355                 360                 365

Asn Tyr Ala Arg Asn Ala Leu Glu Ala Tyr Ile Asp Ala Ser Met Glu
            370                 375                 380

Glu Ala Lys Trp Ile Phe Ser Gly Phe Leu Pro Thr Phe Glu Glu Tyr
385                 390                 395                 400

Leu Asp Asn Gly Lys Val Ser Phe Gly Tyr Gly Ile Gly Thr Leu Gln
                405                 410                 415
```

```
Pro Ile Leu Thr Leu Gly Ile Pro Phe Pro His His Ile Leu Gln Glu
            420                 425                 430

Ile Asp Phe Pro Ser Arg Leu Asn Asp Val Ala Ser Ser Ile Leu Arg
            435                 440                 445

Leu Lys Gly Asp Ile His Thr Tyr Gln Ala Glu Arg Ser Arg Gly Glu
            450                 455                 460

Lys Ser Ser Cys Ile Ser Cys Tyr Met Glu Glu Asn Pro Glu Ser Thr
465                 470                 475                 480

Glu Glu Asp Ala Ile Asn His Ile Asn Ser Met Val Asp Lys Leu Leu
                485                 490                 495

Lys Glu Leu Asn Trp Glu Tyr Leu Arg Pro Asp Ser Asn Val Pro Ile
            500                 505                 510

Thr Ser Lys Lys His Ala Phe Asp Ile Leu Arg Ala Phe Tyr His Leu
            515                 520                 525

Tyr Lys Tyr Arg Asp Gly Phe Ser Val Ala Asn Tyr Glu Ile Lys Asn
            530                 535                 540

Leu Val Met Thr Thr Val Ile Glu Pro Val Pro Leu
545                 550                 555
```

<210> SEQ ID NO 31
<211> LENGTH: 564
<212> TYPE: PRT
<213> ORGANISM: P. attenuata

<400> SEQUENCE: 31

```
Arg Arg Arg Gly Asp Phe His Ser Asn Leu Trp Asp Asp Asn Phe Ile
1               5                   10                  15

Gln Ser Leu Ser Thr Pro Tyr Gly Ala Ile Ser Tyr His Glu Ser Ala
            20                  25                  30

Gln Lys Leu Ile Gly Glu Val Lys Glu Met Ile Asn Ser Ile Ser Asp
            35                  40                  45

Lys Asp Gly Glu Leu Ile Thr Pro Ser Asn Asp Leu Leu Met Leu Leu
50                  55                  60

Ser Ile Val Asp Ser Ile Glu Arg Leu Gly Ile Asp Arg His Phe Lys
65                  70                  75                  80

Ser Glu Ile Lys Ser Ala Leu Asp Tyr Val Tyr Ser Tyr Trp Asn Glu
                85                  90                  95

Lys Gly Ile Gly Trp Gly Arg Asp Ser Val Val Ala Asp Leu Asn Ser
            100                 105                 110

Thr Ala Leu Gly Leu Arg Thr Leu Arg Leu His Gly Tyr Pro Val Ser
            115                 120                 125

Ser Asp Val Leu Gln His Phe Lys Glu Gln Asn Gly Gln Phe Ala Cys
            130                 135                 140

Ser Ala Ile Gln Thr Glu Gly Glu Ile Arg Ser Val Leu Asn Leu Phe
145                 150                 155                 160

Arg Ala Ser Gln Ile Ala Phe Pro Gly Glu Lys Val Met Glu Glu Ala
                165                 170                 175

Glu Val Phe Ser Thr Lys Tyr Leu Lys Glu Ala Ile Leu Lys Leu Pro
            180                 185                 190

Val Cys Gly Leu Ser Arg Glu Ile Ser Tyr Val Leu Glu Tyr Gly Trp
            195                 200                 205

His Met Asn Leu Pro Arg Leu Glu Ala Arg Asn Tyr Ile Asp Val Phe
    210                 215                 220

Gly Gln Asp Pro Ile Tyr Leu Thr Pro Asn Met Lys Thr Gln Lys Leu
225                 230                 235                 240
```

Leu Glu Leu Ala Lys Leu Glu Phe Asn Met Phe His Ser Leu Gln Gln
            245                 250                 255

Gln Glu Leu Lys Leu Leu Ser Arg Trp Trp Lys Asp Ser Gly Phe Ser
        260                 265                 270

Gln Met Thr Phe Pro Arg His Arg His Val Glu Tyr Tyr Thr Leu Ala
    275                 280                 285

Ser Cys Ile Asp Ser Glu Pro Gln His Ser Ser Phe Arg Leu Gly Phe
290                 295                 300

Ala Lys Ile Phe His Leu Ala Thr Val Leu Asp Asp Ile Tyr Asp Thr
305                 310                 315                 320

Phe Gly Thr Met Asp Glu Leu Glu Leu Phe Thr Ala Ala Val Lys Arg
            325                 330                 335

Trp His Pro Ser Ala Thr Glu Trp Leu Pro Glu Tyr Met Lys Gly Val
        340                 345                 350

Tyr Met Val Leu Tyr Glu Thr Val Asn Glu Met Ala Gly Glu Ala Glu
    355                 360                 365

Lys Ser Gln Gly Arg Asp Thr Leu Asn Tyr Ala Arg Asn Ala Leu Glu
370                 375                 380

Ala Tyr Ile Asp Ala Ser Met Glu Glu Ala Lys Trp Ile Phe Ser Gly
385                 390                 395                 400

Phe Leu Pro Thr Phe Glu Glu Tyr Leu Asp Asn Gly Lys Val Ser Phe
            405                 410                 415

Gly Tyr Thr Ile Gly Thr Leu Gln Pro Ile Leu Thr Leu Gly Ile Pro
        420                 425                 430

Phe Pro His His Ile Leu Gln Glu Ile Asp Phe Pro Ser Arg Leu Asn
    435                 440                 445

Asp Val Ala Cys Ser Ile Leu Arg Leu Lys Gly Asp Val His Thr Tyr
450                 455                 460

Gln Pro Glu Arg Ser Arg Gly Glu Glu Ser Ser Cys Ile Ser Cys Tyr
465                 470                 475                 480

Ile Glu Glu Asn Pro Glu Ser Thr Glu Glu Asp Ala Ile Asn His Ile
            485                 490                 495

Asn Ser Met Val Asp Lys Leu Leu Lys Glu Leu Asn Trp Glu Tyr Leu
        500                 505                 510

Arg Pro Asp Ser Asn Val Pro Ile Thr Ser Lys Lys His Ala Phe Asp
    515                 520                 525

Ile Leu Arg Ala Leu Tyr His Leu Tyr Lys Tyr Arg Asp Gly Tyr Ser
530                 535                 540

Val Ala Asn Tyr Glu Ile Lys Asn Leu Val Met Thr Thr Val Ile Glu
545                 550                 555                 560

Pro Val Pro Leu

<210> SEQ ID NO 32
<211> LENGTH: 556
<212> TYPE: PRT
<213> ORGANISM: P. radiata

<400> SEQUENCE: 32

Asn Leu Trp Asp Asp Leu Ile Gln Ser Leu Ser Thr Pro Tyr Gly
  1               5                  10                  15

Ala Ile Ser Tyr His Glu Ser Ala Gln Lys Leu Ile Gly Glu Val Lys
            20                  25                  30

Glu Met Ile Asn Ser Ile Ser Asp Lys Asn Gly Glu Leu Ile Thr Pro
        35                  40                  45

```
Ser Asn Asp Leu Leu Met Arg Leu Ser Ile Val Asp Ser Ile Glu Arg
 50                  55                  60
Leu Gly Ile Asp Arg His Phe Lys Ser Glu Ile Lys Ser Ala Leu Asp
 65                  70                  75                  80
Tyr Val Tyr Ser Tyr Trp Asn Glu Lys Gly Ile Gly Trp Gly Arg Asp
                 85                  90                  95
Ser Val Val Ala Asp Leu Asn Ser Thr Ala Leu Gly Leu Arg Thr Leu
                100                 105                 110
Arg Leu His Gly Tyr Pro Val Ser Ser Asp Val Leu Gln His Phe Lys
                115                 120                 125
Glu Gln Asn Gly Gln Phe Ala Cys Ser Ala Ile Gln Thr Glu Gly Glu
            130                 135                 140
Ile Arg Ser Val Leu Asn Leu Phe Arg Ala Ser Gln Ile Ala Phe Pro
145                 150                 155                 160
Gly Glu Lys Val Met Glu Ala Glu Val Phe Ser Thr Lys Tyr Leu
                165                 170                 175
Lys Glu Ala Ile Leu Lys Leu Pro Val Cys Gly Leu Ser Arg Glu Ile
                180                 185                 190
Ser Tyr Val Leu Glu Tyr Gly Trp His Met Asn Leu Pro Arg Leu Glu
                195                 200                 205
Ala Arg Asn Tyr Ile Asp Val Phe Gly Gln Asp Pro Ile Tyr Leu Thr
            210                 215                 220
Pro Asn Met Lys Thr Gln Lys Leu Leu Glu Leu Ala Lys Leu Glu Phe
225                 230                 235                 240
Asn Met Phe His Ser Leu Gln Gln Gln Glu Leu Lys Leu Leu Ser Arg
                245                 250                 255
Trp Trp Lys Asp Ser Gly Phe Ser Gln Met Thr Phe Pro Arg His Arg
                260                 265                 270
His Val Glu Tyr Tyr Thr Leu Ala Ser Cys Ile Asp Ser Glu Pro Gln
            275                 280                 285
His Ser Ser Phe Arg Leu Gly Phe Ala Lys Ile Phe His Leu Ala Thr
            290                 295                 300
Val Leu Asp Asp Ile Tyr Asp Thr Phe Gly Thr Met Asp Glu Leu Glu
305                 310                 315                 320
Leu Phe Thr Ala Ala Val Lys Arg Trp His Pro Ser Ala Thr Glu Trp
                325                 330                 335
Leu Pro Glu Tyr Met Lys Gly Val Tyr Met Val Leu Tyr Glu Thr Val
                340                 345                 350
Asn Glu Met Ala Gly Glu Ala Glu Lys Ser Gln Gly Arg Asp Thr Leu
            355                 360                 365
Asn Tyr Ala Arg Asn Ala Leu Glu Ala Tyr Ile Asp Ala Ser Met Glu
            370                 375                 380
Glu Ala Lys Trp Ile Phe Ser Gly Phe Leu Pro Thr Phe Glu Glu Tyr
385                 390                 395                 400
Leu Asp Asn Gly Lys Val Ser Phe Gly Tyr Thr Ile Gly Thr Leu Gln
                405                 410                 415
Pro Ile Leu Thr Leu Gly Ile Pro Phe Pro His His Ile Leu Gln Glu
                420                 425                 430
Ile Asp Phe Pro Ser Arg Leu Asn Asp Val Ala Cys Ser Ile Leu Arg
            435                 440                 445
Leu Lys Gly Asp Val His Thr Tyr Gln Pro Glu Arg Ser Arg Gly Glu
    450                 455                 460
```

```
Glu Ser Ser Cys Ile Ser Cys Tyr Met Glu Glu Asn Pro Glu Ser Thr
465                 470                 475                 480

Glu Glu Asp Ala Ile Asn His Ile Asn Ser Met Val Asp Lys Leu Leu
                485                 490                 495

Lys Glu Leu Asn Trp Glu Tyr Leu Arg Pro Asp Ser Asn Val Pro Ile
            500                 505                 510

Thr Ser Lys Lys His Ala Phe Asp Ile Leu Arg Ala Leu Tyr His Leu
        515                 520                 525

Tyr Lys Tyr Arg Asp Gly Tyr Ser Val Ala Asn Tyr Glu Ile Lys Asn
530                 535                 540

Leu Val Met Thr Thr Val Ile Glu Pro Val Pro Leu
545                 550                 555

<210> SEQ ID NO 33
<211> LENGTH: 593
<212> TYPE: PRT
<213> ORGANISM: P. contorta

<400> SEQUENCE: 33

Ser Ser Lys Val Lys Val Val Arg Arg Thr Met Ser Thr Ser Ile Arg
1               5                   10                  15

Met Cys Gln Ile Thr Thr Val Ser Gly Glu Gly Val Gln Arg Arg Ile
                20                  25                  30

Ala Asn His His Ser Asn Leu Trp Asp Asp Asn Phe Ile Gln Ser Leu
            35                  40                  45

Ser Thr Pro Tyr Gly Ala Ile Ser Tyr His Glu Ser Ala Gln Lys Leu
        50                  55                  60

Ile Gly Glu Val Lys Glu Met Ile Asn Ser Ile Ser Val Lys Asp Gly
65                  70                  75                  80

Glu Leu Ile Thr Pro Ser Asn Asp Leu Leu Met Arg Leu Ser Ile Val
                85                  90                  95

Asp Ser Ile Glu Arg Leu Gly Ile Asp Arg His Phe Lys Ser Glu Ile
            100                 105                 110

Lys Ser Ala Leu Asp Tyr Val Tyr Ser Tyr Trp Asn Glu Lys Gly Ile
        115                 120                 125

Gly Trp Gly Arg Asp Ser Val Val Ala Asp Leu Asn Ser Thr Ala Leu
130                 135                 140

Gly Leu Arg Thr Leu Arg Leu His Gly Tyr Pro Val Ser Ser Asp Val
145                 150                 155                 160

Leu Gln His Phe Lys Glu Gln Lys Gly Gln Phe Ala Cys Ser Ala Ile
                165                 170                 175

Gln Thr Glu Gly Glu Ile Arg Ser Val Leu Asn Leu Phe Arg Ala Ser
            180                 185                 190

Gln Ile Ala Phe Pro Gly Glu Lys Val Met Glu Glu Ala Glu Val Phe
        195                 200                 205

Ser Thr Lys Tyr Leu Lys Glu Ala Ile Leu Lys Leu Pro Val Cys Gly
210                 215                 220

Leu Ser Arg Glu Ile Ser Tyr Val Leu Glu Tyr Gly Trp His Met Asn
225                 230                 235                 240

Leu Pro Arg Leu Glu Ala Arg Asn Tyr Ile Asp Val Phe Gly Gln Asp
                245                 250                 255

Pro Ile Tyr Leu Thr Pro Asn Met Lys Thr Gln Lys Leu Leu Glu Leu
            260                 265                 270

Ala Lys Leu Glu Phe Asn Met Phe His Ser Leu Gln Gln Gln Glu Leu
        275                 280                 285
```

Lys Leu Leu Ser Arg Trp Trp Lys Asp Ser Gly Phe Ser Gln Met Thr
            290                 295                 300

Phe Pro Arg His Arg His Val Glu Tyr Tyr Thr Leu Ala Ser Cys Ile
305                 310                 315                 320

Asp Ser Glu Pro Gln His Ser Ser Phe Arg Leu Gly Phe Ala Lys Ile
            325                 330                 335

Phe His Leu Ala Thr Val Leu Asp Asp Ile Tyr Asp Thr Phe Gly Thr
            340                 345                 350

Met Asp Glu Leu Glu Leu Phe Thr Ala Ala Val Lys Arg Trp His Pro
            355                 360                 365

Ser Ala Thr Glu Trp Leu Pro Glu Tyr Met Lys Gly Val Tyr Met Val
370                 375                 380

Leu Tyr Glu Thr Val Asn Glu Met Ala Gly Glu Ala Glu Lys Ser Gln
385                 390                 395                 400

Gly Arg Asp Thr Leu Asn Tyr Ala Arg Asn Ala Leu Glu Ala Tyr Ile
            405                 410                 415

Asp Ala Ser Met Glu Glu Ala Lys Trp Ile Phe Ser Gly Phe Leu Pro
            420                 425                 430

Thr Phe Glu Glu Tyr Leu Asp Asn Gly Lys Val Ser Phe Gly Tyr Thr
            435                 440                 445

Ile Gly Thr Leu Gln Pro Ile Leu Thr Leu Gly Ile Pro Phe Pro His
450                 455                 460

His Ile Leu Gln Glu Ile Asp Phe Pro Ser Arg Leu Asn Asp Val Ala
465                 470                 475                 480

Cys Ser Ile Leu Arg Leu Lys Gly Asp Ile His Thr Tyr Gln Pro Glu
            485                 490                 495

Arg Ser Arg Gly Glu Glu Ser Cys Ile Ser Cys Tyr Met Glu Asp
            500                 505                 510

Asn Pro Glu Ser Thr Glu Glu Asp Ala Ile Asn His Ile Asn Ser Met
            515                 520                 525

Val Asp Lys Leu Leu Lys Glu Leu Asn Trp Glu Tyr Leu Arg Pro Asp
530                 535                 540

Ser Asn Val Pro Ile Thr Ser Lys Lys His Ala Phe Asp Ile Leu Arg
545                 550                 555                 560

Ala Phe Tyr His Leu Tyr Lys Tyr Arg Asp Gly Tyr Ser Val Ala Asn
            565                 570                 575

Tyr Glu Ile Lys Asn Leu Val Met Thr Thr Val Ile Glu Pro Val Pro
            580                 585                 590

Leu

<210> SEQ ID NO 34
<211> LENGTH: 593
<212> TYPE: PRT
<213> ORGANISM: P. contorta

<400> SEQUENCE: 34

Ser Ser Lys Val Lys Val Val Arg Arg Thr Met Ser Thr Ser Ile Arg
1               5                   10                  15

Met Cys Gln Ile Thr Thr Val Ser Gly Glu Gly Val Gln Arg Arg Ile
            20                  25                  30

Ala Asn His His Ser Asn Leu Trp Asp Asp Asn Phe Ile Gln Ser Leu
        35                  40                  45

Ser Thr Pro Tyr Gly Ala Ile Ser Tyr His Glu Ser Ala Gln Lys Leu
    50                  55                  60

-continued

```
Ile Gly Glu Val Lys Glu Met Ile Asn Ser Ile Ser Val Lys Asp Gly
 65                  70                  75                  80

Glu Leu Ile Thr Pro Ser Asn Asp Leu Leu Met Arg Leu Ser Ile Val
             85                  90                  95

Asp Ser Ile Glu Arg Leu Gly Ile Asp Arg His Phe Lys Ser Glu Ile
            100                 105                 110

Lys Ser Ala Leu Asp Tyr Val Tyr Ser Tyr Trp Asn Glu Lys Gly Ile
            115                 120                 125

Gly Trp Gly Arg Asp Ser Val Ala Asp Leu Asn Ser Thr Ala Leu
130                 135                 140

Gly Leu Arg Thr Leu Arg Leu His Gly Tyr Pro Val Ser Ser Asp Val
145                 150                 155                 160

Leu Gln His Phe Lys Glu Gln Lys Gly Gln Phe Ala Cys Ser Ala Ile
                165                 170                 175

Gln Thr Glu Gly Glu Ile Arg Ser Val Leu Asn Leu Phe Arg Ala Ser
            180                 185                 190

Gln Ile Ala Phe Pro Gly Glu Lys Val Met Glu Glu Ala Glu Val Phe
            195                 200                 205

Ser Thr Lys Tyr Leu Lys Glu Ala Ile Leu Lys Leu Pro Val Cys Gly
            210                 215                 220

Leu Ser Arg Glu Ile Ser Tyr Val Leu Glu Tyr Gly Trp His Ile Asn
225                 230                 235                 240

Leu Pro Arg Leu Glu Ala Arg Asn Tyr Ile Asp Val Phe Gly Gln Asp
                245                 250                 255

Pro Ile Tyr Leu Thr Pro Asn Met Lys Thr Gln Lys Leu Leu Glu Leu
            260                 265                 270

Ala Lys Leu Glu Phe Asn Met Phe His Ser Leu Gln Gln Gln Glu Leu
            275                 280                 285

Lys Leu Leu Ser Arg Trp Trp Lys Asp Ser Gly Phe Ser Gln Met Thr
290                 295                 300

Phe Pro Arg His Arg His Val Glu Tyr Tyr Thr Leu Ala Ser Cys Ile
305                 310                 315                 320

Asp Ser Glu Pro Gln His Ser Ser Phe Arg Leu Gly Phe Ala Lys Ile
                325                 330                 335

Phe His Leu Ala Thr Val Leu Asp Asp Ile Tyr Asp Thr Phe Gly Thr
            340                 345                 350

Met Asp Glu Leu Glu Leu Phe Thr Ala Ala Val Lys Arg Trp His Pro
            355                 360                 365

Ser Ala Thr Glu Trp Leu Pro Glu Tyr Met Lys Gly Val Tyr Met Val
370                 375                 380

Leu Tyr Glu Thr Val Asn Glu Met Ala Gly Glu Ala Glu Lys Ser Gln
385                 390                 395                 400

Gly Arg Asp Thr Leu Asn Tyr Ala Arg Asn Ala Leu Glu Ala Tyr Ile
                405                 410                 415

Asp Ala Ser Met Glu Glu Ala Lys Trp Ile Phe Ser Gly Phe Leu Pro
            420                 425                 430

Thr Phe Glu Glu Tyr Leu Asp Asn Gly Lys Val Ser Phe Gly Tyr Thr
            435                 440                 445

Ile Gly Thr Leu Gln Pro Ile Leu Thr Leu Gly Ile Pro Phe Pro His
            450                 455                 460

His Ile Leu Gln Glu Ile Asp Phe Pro Ser Arg Leu Asn Asp Val Ala
465                 470                 475                 480
```

-continued

```
Cys Ser Ile Leu Arg Leu Lys Gly Asp Val His Thr Tyr Gln Ala Glu
            485             490                 495

Arg Ser Arg Gly Glu Glu Ser Ser Cys Ile Ser Cys Tyr Met Glu Asp
            500             505             510

Asn Pro Glu Ser Thr Glu Glu Asp Ala Ile Asn His Ile Asn Ser Met
            515             520             525

Val Asp Lys Leu Leu Lys Glu Leu Asn Trp Glu Tyr Leu Arg Pro Asp
    530             535             540

Ser Asn Val Pro Ile Thr Ser Lys Lys His Ala Phe Asp Ile Leu Arg
545             550             555                 560

Ala Phe Tyr His Leu Tyr Lys Tyr Arg Asp Gly Tyr Ser Val Ala Asn
            565             570             575

Tyr Glu Ile Lys Asn Leu Val Met Thr Thr Val Ile Glu Pro Val Pro
            580             585             590

Leu
```

METHYL BUTENOL SYNTHASE

RELATED APPLICATION

This application is a divisional of and claims the benefit of priority under 35 U.S.C. §120 to U.S. patent application Ser. No. 13/321,458, filed on Mar. 5, 2012, which is a U.S. National Stage Filing under 35 U.S.C. 371 from International Application No. PCT/US2010/035820, filed May 21, 2010 and published in English as WO 2010/135674 on Nov. 25, 2010, and claims priority from U.S. Provisional Application Ser. No. 61/180,757 filed May 22, 2009, which applications are herein incorporated by reference in their entireties.

STATEMENT OF GOVERNMENT RIGHTS

This invention was made with government support under Grant number IOS0830225 awarded by the National Science Foundation. The government has certain rights in the invention.

BACKGROUND OF THE INVENTION

In 2007, there were 1.8 million alternative fuel vehicles sold in the United States, indicating an increasing popularity of alternative fuels. There is growing perceived economic and political need for the development of alternative fuel sources due to general environmental, economic, and geopolitical concerns of sustainability.

The major environmental concern is that most of the observed increase in globally averaged temperatures since the mid-20th century is due to the observed increase in greenhouse gas concentrations. Since burning fossil fuels is known to increase greenhouse gas concentrations in the atmosphere, it is believed that they are a likely contributor to global warming.

Although fossil fuels have become the dominant energy resource for the modern world, alcohol has been used as a fuel throughout history. The first four aliphatic alcohols (methanol, ethanol, propanol, and butanol) are of interest as fuels because they can be synthesized and they have characteristics which allow them to be used in current engines. Biobutanol has an energy density that is closer to gasoline than the other alcohols; however, this advantage is outweighed by disadvantages (compared to ethanol and methanol) concerning, for example, production.

SUMMARY OF THE INVENTION

The present invention provides for the first time genes encoding methyl butenol (MBO) synthase and its use in methyl butenol production. Thus, one embodiment provides an isolated and purified methyl butenol (MBO) synthase nucleic acid molecule, wherein the MBO synthase nucleic acid molecule comprises any one of SEQ ID NOs:1-17 or a nucleic acid molecule having at least about 80% sequence identity thereof.

Another embodiment provides an expression vector comprising a MBO synthase nucleic acid molecule. One embodiment provides a prokaryotic or eukaryotic host cell transformed with a MBO synthase nucleic acid molecule (e.g., in an expression vector). In one embodiment the transformed host cells express the exogenous MBO synthase (mRNA or protein). In one embodiment, the host cells express MBO synthase and yield MBO.

One embodiment provides an isolated and purified methyl butenol (MBO) synthase polypeptide, wherein the MBO synthase polypeptide comprises any one of SEQ ID NOs:18-34 or a bioactive polypeptide having at least about 80% sequence identity thereof.

Another embodiment provides a method to produce methyl butenol comprising transforming a host cell with a nucleic acid molecule coding for a methyl butenol synthase and expressing said molecule in a host cell so as to yield methyl butenol. In one embodiment, the hose cells are fermentative organisms, such as a bacteria, cyanobacteria or yeast (e.g., a bacteria or yeast that can break down sugar into alcohol) or eukaryotic micro algae. In one embodiment the fermentative organism is *Saccharomyces cerevisiae, Klebsiella oxytoca, Synechococcus* sp., *Synechocystis* sp., *Anabaena* sp., *Chlorella* sp. *Scenedesmus* sp., *Bracteococcus* sp. *Chlamydomonus* sp., C5- or C6-fermentative organisms (including *Zymomonas* (e.g., *Zymomonas mobilis*)) or a combination thereof. In one embodiment, the transformed host cell is used in fermentation with a carbohydrate to yield MBO (similar to bioethanol production).

In one embodiment, the MBO synthase (in a purified or unpurified form) is used in combination with a carbohydrate to yield MBO. In one embodiment, the fermentative organism is bacteria, cyanobacteria or yeast (e.g., a bacteria or yeast that can break down sugar into alcohol) or eukaryotic micro algae. In one embodiment the fermentative organism is *Saccharomyces cerevisiae, Klebsiella oxytoca, Synechococcus* sp., *Synechocystis* sp., *Anabaena* sp., *Chlorella* sp. *Scenedesmus* sp., *Bracteococcus* sp. *Chlamydomonus* sp., C5- or C6-fermentative organisms (including *Zymomonas* (e.g., *Zymomonas mobilis*)) or combinations thereof.

BRIEF DESCRIPTION OF THE DRAWINGS

FIGS. 1A-M provide nucleic acid molecules coding for a methyl butenol synthase (SEQ ID NOs:1-17).

FIGS. 2A-E provide the sequence of several methyl butenol synthases. (SEQ ID NO:18-34).

DETAILED DESCRIPTION OF THE INVENTION

Figure 3A:
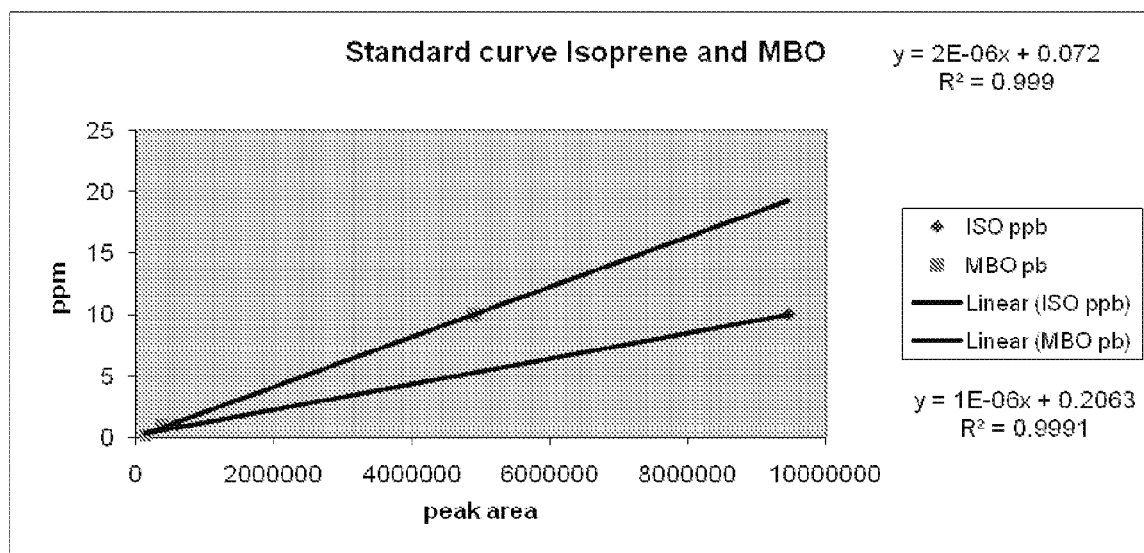
FIGS. 3A-B demonstrate the methylbutenol and isoprene production from soluble and insoluble extract fractions.

The present invention provides for the first time genes encoding methyl butenol (MBO) synthase and its use in methyl butenol production. In particular, the methyl butenol synthase gene was isolated from several species of pine. The gene is useful for the enzymatic production of methyl butenol, which can be used as an alternative fuel (e.g., a biofuel or gasoline replacement). Thus, the methods provided herein provide a practical, non-polluting technology for producing methyl butenol using methyl butenol synthase proteins and genes. Exemplary cDNA sequences coding for methyl butenol synthases are provided in SEQ ID NOs:1-17, while exemplary amino acids sequences are provided in SEQ ID NOs:18-34 (see FIGS. 1 and 2).

DEFINITIONS

Certain terms used in the specification are defined and presented as follows:

2-methyl-3-buten-2-ol (molecular formula of $C_5H_{10}O$; also known as methyl butenol or methylbutenol (MBO)) is a natural 5-carbon alcohol that is produced and emitted from the foliage by several species of pine, e.g., species in the genus *Pinus*, with the following structure

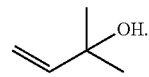

2-methyl-3-buten-2-ol

Biosynthesis of MBO occurs in the chloroplast through the action of the enzyme MBO synthase, which uses DMADP derived from the MEP pathway as a substrate.

"Associated with/operably linked" refers to two DNA sequences that are related physically or functionally. For example, a promoter or regulatory DNA sequence is said to be "associated with" a DNA sequence that codes for an RNA or a protein if the two sequences are operably linked, or situated such that the regulator DNA sequence will affect the expression level of the coding or structural DNA sequence.

"Coding DNA sequence:" refers to a DNA sequence that is translated in an organism to produce a protein. "Expression" of a sequence includes the production of mRNA and/or protein.

"Isolated," in the context of the present invention, an isolated nucleic acid molecule or an isolated polypeptide is a nucleic acid molecule or polypeptide that, by the hand of man, exists apart from its native environment and is therefore not a product of nature. Thus, the term isolated refers to a molecule (e.g., nucleic acid or protein) which is not associated with one or more nucleic acid molecules, proteins or one or more cellular components that are associated with the nucleic acid molecule or protein in vivo. An isolated nucleic acid molecule or an isolated protein may exist in a purified form (e.g., ranges of purity in samples comprising isolated nucleic acid molecules or an isolated protein are 50-55%, 55-60%, 60-65% and 60-70%; ranges of purity also include 70-75%, 75-80%, 80-85%; 85-90%, 90-95%, and 95-100%; however, samples with lower purity can also be useful, such as about <25%, 25-30%, 30-35%, 35-40%, 40-45% and 45-50%.) or may exist in a non-native environment such as, for example, a transgenic host cell.

A "cell" or "host cell" is a prokaryotic or eukaryotic cell.

Alternative fuels, also known as non-conventional fuels, are any materials or substances that can be used as fuels, other than conventional fuels. Conventional fuels include: fossil fuels (petroleum (oil), coal, propane, and natural gas), and nuclear materials such as uranium. Some well known alternative fuels include biodiesel, bioalcohol (methanol, ethanol, butanol), chemically stored electricity (batteries and fuel cells), hydrogen, non-fossil methane, non-fossil natural gas, vegetable oil and other biomass sources. For example, one alternative is alcohol fuel.

Alcohol fuels are usually of biological rather than petroleum sources. When obtained from biological sources, they are known as bioalcohols (e.g. bioethanol). As described herein 2-methyl-3-butene-2-ol (methyl butenol) can be manufactured in organisms carrying a synthase gene of the invention or by fermentative organisms in contact with a synthase protein of the invention and a carbohydrate source. It is a sustainable energy resource that can provide a more environmentally and economically friendly alternative to fossil fuels such as diesel and gasoline. It can be combined with gasoline at different percentages, or can be used in its pure form. Generally, methyl butenol is more advantageous than ethanol as a fuel due to its increased density and relatively little or no water absorption as with ethanol. Unlike butanol, the presence of a branched carbon chain increases its octane rating and the presence of a double carbon-carbon bond can reduce toxicity.

The terms "comprises," "comprising," and the like can have the meaning ascribed to them in U.S. Patent Law and can mean "includes," "including" and the like. As used herein, "including" or "includes" or the like means including, without limitation.

Methyl Butenol Synthase Genes/Proteins

Provided herein are methyl butenol synthase genes including those of SEQ ID NOs: 1-17 or a nucleic acid molecule which comprises a sequence that has at least about 50%, at least about 60%, at least about 70%, about 71%, about 72%, about 73%, about 74%, about 75%, about 76%, about 77%, about 78%, or about 79%, or at least about 80%, about 81%, about 82%, about 83%, about 84%, about 85%, about 86%, about 87%, about 88%, or about 89%, or at least about 90%, about 91%, about 92%, about 93%, or about 94%, or at least about 95%, about 96%, about 97%, about 98%, about 99%, or about 100% sequence identity compared to any one of SEQ ID NOs:1-17 using one of the alignment programs available in the art using standard parameters.

Also provided herein are methyl butenol synthase proteins including those of SEQ ID NOs:18-34 or a polypeptide which comprises a sequence that has at least about 50%, at least about 60%, at least about 70%, about 71%, about 72%, about 73%, about 74%, about 75%, about 76%, about 77%, about 78%, or about 79%, or at least about 80%, about 81%, about 82%, about 83%, about 84%, about 85%, about 86%, about 87%, about 88%, or about 89%, or at least about 90%, about 91%, about 92%, about 93%, or about 94%, or at least about 95%, about 96%, about 97%, about 98%, about 99%, or about 100% sequence identity compared to any one of SEQ ID NOs:18-34 using one of the alignment programs available in the art using standard parameters. In one embodiment, the differences in sequence are due to conservative amino acid changes. In one embodiment, the functional properties of the enzyme are improved through the use of molecular evolution and design studies.

Methods of alignment of sequences for comparison are available in the art. Thus, the determination of percent identity between any two sequences can be accomplished using a mathematical algorithm. Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

Expression of Methyl butenol Synthase and Production of Methyl butenol (MBO)

Methyl butenol synthase can be introduced into any number of organisms to cause them to produce methyl butenol synthase and/or methyl butenol. For example, the genes can be cloned into appropriate expression vectors and expressed in bacteria or yeast. The creation of expression vectors comprising the nucleic acid molecules of the invention and bacterial and yeast transformation techniques are described in detail in the literature and available to an art worker. Typically an expression vector contains (1) prokaryotic DNA elements coding for a bacterial replication origin and an antibiotic resistance gene to provide for the amplification and selection of the expression vector in a bacterial host or DNA elements to allow expression in a eukaryotic host cell (e.g., yeast); (2) regulatory elements that control initiation of transcription such as a promoter; and (3) DNA elements that control the processing of transcripts such as introns, transcription termination/polyadenylation sequence.

Methods to introduce a nucleic acid molecule into a vector are well known in the art (Sambrook et al., 1989). As an example, a vector into which the nucleic acid segment is to be inserted is treated with one or more restriction enzymes (restriction endonuclease) to produce a linearized vector having a blunt end, a "sticky" end with a 5' or a 3' overhang, or any combination thereof. The vector may also be treated with a restriction enzyme and subsequently treated with another modifying enzyme, such as a polymerase, an exonuclease, a phosphatase or a kinase, to create a linearized vector that has characteristics useful for ligation of a nucleic acid molecule into the vector. The nucleic acid molecule that is to be inserted into the vector is treated with one or more restriction enzymes to create a linearized segment having a blunt end, a "sticky" end with a 5' or a 3' overhang, or any combination thereof. The nucleic acid molecule may also be treated with a restriction enzyme and subsequently treated with another DNA modifying enzyme. Such DNA modifying enzymes include, but are not limited to, polymerase, exonuclease, phosphatase or a kinase, to create a polynucleic acid segment that has characteristics useful for ligation of a nucleic acid molecule into the vector.

The treated vector and nucleic acid molecule are then ligated together to form a construct containing a nucleic acid segment according to methods known in the art (Sambrook, 2002). Briefly, the treated nucleic acid molecule and the treated vector are combined in the presence of a suitable buffer and ligase. The mixture is then incubated under appropriate conditions to allow the ligase to ligate the nucleic acid molecule into the vector.

An example of the preparation of an expression vector and expression of MBO synthase in an organism is described in the examples below. However, any expression vector and organism combination for expression available to an art worker may be acceptable for use in the methods of the invention. It will be clear to one of ordinary skill in the art which vector should be used depending on which cell type is used for a host cell.

Alternatively, the methyl butenol synthases of the invention can also be chemically synthesized through peptide synthesis procedures available to the art. The free enzyme can be contacted with an appropriate substrate (a source of carbohydrate) to produced methyl butenol (with our without the use of a host cell).

After preparation of the expression vector and introduction into an appropriate host cell, the cells can be grown in culture to produce methyl butenol synthase and/or methyl butenol, which can be collected (and optionally distilled or condensed).

Alternatively, the culture can be used to produce the free enzyme which is then used to produce MBO. For example, a source of carbohydrate (e.g., sugars (e.g., $C_nH_{2n}O_n$ (n is between 3 and 7), including a monosaccharide (e.g., glucose, dextrose or fructose) or a disaccharide (e.g., sucrose), starches (e.g., a carbohydrate consisting of a large number of glucose units joined together by glycosidic bonds, such as amylase or amylopectin) and/or cellulose (e.g., an organic compound with the formula $(C_6H_{10}O_5)_n$, a polysaccharide consisting of a linear chain of several hundred to over ten thousand $\beta(1\rightarrow 4)$ linked D-glucose units)) and a methyl butenol (MBO) synthase of the invention can be combined to yield MBO, which can be purified further (e.g., distilled or condensed from the head space).

The MBO produced by the methods of the invention can be used as an alternative fuel source.

EXAMPLES

The following examples are provided in order to demonstrate and further illustrate certain embodiments and aspects of the present invention and is not to be construed as limiting the scope thereof.

Example I

Preparation of Methyl Butanol Synthase Vectors and Assay for Activity

Materials and Methods
RNA Extraction

Total RNA was extracted from frozen pine needle tissue from *Pinus sabiniana* using a modified CTAB procedure adapted from (Chang et al. (1993) *Plant Molecular Biology Reporter*, 11(2):113-116.). Needle samples (250 mg) were ground under liquid nitrogen, and extracted for 45 minutes at 70° C. in 800 ul volumes of extraction buffer containing 2% CTAB, 2% PVP-40, 100 mM Tris pH8.0, 25 mM EDTA, 2.0M NaCl, and 0.5 g/L Spermidine with 4% β-mercaptoethanol, 4% PVPP, and an additional 4% PVP40 was added just before use. Following incubation at 70° C. for 45 minutes, samples were extracted twice with 500 μl volumes of 24:1 (v:v) chloroform:isoamyl alcohol solution. RNA was then precipitated by adding ¼ volume of 10M LiCl to the aqueous phase, gently mixing, and storing the mixture overnight at 4° C. Following centrifugation to collect the RNA pellet, the supernatant was discarded and the pellet was re-suspended in 500 μl of SSTE Buffer containing 1.0M NaCl, 0.5% SDS, 10 mM Tris pH8.0, and 1 mM EDTA. This solution was then extracted once with equal volumes of phenol, once with phenol:chloroform: IAA (24:24:1 v/v), and once with chloroform:IAA (24:1 v/v). To precipitate the RNA pellet, 2 volumes of cold (−20° C.) ethanol were added to the supernatant followed by incubation for 2 hours at −20° C. Following centrifugation to collect the pellet, the RNA was air dried, re-suspended in distilled water, and stored at −20 C until further use.
cDNA Synthesis First strand cDNA synthesis was performed using M-MLV reverse transcriptase obtained from Invitrogen (Carlsbad, Calif.) following the manufacturers instructions. Total RNA (2 μg), and 1 μg oligo-dT(17) primer were denatured by incubation at 70° C. for 5 minutes, and then placed on ice for 5 min to anneal the oligo-dT primer to the mRNA polyA tail. Reagents were added to this mixture to achieve a 504 volume containing 1× concentration M-MLV buffer, 0.5 mM dNTPs, 0.1M DTT and 2.5 units of RNasin (Promega, Madison Wis.). The first strand synthesis reactions were performed by incubating for 60 min at 37° C., followed by incubating for 10 min at 42° C., and heat inactivation of the enzyme by incubating at 70° C. for 15 min. Reactions were cooled on ice and stored at −20° C. until further use.
Primer Design.

Initially, degenerate PCR primers were designed to correspond to highly conserved regions of known pine monoterpene synthases. Sequencing of the PCR amplified products revealed 3 distinct sequences which showed high similarity to known pine monoterpene synthases. One sequence contained a phenylalanine residue 7 amino acids upstream of the highly conserved DDXXD motif of terpene synthases. Since this position corresponds to the location of a phenylalanine residue in isoprene synthases and is believed to limit the size of the substrate that can fit into the enzymes active site, this phenylalanine containing sequence was selected for further exploration. To obtain the 5' and 3' ends of this sequence 5' and 3' rapid amplification of cDNA ends (RACE) was employed. For these procedures gene specific forward and reverse primers were designed from the previously selected partial MBO synthase sequence.

PCR Reactions.

Initial PCR reactions were run using 1.25 units of Gotaq DNA polymerase in 30 µl reaction volumes containing 1× Gotaq buffer, 20 µM dNTPs, 1 µM concentrations of each primer, and 0.2 µg template cDNA. In preparation for cloning, full length cDNAs were amplified using either Pfu turbo (Stratagene, La Jolla Calif.) or Platinum Pfx (Invitrogen, Carlsbad Calif.) DNA polymerases according to the manufacturer instructions. To amplify full length cDNAs PCR reactions were run using an initial denaturation of 2 min at 95° C., followed by 35 repetitions of denaturation at 95° C. for 30 sec, annealing at 52° C. for 45 sec, and extension at 72° C. for 3 min, followed by a final extension at 72° C. for 9 min.

Rapid Amplification of cDNA Ends (RACE)

Rapid amplification of cDNA ends (RACE) procedures were employed to amplify the 5' and 3' ends of the partial MBO sequence obtained using degenerate primers. RACE reactions were run using 1.25 units of Gotaq DNA polymerase in 30 µl reaction volumes containing 1× Gotaq buffer, 20 µM dNTPs, 1 µM concentrations of each primer (gene specific, adapter, oligo dt-adapter), and 0.2 µg template cDNA.

Cloning into the Expression Vector

The full length amino acid sequence of the MBO synthase gene contains an N-terminal region similar to the plastid transport sequences found in known conifer monoterpene synthases. These transport sequences have been found to interfere with protein expression in *E. coli* (Williams et al. (1998) *Biochemistry*, (37):12213-12220), hence primers were designed to amplify a fragment of the putative MBO synthase gene lacking this chloroplast transport sequence. Hereafter this will be referred to as an expression length sequence.

Expression length sequences were first ligated into the vector p-GEMT easy (Promega, Madison Wis.) and transformed into the *E. coli* host strain DH5α. pGEMT-easy plasmids containing the MBO synthase gene (pGEMT-MBO) were extracted from the DH5α host and digested with the restriction enzymes SphI and PstI to release an ~1800 bp fragment containing the MBO synthase gene with a 5' SphI and 3' PstI splice site. This fragment was then gel purified and ligated into the expression vector pQE-31 (Qiagen) following digestion of pQE-31 vector with the restriction enzymes SphI and PstI and gel purification of the 3.4 kb digested product. Gel purification of restriction digests was done using a Qiagen gel purification kit (Qiagen). Following ligation of the expression length MBO sequence into the expression vector pQE-31, pQE-31-MBO was transformed into *E. coli* strain BL21-CodonPlus(DE3)-RIL (Stratagene, La Jolla Calif.). This strain of *E. coli* has been modified to correct for codon bias by increasing the expression of several t-RNAs that match codons that are common in plant terpene synthases, but rare in *E. coli*. The MBO synthase gene contains several codons for which t-RNAs in *E. coli* are rare.

Functional Expression and Assay for Methyl Butenol Production.

*E. coli* BL21-Codon Plus(DE3)-RIL containing expression plasmid pQE-31-MBO were grown overnight at 37° C. with shaking at 200 rpm in 5 ml Luri Broth supplemented with 200 µg/ml ampicillin and 34 µg/ml chloramphenicol. Aliquots of bacterial culture (0.5 ml) were placed into 5 ml vials and protein expression induced by adding 0.5 mM IPTG. Vials were capped with a septum and incubated at 30° C. with shaking at 200 rpm for 2 hours before analysis of headspace volatiles by gas chromatography.

To measure methyl butenol in vial headspace, 3 ml aliquots of headspace were withdrawn from the vial and cryofocused by injection into a stainless steel sample loop immersed in liquid nitrogen. The cryofocused sample was then flash vaporized by immersing the sample loop in warm water and flushed onto a widebore capillary DB-1 GC column, 30 m length, 0.32 mm ID, 5 micron film (JW Scientific, Folsom, Calif.) using flow of Helium carrier gas, and analyzed using a Photoionization detector. Component separation was achieved using a temperature program of 30° C. for 10 minutes, followed by a temperature ramp of 2° C. per minute and a hold at 60° C. for 5 minutes. The identity of methylbutenol measured in vial headspace was assessed by comparison of GC peak retention times with those obtained from authentic MBO standards, and by GC-mass spectrometry.

Example II

Assays of Activity of MBO Synthase from *P. sabiniana*

The below assays were run at pH 8.0 in a 50 mM Hepes buffer with 10% glycerol, 100 mM KCl, 20 mM $MgCl_2$, 5 mM $MnCl_2$, and 10 mM DMAPP. Assays were incubated for 2 hours at 37° C., and vial headspace was run on GC. Products were identified by comparing retention times with authentic standards.

Figure 3B:
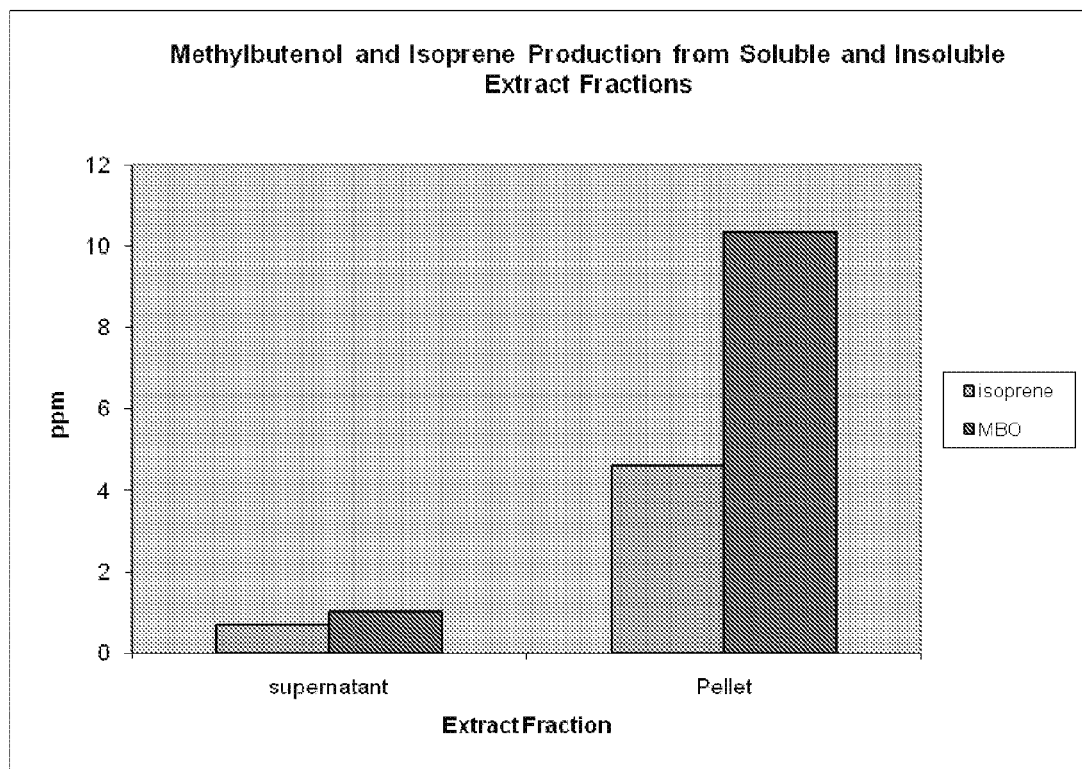

A) Methylbutenol and Isoprene Production from Soluble and Insoluble Extract Fractions FIG. 3 demonstrates that expressed enzyme (with both N and C-terminal His tags (for purification) possess dual catalytic activity and can form both isoprene and methylbutenal from the substrate DMAPP (dimethylallyl pyrophosphate (or -diphosphate)). The enzyme partitions to the insoluble fraction during the extraction process.

B) Effect of Boiling and EDTA on Enzyme Activity

Figure 4:
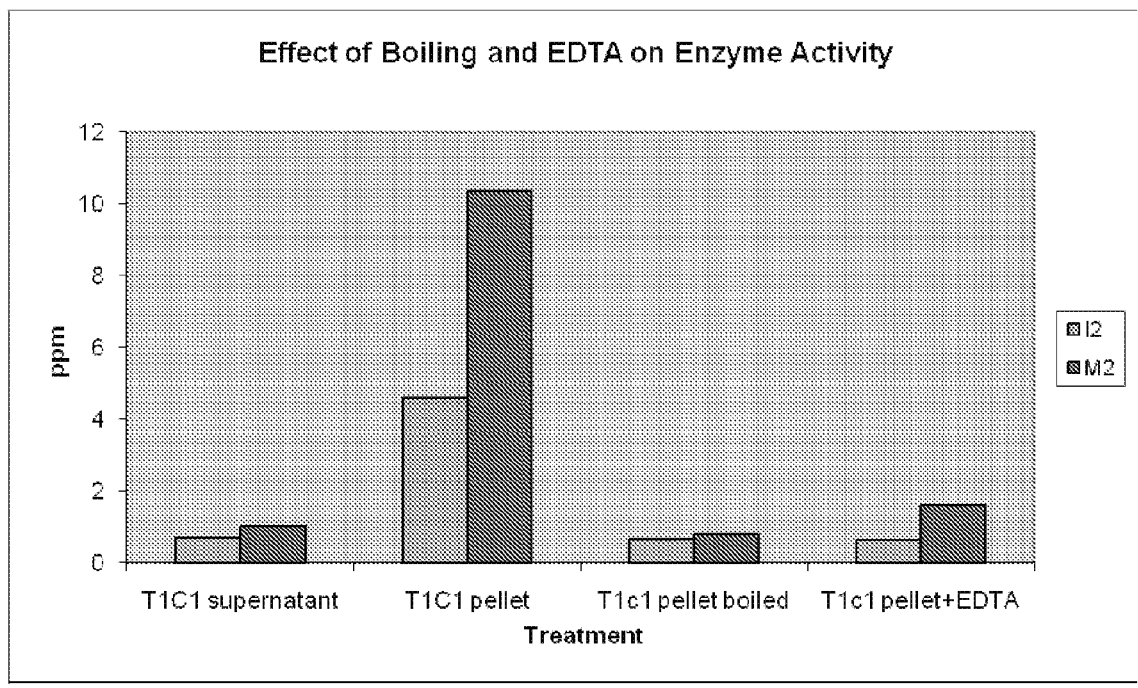
FIG. 4 demonstrates the effect of boiling and EDTA on enzyme activity.

FIG. 4 demonstrates that most of the activity is in the insoluble fraction. Furthermore, experiments determined that the conversion of DMAPP to isoprene and MBO is the result of the MBO synthase. For example, assays run with a boiled pellet (the most active extract) show little or no production of isoprene or MBO. Thus, boiling the extract inactivated the enzyme responsible for DMAPP conversion. Also, assays run with active enzyme in the presence of EDTA show little conversion of DMAPP to isoprene or MBO. This is significant because MBO synthase requires a divalent cation to function. EDTA chelates these cations and thus eliminated enzyme function.

C) Effect of Co-Factor Replacement on MBO Synthase Activity

Figure 5:
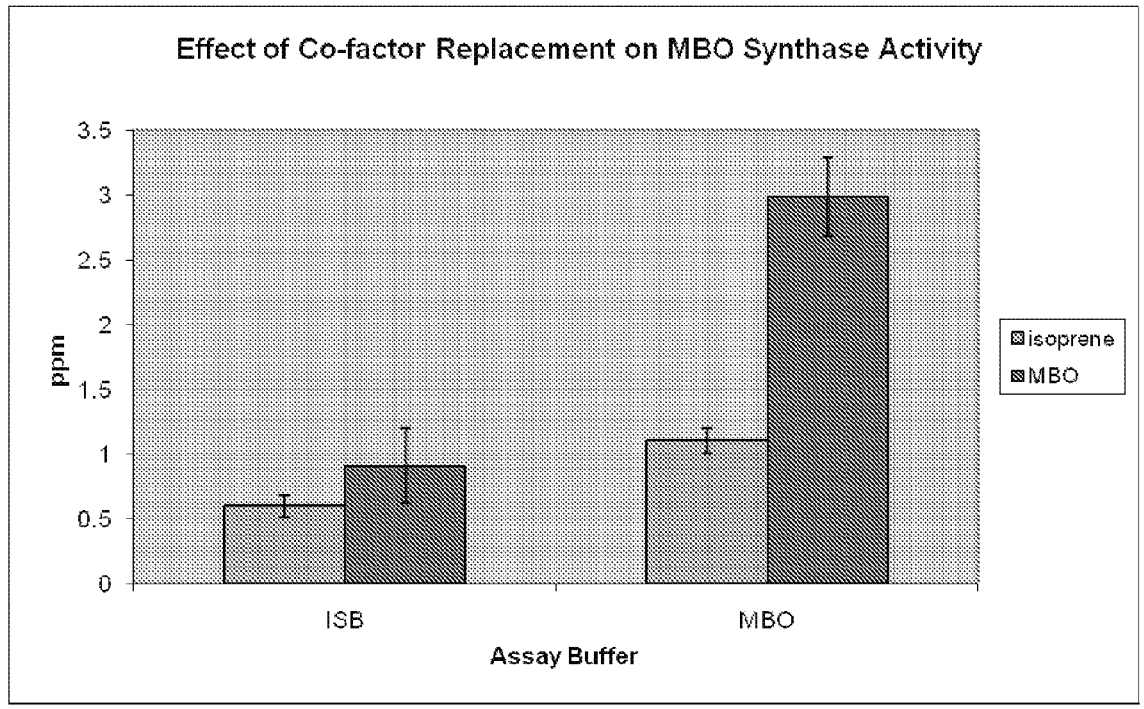
FIG. 5 demonstrates the effect of co-factor replacement on MBO synthase activity.

FIG. 5 demonstrates the effect of selectively removing the cation co-factors for MBO synthase function. The plant extract MBO synthase uses both $Mn^{2+}$ and $K^+$ as co-factors. Angiosperm isoprene synthases uses $Mg^{2+}$. By washing the pellet containing the recombinant MBO synthase protein extracted from *E. coli*, the $Mn^{2+}$ and $K^+$ ions were removed. The pellets were then resuspended in isoprene synthase buffer containing $Mg^{2+}$ or MBO synthase buffer containing $Mn^{2+}$ and $K^+$. Assays run in isoprene synthase buffer (without $Mn^{2+}$ and K⁺ cofactors) show little activity. Assays run in MBO synthase buffer (with both $Mn^{2+}$ and $K^+$) show activity producing isoprene and MBO with about 3 fold preference for forming MBO. Thus, the catalytic activity observed is from an MBO synthase (e.g., the cloned gene).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An isolated and purified methyl butenol (MBO) synthase cDNA molecule, wherein the MBO synthase cDNA molecule comprises any one of SEQ ID NOs: 3-7 or a nucleic acid molecule having at least 95% sequence identity thereof.

2. An isolated and purified methyl butenol (MBO) synthase cDNA, wherein the MBO synthase cDNA comprises SEQ ID NOs:3-7.

3. An expression vector comprising a MBO synthase cDNA molecule of claim 1.

4. An isolated prokaryotic or eukaryotic host cell transformed with a MBO synthase cDNA molecule of claim 1.

5. A prokaryotic or eukaryotic host cell transformed with the vector of claim 3.

6. The host cell of claim 4, wherein the transformed cell expresses MBO synthase.

7. A method to produce methyl butenol comprising transforming a host cell with a cDNA molecule of claim 1 and expressing said molecule in a host cell so as to yield methyl butenol.

8. The method of claim 7, wherein said host cell is a strain of yeast, bacteria, cyanobacteria, eukaryotic micro algae or a combination thereof.

9. The method of claim 8, wherein said yeast is *Saccharomyces cerevisiae*.

10. The method of claim 8, wherein said bacteria is a C5- or C6-fermentative organism.

11. The method of claim 10, wherein said C5-fermenative organism is a species of *Zymomonas*.

12. The method of claim 8, wherein said bacteria is *Klebsiella oxytoca*.

13. The method of claim 8, wherein said cyanobacteria is *Synechococcus* sp., *Synechocystis* sp., or *Anabaena* sp.

14. The method of claim 8, wherein said eukaryotic micro algae is *Chlorella* sp. *Scenedesmus* sp., *Bracteococcus* sp. or *Chlamydomonus* sp.

* * * * *